United States Patent
Chen et al.

(10) Patent No.: US 11,300,509 B2
(45) Date of Patent: Apr. 12, 2022

(54) CLEAVABLE LINKERS FOR PROTEIN TRANSLATION REPORTING

(71) Applicant: 9412-1126 Québec inc., Montréal (CA)

(72) Inventors: Brian Chen, Brossard (CA); El Cheikh Ibrahim Kays, Cambridge, MA (US)

( * ) Notice: Subject to any disclaimer, the term of this patent is extended or adjusted under 35 U.S.C. 154(b) by 0 days.

(21) Appl. No.: 17/350,881

(22) Filed: Jun. 17, 2021

(65) Prior Publication Data
US 2021/0404962 A1 Dec. 30, 2021

Related U.S. Application Data

(60) Provisional application No. 63/040,309, filed on Jun. 17, 2020, provisional application No. 63/040,466, filed on Jun. 17, 2020.

(51) Int. Cl.
*G01N 21/64* (2006.01)
*C07K 14/435* (2006.01)

(52) U.S. Cl.
CPC ... *G01N 21/6428* (2013.01); *C07K 14/43504* (2013.01); *G01N 2021/6439* (2013.01)

(58) Field of Classification Search
CPC ............ C07K 2319/00; C07K 2319/50; C07K 2319/60
See application file for complete search history.

(56) References Cited

U.S. PATENT DOCUMENTS

| | | | |
|---|---|---|---|
| 9,081,014 | B2 | 7/2015 | Waldo et al. |
| 2019/0032154 | A1 | 1/2019 | Chen |

FOREIGN PATENT DOCUMENTS

WO  WO-2006062877 A2 * 6/2006 ......... G01N 33/6842

OTHER PUBLICATIONS

Romei et al. 2019; Split green fluorescent proteins: Scope, limitations, and outlook. Annu Rev Biophys. 48: 19-44.*
Batan et al. 2018; A multicolor split-fluorescent protein approach to visualize zlisteria protein secretion in infection. Biophysical Journal. 114:251-262.*
Dahm, R., Zeitelhofer, M., Gotze, B., Kiebler, M. A. & Macchi, P. Visualizing Mrna localization and local protein translation in neurons. Methods in Cell Biology, vol. 85, 2008, pp. 293-327, doi:10.1016/S0091-679X(08) 85013-3 (2008).
Hinz, F. I., Dieterich, D. C. & Schuman, E. M. Teaching old NCATs new tricks: using non-canonical amino acid tagging to study neuronal plasticity. Current opinion in chemical biology 17, 738-746, doi:10.1016/j.cbpa.2013.07.021 (2013).
Wang, C., Han, B., Zhou, R. & Zhuang, X. Real-Time Imaging of Translation on Single mRNA Transcripts in Live Cells. Cell 165, 990-1001, doi: 10.1016/j.cell.2016.04.040 (2016).
Yan, X., Hoek, T. A., Vale, R. D. & Tanenbaum, M. E. Dynamics of Translation of Single mRNA Molecules In Vivo. Cell 165, 976-989, doi:10.1016/j.cell.2016.04.034 (2016).
Na, Y. et al. Real-Time Imaging Reveals Properties of Glutamate-Induced Arc/Arg 3.1 Translation in Neuronal Dendrites. Neuron 91, 561-573, doi:10 1016/j.neuron.2016.06.017 (2016).
Palmer E, Freeman T. Investigation into the use of C- and N-terminal GFP fusion proteins for subcellular localization studies using reverse transfection microarrays. Comp Funct Genomics.. doi:10.1002/cfg.405, 2004;5(4):342-353.
Zhao, H. L., Yao, X. Q., Xue, C., Wang, Y., Xiong, X. H., & Liu, Z. M. (2008). Increasing the homogeneity, stability and activity of human serum albumin and interferon-alpha2b fusion protein by linker engineering. Protein Expression and Purification, 61(1), 73-7. https://doi.org/10.1016/j.pep.2008.04.013.
Morse, D., & Tannous, B. A. (2012). A water-soluble coelenterazine for sensitive in vivo imaging of coelenterate luciferases. Molecular Therapy□: The Journal of the American Society of Gene Therapy, 20(4), 692-3. https://doi.org/10.1038/mt.2012.38.
NPL-9—Tanenbaum—A-protein-tagging Tanenbaum ME, Gilbert LA, Qi LS, Weissman JS, Vale RD. A protein-tagging system for signal amplification in gene expression and fluorescence imaging. Cell. 2014;159(3):635-646. doi:10.1016/j.cell.2014.09.039.
Zhao N, Kamijo K, Fox PD, et al. A genetically encoded probe for imaging nascent and mature HA-tagged proteins in vivo. Nat Commun. 2019;10(1):2947. Published Jul. 3, 2019. doi:10.1038/S41467-019-10846-1.
Snapp, E. (2005). Design and use of fluorescent fusion proteins in cell biology. Current Protocols in Cell. Chapter 21, Unit 156 21.4. https://doi.org/10.1002/0471143030.cb2104s27.
Yang H, Liu L, Xu F. The promises and challenges of fusion constructs in protein biochemistry and enzymology. Applied Microbiology and Biotechnology. 100 (19): 8273-81. doi:10.1007/s00253-016-7795 (2016).
Lo, C.-A. et al. Quantification of Protein Levels in Single Living Cells. Cell Reports 13, 2634-2644, doi:10.1016/j.celrep.2015.11.048 (2015).
Izuka, R., Yamagishi-Shirasaki, M. & Funatsu, T. Kinetic study of de novo chromophore maturation of fluorescent proteins. Analytical biochemistry 414, 173-178, doi: 10.1016/j.ab.2011.03.036 (2011).
Feinberg, E. H. et al. GFP Reconstitution Across Synaptic Partners (GRASP) defines cell contacts and synapses in living nervous systems. Neuron 57, 353-363, doi:10 1016/j.neuron.2007.11.030 (2008).

(Continued)

*Primary Examiner* — Karen Cochrane Carlson
(74) *Attorney, Agent, or Firm* — Anglehart et al.

(57) ABSTRACT

A method of quantifying expression of a protein of interest with high temporal resolution; it includes providing a cell expressing a large fragment of a split fluorescent protein; transfecting the cell with a vector comprising a nucleic acid molecule comprising a first nucleic acid sequence encoding the protein of interest; a second nucleic acid sequence encoding the small fragment of the split fluorescent protein; and a third nucleic acid sequence encoding a linker protein that is cleaved during translation; quantifying expression of the protein of interest by detecting fluorescence resulting from a combining of the small fragment of the split fluorescent protein and the large fragment of the split fluorescent protein, wherein the linker protein is cleaved during the translation resulting in a stoichiometric ratio of the small fragment of the split fluorescent protein and the protein of interest.

9 Claims, 20 Drawing Sheets

Specification includes a Sequence Listing.

(56) References Cited

OTHER PUBLICATIONS

Kerppola, T. K. Visualization of molecular interactions by fluorescence complementation. Nature reviews. Molecular cell biology 7, 449-456, doi:10.1038/nrm1929 (2006).

Craig FF, Simmonds AC, Watmore D, McCapra F, White MR. Membrane-permeable luciferin esters for assay of firefly luciferase in live intact cells. Biochem J. 1991;276 ( Pt 3)(Pt 3):637-641. doi:10.1042/bj2760637.

Pedelacq, J. D., Cabantous, S., Tran, T., Terwilliger, T. C. & Waldo, G. S. Engineering and characterization of a superfolder green fluorescent protein Nature biotechnology 24, 79-88, doi:10.1038/nbt1172 (2006).

Kim, J. et al. mGRASP enables mapping mammalian synaptic connectivity with light microscopy. Nat Methods 9, 96-102, doi:10.1038/nmeth.1784 (2011).

Yamagata, M. & Sanes, J. R. Transgenic strategy for identifying synaptic connections in mice by fluorescence complementation (GRASP). Front Mol Neurosci 5, 18, doi:10.3389/fnmol.2012.00018 (2012).

Do, K. & Boxer, S. G. Thermodynamics, kinetics, and photochemistry of beta-strand association and dissociation in a split-GFP system. J Am Chem Soc 133, 18078-18081, doi:10.1021/ja207985w (2011).

Kent, K. P. & Boxer, S. G. Light-activated reassembly of split green fluorescent protein. J Am Chem Soc 133, 4046-4052, doi:10.1021/ja110256c (2011).

Huang, Y. M. & Bystroff, C. Complementation and reconstitution of fluorescence from circularly permuted and truncated green fluorescent protein. Biochemistry 48, 929-940, doi:10.1021/bi802027g (2009).

Shaner, N. C., Steinbach, P. A. & Tsien, R. Y. A guide to choosing fluorescent proteins. Nat Methods 2, 905-909, doi:10.1038/nmeth819 (2005).

Ingolia, N. T., Lareau, L. F. & Weissman, J. S. Ribosome profiling of mouse embryonic stem cells reveals the complexity and dynamics of mammalian proteomes. Cell 147, 789-802, doi:10.1016/j.cell 2011.10.002 (2011).

Karpinets, T. V., Greenwood, D. J., Sams, C. E. & Ammons, J. T. RNA:protein ratio of the unicellular organism as a characteristic of phosphorous and nitrogen stoichiometry and of the cellular requirement of ribosomes for protein synthesis. BMC Biol 4, 30, doi:10.1186/1741-7007-4-30 (2006).

Einstein, A. Über die von der molekularkinetischen Theorie der Wärme geforderte Bewegung von in ruhenden Flüssigkeiten suspendierten Teilchen. Annalen der Physik 322, 549-560, doi:10.1002/andp.19053220806 (1905).

Bakshi, S., Siryaporn, A., Goulian, M. & Weisshaar, J. C. Super-resolution imaging of ribosomes and RNA polymerase in live *Escherichia coli* cells. Mol Microbiol 85, 21-38, doi:10.1111/j.1365-2958.2012.08081.x (2012).

Chudakov, D. M., Lukyanov, S. & Lukyanov, K. A. Using photoactivatable fluorescent protein Dendra2 to track protein movement. Biotechniques 42, 553, 555, 557 passim (2007).

Kays, I., & Chen, B. E. Protein and RNA quantification of multiple genes in single cells. BioTechniques, 66(1), 15-21. doi: 10.2144/btn-2018-0130. (2019).

Chiu-An Lo, Brian E.Chen. Parental allele-specific protein expression in single cells In vivo, Developmental Biology, vol. 454, Issue 1, Oct. 1, 2019, pp. 66-73.

Fan, J. Y. et al. Split mCherry as a new red bimolecular fluorescence complementation system for visualizing protein-protein interactions in living cells. Biochemical and biophysical research communications 367, 47-53, doi: 10.1016/j.bbrc.2007.12.101. (2008).

Nilson, L. A. & Schupbach, T. EGF Receptor Signaling in *Drosophila* Oogenesis. Current Topics in Developmental Biology, vol. 44, 1998, pp. 203-243.

Kramer, G., Boehringer, D., Ban, N., & Bukau, B. The ribosome as a platform for cotranslational processing, folding and targeting of newly synthesized proteins. Nature Structural & Molecular Biology, 16(6), 589-597. https://doi.org/10.1038/nsmb.1614. (2009).

Ross, J. F., & Orlowski, M. (1982). Growth-rate-dependent adjustment of ribosome function in 15S chemostat-grown cells of the fungus Mucor racemosus. Journal of Bacteriology, 149(2), 650-3.

International application No. PCT/CA2021/050828 International Search Report dated Oct. 19, 2021.

International application No. PCT/CA2021/050828 Search Strategy dated Oct. 19, 2021.

International application No. PCT/CA2021/050828 Written Opinion of the International Searching Authority dated Oct. 19, 2021.

Chen, X. et al. "Fusion protein linkers: property, design and functionality". Advanced Drug Delivery Reviews, Oct. 15, 2013 (Oct. 15, 2013), vol. 65(10), pp. 1357-1369. ISSN: 0169-409X; DOI: 10.1016/j.addr.2012.09.039.

\* cited by examiner

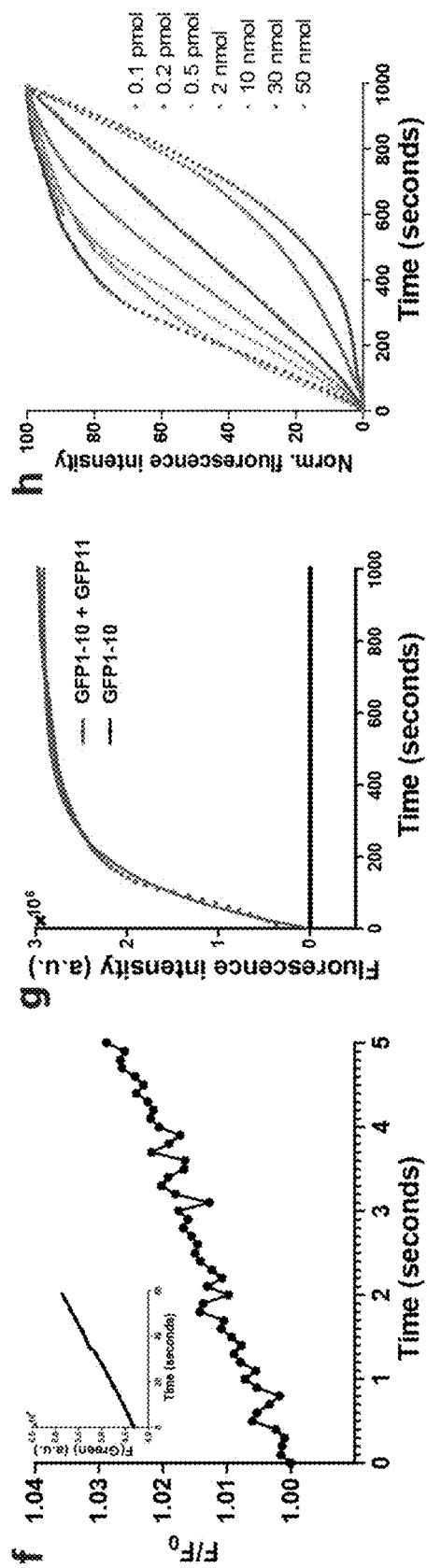

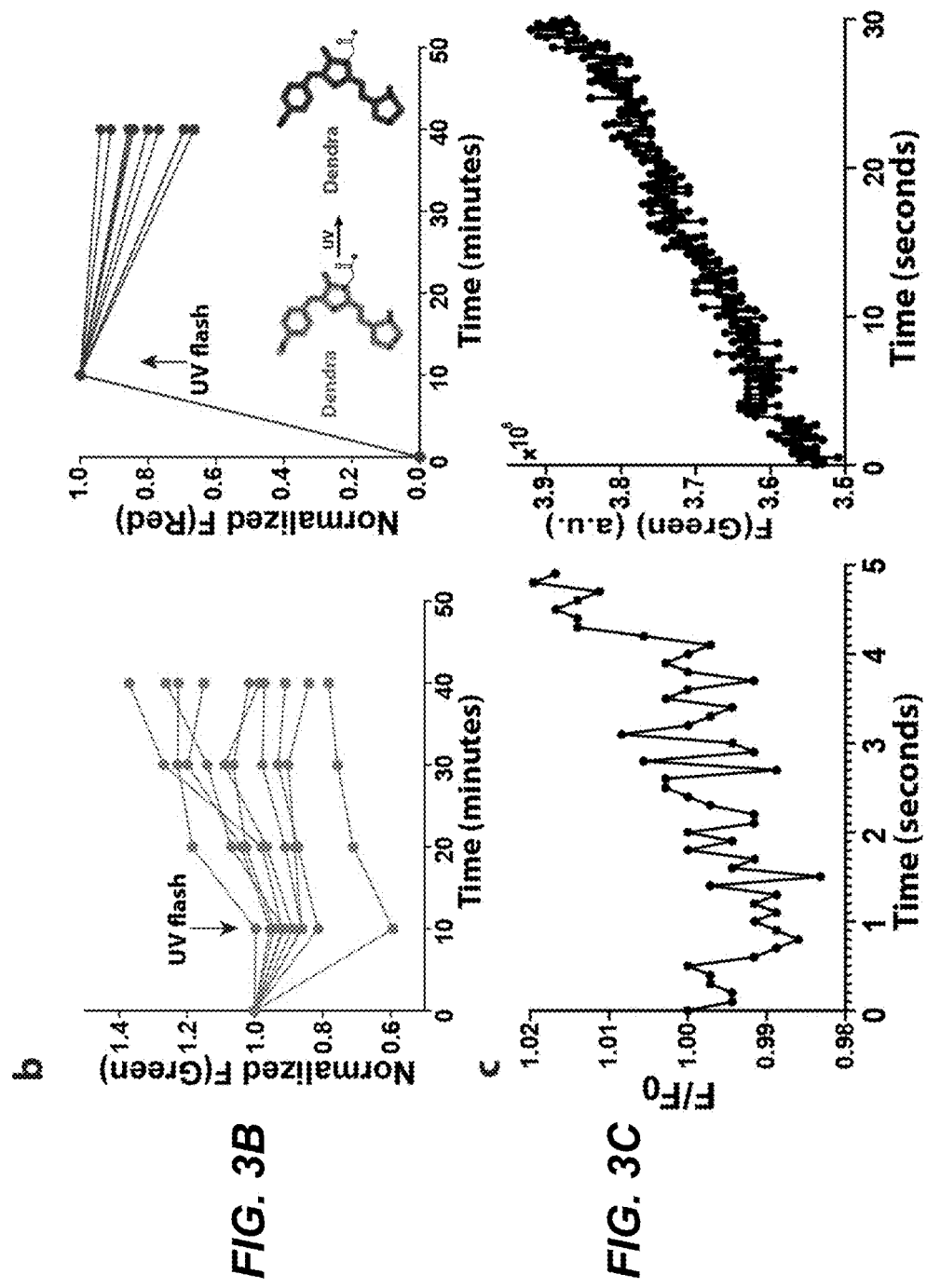

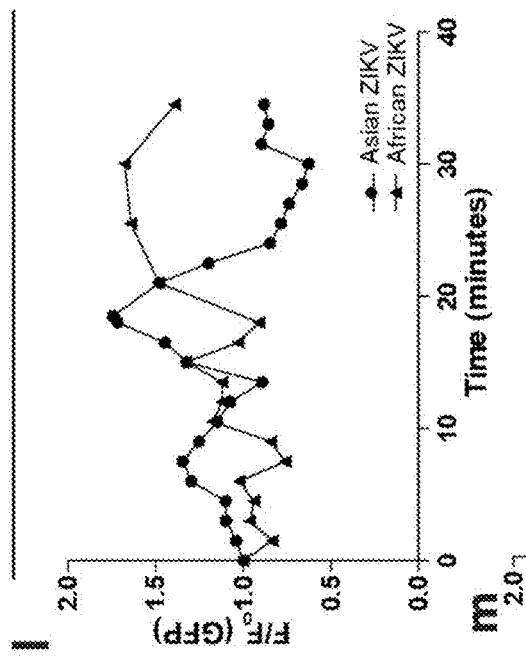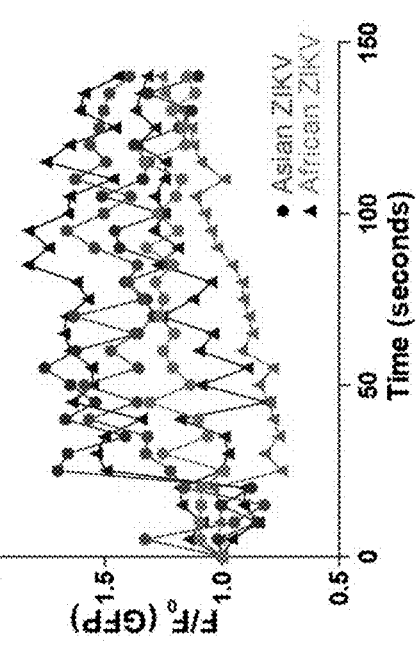
FIG. 4L
FIG. 4M

CLEAVABLE LINKERS FOR PROTEIN TRANSLATION REPORTING

CROSS-REFERENCE TO RELATED APPLICATIONS

The present application claims priority from U.S. provisional patent application No. 63/040,309, filed on Jun. 17, 2020, incorporated herein by reference, and U.S. provisional patent application No. 63/040,466, filed on Jun. 17, 2020, incorporated herein by reference.

Reference to a sequence listing submitted via EFS-WEB

The content of the ASCII text file of the sequence listing named "P2116US02-Sequence_Listing_v4 ST25" which is 29.6 kb in size was created on Jan. 31, 2022 and electronically submitted herewith via EFS-Web is incorporated herein by reference.

TECHNICAL FIELD

The present disclosure relates to protein quantification ratioing, and more particularly to protein quantification ratioing using a cleavable protein linker between a reporter protein and a protein of interest for protein translation reporting.

BACKGROUND

As described in U.S. Patent Application U.S. 2019/0032154, protein quantification ratioing is a method of quantifying amounts of protein generated through translation. A translated protein linker located between a protein of interest that will be the subject of quantification, and a fluorescent protein, is cleaved, resulting in a stoichiometric ratio between the protein of interest and the fluorescent protein. As such, measuring the amount of the fluorescent protein provides a precise indicator as to the translated quantity of the protein of interest, based on the ratio.

However, one of the disadvantages of the teachings of U.S. 2019/0032154 involves the time taken for the translated fluorescent protein to fold and mature. The delay in folding and maturing does not allow the technique to report results as close as possible to translation. This is particularly problematic when considering the speed of molecule diffusion at small, subcellular length scales. A typical protein might diffuse across a 20 μm cell in 40 seconds, but will diffuse 350 μm in the ten minutes it may require to fold and mature. The output of any protein synthesis reporter should occur within milliseconds to accurately detect synthesis events within the micrometer length scale or risk degrading spatial and temporal resolution. This is not possible when the fluorescent protein takes such prolonged periods to fold.

As such, it would be advantageous to improve upon known techniques to arrive at a protein quantifying technique with a high spatial and temporal resolution.

SUMMARY

The present disclosure relates to a protein quantification technique that provides a high spatial and temporal resolution for protein translation reporting, thereby overcoming the shortcomings associated with the technique described in U.S. 2019/0032154.

The protein quantification technique is achieved by having a cleavable protein linker (a small peptide), linking the protein of interest not to the entire fluorescent protein, but to a small fragment (i.e. an active portion) of a split fluorescent protein. The larger fragment of the fluorescent protein is present and folded (already expressed), and once the cleavable protein linker is cleaved, the small fragment of the split fluorescent protein associates with the larger portion, thereby constituting the fluorescent protein, and causing fluorescence. As such, as only the smaller portion of the split fluorescent protein is translated with the cleavable protein linker and the protein of interest, only the smaller portion of the fluorescent protein needs to fold and mature (the remaining larger fragment of the split fluorescent protein, separate, already being folded and matured). This reduces significantly the folding and maturation time associated with the fluorescent protein, and also the delay between translation of the protein-of-interest and the generation of fluorescence. As such, the fluorescent signal is detected far closer to the time of translation then when using techniques described in U.S. 2019/0032154.

Moreover, the present disclosure addresses an additional problem associated with having only the nucleic acid encoding of the small fragment of the split fluorescent protein (which is short in length) joined to the nucleic acid encoding the cleavable protein linker. It was found that the PQR (protein quantification reporter) linkers described in U.S. 2019/0032154 resulted in problems in translation of the nucleic acid encoding the small fragment of the split fluorescent protein, and folding of the small fragment of the split fluorescent protein. As such, new linker proteins, and their corresponding DNA encoding the new linkers, were devised, hereby referred to as PTR (protein translation reporter) linkers. These PTR linkers, or at least a portion thereof, associate the small fragment of the split fluorescent protein to the protein of interest, while remedying the protein expression and fluorescence problems associated with the PQR linkers and the small portion of the fluorescent protein. The PTR linkers can also be cleaved, thereby resulting in a stoichiometric ratio between the protein of interest and the fluorescence signal, with the separated small fragment of the split fluorescent protein free to bond with the large fragment of the split fluorescent protein, thereby fully constituting the fluorescent protein. As such, the present disclosure presents a solution to remedy the problem encountered with the PQR linkers of U.S. 2019/0032154.

The PTR linker includes a small peptide that is co-translated with the protein of interest, and binds and activates a fluorescent reporter after its co-translation, as shown in FIG. 5. In some examples, the peptide may be based on the complementation of a split green fluorescent protein (GFP) into two non-fluorescent parts[17,18]: e.g. a larger portion containing ten of the eleven strands of the GFP beta-barrel structure (GFP1-10), and the eleventh strand of the beta barrel comprised of only 16 residues (GFP11). High levels of expression of GFP1-10 in a cell allow for folding and chromophore maturation to occur independently and prior to protein translation reporting.

Using split GFP components as Protein Translation Reporters (PTRs) to monitor protein translation events offers a number of advantages over probe or antibody-based approaches. For example, PTRs are genetically encoded and the signals are fluorescence-based, which minimizes the cell or animal invasiveness associated with detecting protein translation. The untagged protein of interest remains free in its native form after synthesis, which ensures proper localization, secretion, or post-translational modification. In addition, the fast reconstitution of the reporter immediately after translation would provide exceptional spatial and temporal resolution that can be used to localize protein translation events in subcellular compartments such as the endoplasmic reticulum or neuronal dendrites. Such an approach allows, for instance, for direct, non-invasive and long-term observation of endogenous local protein synthesis in neurons, which is key to understanding the distal processes that both maintain cellular homeostasis and mediate plasticity.

In some embodiments, expressing the GFP11 peptide using PTR linkers produces the stoichiometric relationship with the protein of interest, allowing for quantification of protein translation[14], as shown in FIG. 1A. In addition, the fluorescence intensity resulting from the reconstitution of GFP1-10 and GFP11 peptides in vitro was linearly dependent on the concentration of the reactants over several orders of magnitude, as illustrated in FIG. 1B, top, indicating that the fluorescence intensity resulting from the translation of GFP11 is proportional to and can be used to quantify the level of translation of the protein of interest (illustrated in FIG. 1B, bottom).

A first broad aspect is a nucleic acid molecule for use in protein quantification, including a first nucleic acid sequence encoding a peptide corresponding to SEQ ID NO: 26 or 27; a second nucleic acid sequence encoding a peptide corresponding to SEQ ID NO: 36; and a third nucleic acid sequence encoding a small fragment of a split fluorescent protein, wherein one of: the second nucleic acid sequence is located between the first nucleic acid sequence and the third nucleic acid sequence; and the first nucleic acid sequence is next to the third nucleic acid sequence, and the second nucleic acid sequence is next to the third nucleic acid sequence, opposite from the first nucleic acid sequence.

In some embodiments, the second nucleic acid sequence may be located between the first nucleic acid sequence and the third nucleic acid sequence.

In some embodiments, the first nucleic acid sequence may be next to the third nucleic acid sequence, and the second nucleic acid sequence is next to the third nucleic acid sequence, opposite from the first nucleic acid sequence.

In some embodiments, the second nucleic acid sequence may encode a peptide corresponding to SEQ ID NO: 37.

In some embodiments, the second nucleic acid sequence may encode a peptide corresponding to SEQ ID NO: 39.

In some embodiments, the first nucleic acid sequence may correspond to SEQ ID NO: 28 and encodes the peptide corresponding to SEQ ID NO: 26; or the second nucleic acid sequence may correspond to SEQ ID NO: 29 and encodes the peptide corresponding to SEQ ID NO: 27.

In some embodiments, the second nucleic acid sequence encoding a peptide may correspond to any one of SEQ ID NO: 31-35.

Another broad aspect is a host cell transfected with the nucleic acid molecule as defined herein.

In some embodiments, the host cell may express a large fragment of the split fluorescent protein, and wherein the small fragment of the split fluorescent protein and the large fragment of the split fluorescent protein may be configured to combine and fluoresce.

In some embodiments, the host cell may not be a fertilized egg or a totipotent stem cell.

Another broad aspect is a method of quantifying expression of a protein of interest with high temporal resolution. The method includes providing a cell expressing a large fragment of a split fluorescent protein, wherein the large fragment of the split fluorescent protein does not fluoresce until the large fragment of the split fluorescent protein associates with a corresponding small portion of the split fluorescent protein; transfecting the cell with a vector comprising a nucleic acid molecule comprising: a first nucleic acid sequence encoding the protein of interest; a second nucleic acid sequence encoding the small fragment of the split fluorescent protein; and a third nucleic acid sequence encoding a linker protein that is cleaved during translation, wherein at least a portion of the nucleic acid sequence encoding the linker protein is located between the nucleic acid sequence encoding the protein of interest and the nucleic acid sequence encoding the small fragment of the split fluorescent protein; following translation of the peptide corresponding to the nucleic acid molecule, quantifying expression of the protein of interest by detecting fluorescence and the large fragment of the split fluorescent protein, wherein the linker protein is cleaved during the translation resulting in a stoichiometric ratio of the small fragment of the split fluorescent protein and the protein of interest.

In some embodiments, the nucleic acid sequence encoding the linker protein may encode a PTR linker, and the nucleic acid sequence encoding the linker protein may be located between the nucleic acid sequence encoding the protein of interest and the nucleic acid sequence encoding the small fragment of the split fluorescent protein.

In some embodiments, the nucleic acid sequence encoding the linker protein may encode a PTR linker, and wherein a first portion of the nucleic acid sequence encoding the linker protein may be located between the nucleic acid sequence encoding the protein of interest and the nucleic acid sequence encoding the small fragment of the split fluorescent protein, and wherein a second portion of the nucleic acid sequence encoding an inert portion of the linker protein may be connected to the nucleic acid sequence encoding the small fragment of the split fluorescent protein opposite the nucleic acid sequence encoding a PQR portion of the linker protein.

In some embodiments, the nucleic acid molecule may be a deoxyribonucleic acid molecule.

In some embodiments, the cell may be part of an organism comprising many of the cells.

In some embodiments, the organism may be an animal.

In some embodiments, the third nucleic acid sequence may include a fourth nucleic acid sequence encoding the amino acid sequence of SEQ ID NO: 36.

In some embodiments, the cell may be a dendrite.

In some embodiments, the quantifying may be performed using a linear regression technique.

In some embodiments, the third nucleic acid sequence may include a fifth nucleic acid sequence encoding the amino acid sequence of SEQ ID NO: 26 or 27.

Another broad aspect is a nucleic acid molecule encoding a small fragment of a split Dendra fluorescent protein comprising a nucleic acid sequence of ID NO: 22, wherein the small fragment of the split Dendra fluorescent protein is configured to associate with a large fragment of the split Dendra fluorescent protein to fluoresce.

In some embodiments, the large fragment of the split Dendra fluorescent protein may include the amino acid sequence of SEQ ID NO: 8.

In some embodiments, the amino acid sequence of the small fragment of the split fluorescent protein may be SEQ ID NO: 9.

Another broad aspect is a method of generating fluorescence comprising transfecting a cell with a vector comprising the nucleic acid molecule defined herein encoding the small fragment of the split Dendra fluorescent protein, wherein the cell expresses a large fragment of the split Dendra fluorescent protein, and wherein fluorescence is generated once the split Dendra fluorescent protein is translated within the cell and combines with the large fragment of the split Dendra fluorescent protein.

Another broad aspect is a method of generating a vector for use in protein quantification ratioing. The method includes introducing a nucleic acid sequence encoding a PTR linker and a small fragment of a split fluorescent protein downstream from a nucleic acid sequence encoding a protein of interest.

Another broad aspect is a kit for performing protein quantification ratioing, including a first oligonucleotide molecule comprising: a first nucleic acid sequence encoding a PTR linker; a second nucleic acid sequence encoding the small fragment of the split fluorescent protein; and a third nucleic acid sequence encoding a linker protein that is cleaved during translation, wherein at least a portion of the nucleic acid sequence encoding a portion of the linker protein that is cleaved is located between the nucleic acid sequence encoding the protein of interest and the nucleic acid sequence encoding the small fragment of the split fluorescent protein; and one of: a cell expressing a large fragment of the split fluorescent protein; and a second oligonucleotide molecule comprising the nucleic acid sequence encoding the large fragment of the split fluorescent protein.

In some embodiments, the kit may include the second oligonucleotide molecule comprising the nucleic acid sequence encoding the large fragment of the split fluorescent protein, and wherein the second oligonucleotide molecule may be a high-expression plasmid.

In some embodiments, the linker protein encoded by the third nucleic acid sequence may include an inert portion, and wherein the amino acid sequence of the inert portion may be SEQ ID NO: 36.

In some embodiments, the amino acid sequence of the inert portion may be SEQ ID NO: 37.

In some embodiments, the amino acid sequence of the inert portion may be SEQ ID NO: 38.

In some embodiments, the amino acid sequence of the inert portion may be SEQ ID NO: 39.

In some embodiments, the kit may include the cell expressing a large fragment of the split fluorescent protein, and wherein the cell is part of a transgenic animal and the transgenic animals comprises a plurality of the cells.

BRIEF DESCRIPTION OF THE DRAWINGS

The invention will be better understood by way of the following detailed description of embodiments of the invention with reference to the appended drawings, in which:

FIGS. 1F-G, relating to the stoichiometric production of GFP11 reporter as a function of time using a PTR linker to allow instantaneous detection of protein translation, are graphs that illustrate that reconstitution of split GFP as a function of seconds passed. Fluorescence reconstitution kinetic traces of split GFP shows the linear phase of reconstitution over the first 5 seconds, and the first minute (inset). Within the first second of reconstitution, i.e., in milliseconds, fluorescence emission begins (FIG. 1F), and the fluorescence intensity of the reaction rose logarithmically and began to saturate after 5 minutes (FIG. 1G). To determine the speed of reconstitution of the modified split GFP, purified GFP1-10 at 3 mM was combined with varying concentrations of GFP11 at 37° C. and found that fluorescence was detected immediately upon mixing the two solutions. To obtain kinetic measurements of the reconstitution reaction at sub-second timescales, an ultrasensitive fluorescence spectrophotometer was used. A stopped-flow dispenser was used to mix and deliver known volumes of GFP1-10 and GFP11 proteins. This allowed the establishment of a to for the moment split GFP components first interact. Green fluorescence was detected immediately upon mixing the two solutions (within 100 ms), and the fluorescent intensity of the reconstitution reaction steadily increased throughout the recording window (~60 seconds). Fluorescence increase over time from the bimolecular reaction was modeled as pseudo-first order and fit to a one phase association curve to determine the observed rate constant (kobs) of GFP11 peptide binding for each concentration of GFP11 tested. For 50 nM GFP11 and excess GFP1-10, the kobs is 0.003 s-1. Using these kobs, the association rate constant (kon) was calculated as $7.6 \times 10^5$ M-1 s-1, which falls within the diffusion-controlled regime.

FIG. 1H is a graph that shows that GFP11 has high affinity for GFP1-10. To determine the dissociation constant (Kd) of the GFP11 peptide, the fluorescence increase over time with varying GFP11 peptide concentrations was also fit to a one site binding model, and the Kd was 481±116 pM ($R^2$=0.96, $p<0.05$), demonstrating that GFP11 peptide binds GFP1-10 with very high affinity. In the volume of a medium-size cell, the slower, lowest concentration reactions would generate tens of reconstituted molecules per second, and for the average protein synthesis hundreds per second. Scale bars are 30 µm in c and d, and 60 µm in e.

FIG. 3A are photographs and FIG. 3B are graphs, relating to spectral variants of split PTR, that show that split photoconvertible fluorescent proteins can be used with PTR to reset protein synthesis measurements at any time. Reconstituted Dendra2 emits green fluorescence (FIG. 3A, left panels), but can be permanently photoconverted to emit red fluorescence upon UV illumination. HEK293 cells co-expressing Dendra1-10 and Dendra11 produce bright green uniform fluorescence that photoconverted to red fluorescence with a 5 second flash of UV light (FIG. 3A, right panels). The time course of the green and red fluorescence intensities (FIG. 2B) before and after photoconversion (UV flash) shows the relative changes of reconstituted split Dendra2. As protein synthesis continued, Dendra2 green fluorescence increased over time scales of minutes in single cells to values beyond their starting intensity (mean±s.e.m. is shown). Scale bar is 20 µm.

FIG. 3C, relating to spectral variants of split PTR, are graphs that illustrate that In vitro reconstitution of Dendra1-10 and Dendra11 resulted in green fluorescence that was recorded every 0.1 seconds for a duration of 30 seconds. Green fluorescence intensity was detected immediately after mixing of Dendra1-10 lysate and Dendra11 purified peptide at a 2:1 molar ratio at room temperature.

FIGS. 4L-M, relating to direct observation of protein synthesis over time in vivo, are graphs that illustrate that the subcellular protein translation dynamics of African (strain Ar51524) and Asian (strain 150989) ZIKV proteins can be tracked in the living animal over time at varying timescales.

DETAILED DESCRIPTION

Figure 1A:
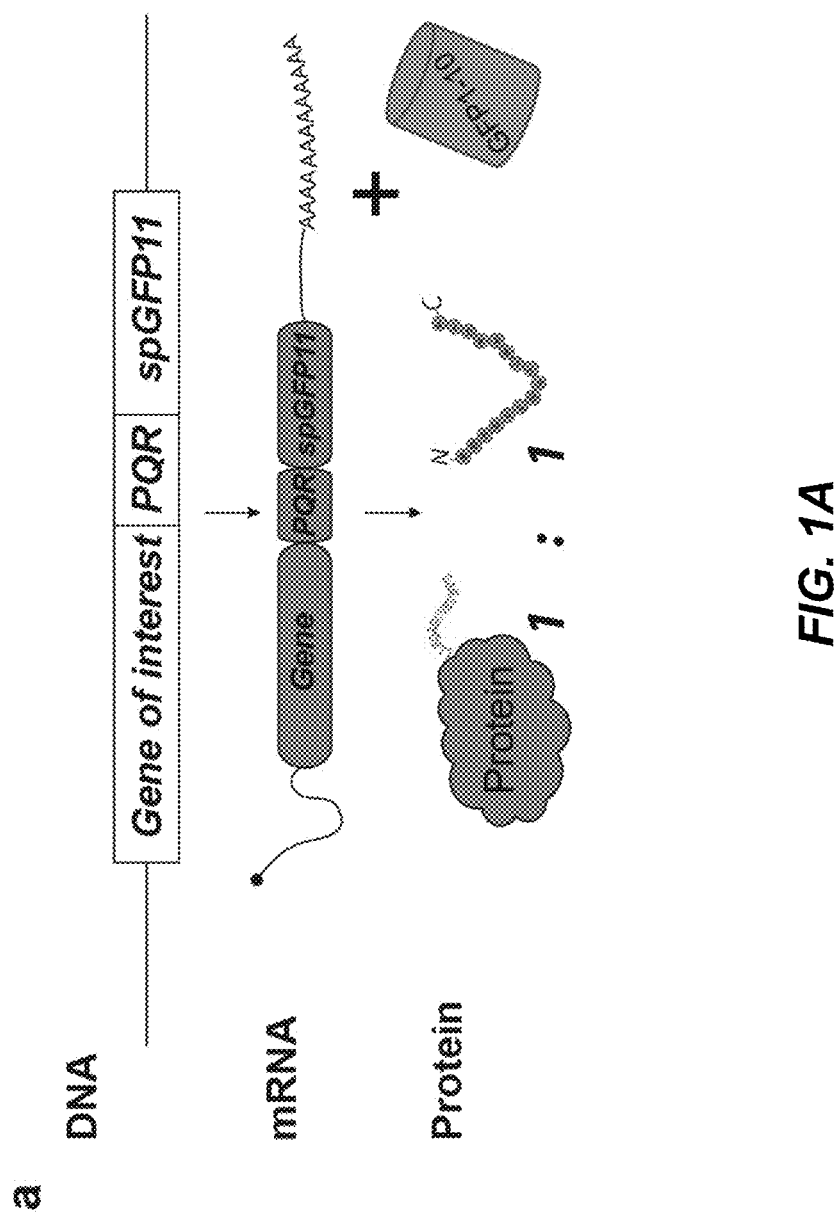
FIG. 1A, relating to the stoichiometric production of GFP11 reporter using a linker to allow instantaneous detection of protein translation, is a drawing that illustrates that an insertion of a Protein Quantitation Reporter (PQR) between a split GFP11 reporter (GFP11) and a gene of interest creates a polycistronic mRNA for co-transcription and co-translation of GFP11 and the gene of interest. The sequence of As of the mRNA is a poly(A) tail and corresponds to SEQ ID NO: 81. The PQR, the sequence shown in FIG. 1A corresponding to SEQ ID NO: 82, construct allows for one molecule of GFP11 to be synthesized for every one molecule synthesized of a protein of interest. In the presence of GFP1-10, the split GFP parts reconstitute and produce green fluorescence.

The present disclosure relates to improved techniques for quantifying protein expression by providing better temporal and spatial resolution following protein translation. As such, the techniques disclosed herein may be used to quantify protein expression in cells with spatially restricted local protein synthesis, such as in neurons.

The present disclosure remedies the shortcomings of the protein quantification technique described in U.S. 2019/0032154, where the time taken for folding and maturation of the reporter protein reduces the temporal and spatial resolution of the quantification (e.g. the fluorescent protein takes time to fold and to fluoresce). In the present disclosure, a linker protein (or a nucleic acid sequence encoding the protein linker) is joined not to an entire reporter protein (i.e. a fluorescent protein), but to only a fragment of the fluorescent protein. The cells subject to protein quantification already express the remaining fragment of the fluorescent protein, e.g., through transfection. As such, the larger fragment of the fluorescent protein is already translated and folded.

Therefore, the present disclosure relates to a nucleic acid sequence that encodes three proteins: a linker protein (PTR linker, having, in some examples, a PQR portion and an inert portion), a small fragment of a split fluorescent protein, and a protein of interest to be quantified.

When the target cells translate the small fragment of the split fluorescent protein, it binds to the already folded larger fragment of the split fluorescent protein, thereby constituting the entire fluorescent protein and generating fluorescence far faster than if the entire fluorescent protein had to fold. As such, as the protein of interest is translated sequentially with respect to the small fragment of the split fluorescent protein, the translated protein of interest is separated from the small fragment of the split fluorescent protein due to the composition of the PTR linker as described herein. By quantifying the amount of protein expression of the small fragment of the split fluorescent protein (e.g., by measuring fluorescence), it is possible to determine the level of expression of the protein of interest.

Furthermore, the present disclosure also relates to improved cleavable protein linkers (and the corresponding nucleic acid sequence) for interconnecting a protein of interest and the small portion of the fluorescent protein. It has been discovered that although the PQR linkers disclosed in U.S. 2019/0032154 may be suitable for interconnecting a protein of interest and the small portion of the fluorescent protein, the PQR linkers disclosed in U.S. 2019/0032154 can result in non-optimal protein expression of the small fragment of the split fluorescent protein. The protein linkers disclosed herein, referred to as PTR linkers, provide for better protein expression of the small portion of the fluorescent protein.

It will also be understood that use of the PTR linkers disclosed herein is not limited to interconnecting a protein of interest and a small fragment of a split fluorescent protein. The PTR linkers can also be used for interconnecting the protein of interest and an entire reporter protein (e.g., an entire fluorescent protein, an antibody protein, etc.), similar to the term reporter protein as described in U.S. 2019/0032154.

The present disclosure also relates to novel split fluorescent proteins, that can be used in the context of protein quantification ratioing as described herein, or for other purposes.

Figure 5:
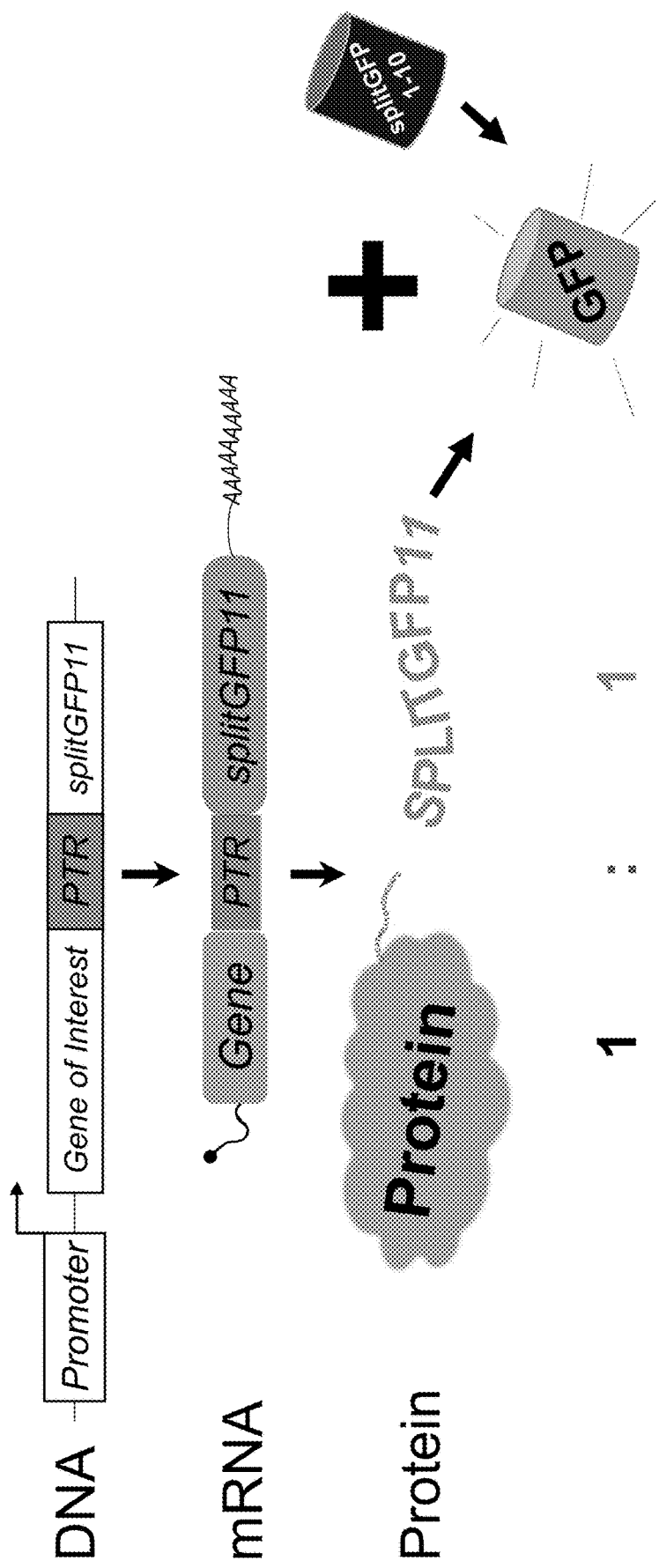
FIG. 5 is a drawing illustrating the protein quantification method when the entire nucleic acid sequence encoding the PTR linker, corresponding to SEQ ID NO: 84, is located between the nucleic acid sequence encoding the protein of interest and the nucleic acid sequence encoding the small fragment of the split fluorescent protein. The sequence of As of the mRNA is a poly(A) tail and corresponds to SEQ ID NO: 83.

The PTR linker may include two portions, a PQR portion and an inert portion as further described herein. As shown in FIG. 5, a vector is provided including a nucleic acid sequence encoding a protein of interest, a nucleic acid sequence encoding a small fragment of a split fluorescent protein, and a nucleic acid sequence encoding the PTR linker that is located between the nucleic acid sequence encoding the protein of interest and the nucleic acid sequence encoding the small fragment of the split fluorescent protein. The vector may be transfected into a cell.

The vector or nucleic acid molecule may be transcribed to its corresponding mRNA using the transcription machinery of the cell.

During or after translation of the mRNA, the expressed protein is cleaved at the PQR portion of the PTR linker to yield a stoichiometric ratio between the protein of interest and the small fragment of the split fluorescent protein. The small fragment of the split fluorescent protein combines with the expressed and folded large fragment of the split fluorescent protein (already expressed by the cell, that has been, e.g., previously transfected with the corresponding nucleic acid sequence). The combined fragments of the split fluorescent protein fluoresce, and the intensity of fluorescence can provide an indicator as to the quantity of protein of interest that has been translated by the cell with elevated temporal resolution.

Figure 6:
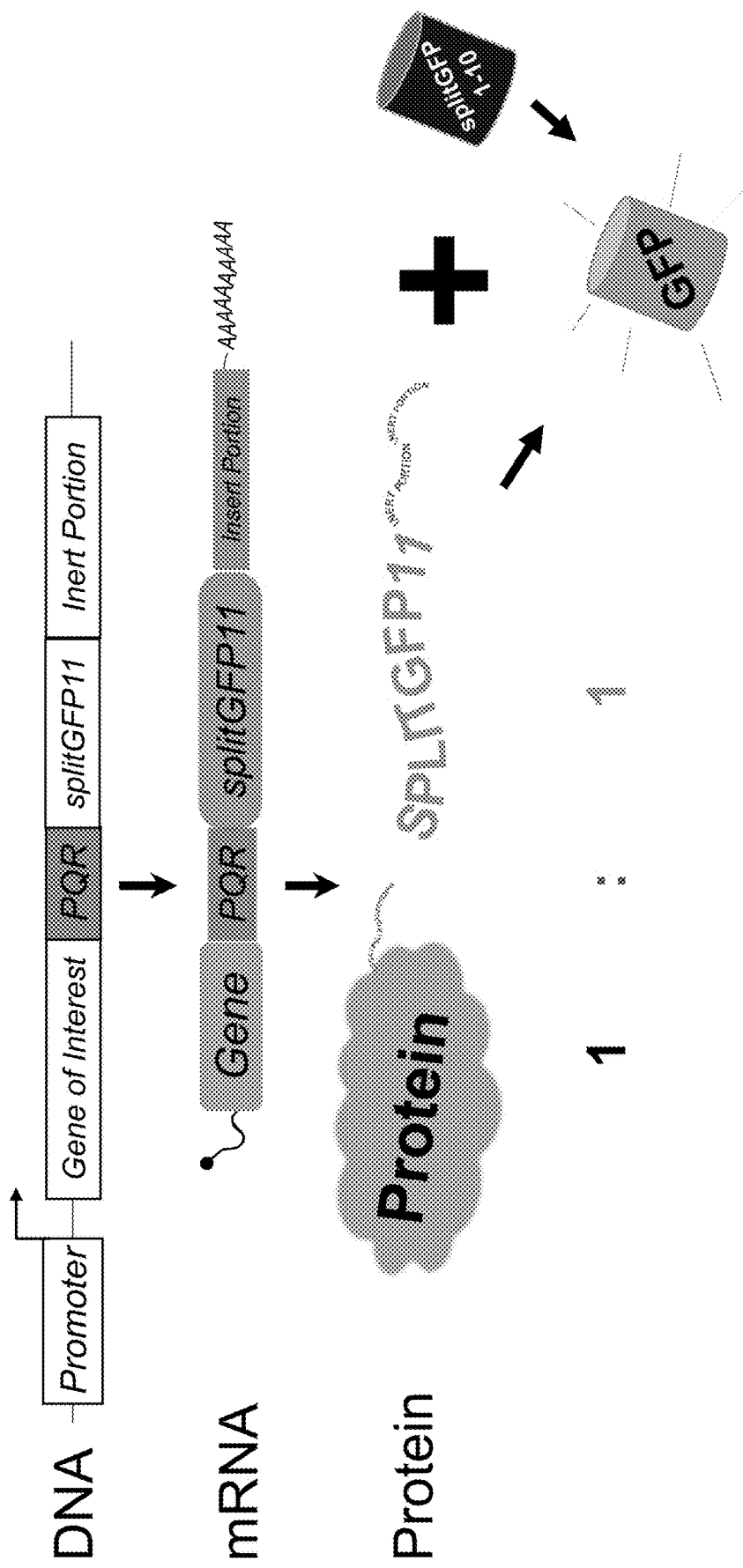
FIG. 6 is a drawing illustrating the protein quantification method when the nucleic acid sequence encoding the PQR portion of PTR linker, corresponding to SEQ ID NO: 84, is located between the nucleic acid sequence encoding the protein of interest and the nucleic acid sequence encoding the small fragment of the split fluorescent protein, and where the nucleic acid sequence encoding the inert portion of the PTR linker is located after the nucleic acid sequence encoding the small fragment of the split fluorescent protein. The sequence of As of the mRNA is a poly(A) tail and corresponds to SEQ ID NO: 83.

As shown in FIG. 6, the nucleic acid sequence encoding the PQR portion of PTR linker may be located between the nucleic acid sequence encoding the protein of interest and the nucleic acid sequence encoding the small fragment of the split fluorescent protein, and where the nucleic acid sequence encoding the inert portion of the PTR linker may be located after the nucleic acid sequence encoding the small fragment of the split fluorescent protein (or before as shown in FIG. 5) (closer to the C-terminus of the translated small fragment of the split fluorescent protein than in the example of FIG. 5).

The amino acid sequences corresponding to SEQ ID. NO. ID NO: 1-39 presented herein may be considered artificial sequences for the purpose of sequence listings.

Definitions

In the present disclosure, by "cleave" or "cleaving", it is meant fragmenting or separating a peptide encoded by a specific nucleic acid sequence, via, for instance, a lyase, or during translation as a result of the behaviour of the ribosome (e.g., ribosomal skipping and failing to create a peptide bond to generate two separate proteins).

In the present disclosure, by "fluorescent protein", it is meant a protein that is self-sufficient to form a visible wavelength chromophore from a sequence of amino acids. Fluorescent proteins can be used to measure expression of a protein of interest in cells, using for instance, fluorescence microscopy. An exemplary fluorescent protein is green fluorescent protein derived from *Aequorea victoria*. As such, measuring fluorescence allows for reporting the expression, and the level of expression, of a protein of interest. The fluorescent protein may generate different wavelengths, such as green, red, yellow, etc. Moreover, a fluorescent protein can be expressed in fragments in a cell (i.e. split), where the fragments can combine to form the fluorescent protein, thereby generating fluorescence. Exemplary amino acid sequences, and corresponding nucleic acid sequences, for these parts, will be described in the present disclosure.

In the present disclosure, by "host cell" or "cell", it is meant an in-vitro, in-vivo or ex-vivo cell that can be studied for the purpose of quantifying the expression of a protein of interest as described herein. The cell may be a eukaryotic cell such as mammalian cells (such as human cells, rodent cells), other animal cells (such as fish cells, amphibian cells, insect cells, worm cells), plant cells, algal cells, fungal cells (such as yeast cells and mold cells). A cell may be, for instance, a neuron, requiring real-time reporting and quantification of translation in order to address the rapid protein diffusion across the cell(s), or a heterologous cell line used to assay and quantify effects of therapeutic drugs during drug discovery and screening.

In the present disclosure, by "inert portion", when referring to the PTR linker when it is composed of a PQR portion and an inert portion, it is meant a small peptide that is part of the PTR linker as described herein. The inert portion may be located after the PQR portion (between the PQR portion and the small fragment of the split fluorescent protein), or after the small fragment of the split fluorescent protein.

In the present disclosure, by "nucleic acid sequence", it is meant a ribonucleic acid (RNA) molecule, a deoxyribonucleic acid (DNA) molecule, or a molecule that is a combination of RNA and DNA.

In the present disclosure, by "protein of interest", it is meant a protein that is the subject of quantification, where its expression is to be measured or estimated. The nucleic acid sequence of the protein of interest is connected to the nucleic acid of the PTR linker.

In the present disclosure, by "PQR linker", it is meant a protein linker, or its corresponding nucleic acid sequence, as described in U.S. 2019/0032154, that connects a protein of interest and a reporter protein, that can be cleaved during translation to provide a separate protein of interest and a reporter protein with a given stoichiometric ratio.

In the present disclosure, by "PQR portion", it is meant a portion of the PTR linker that connects the protein of interest and the small fragment of the split fluorescent protein when the PTR linker includes both a PQR portion and an inert portion. In some embodiments, the PQR portion may correspond to the PQR linker as described in U.S. 2019/0032154.

In the present disclosure, by "PTR linker" or "protein translation reporter linker", it is meant a peptide that is cleaved or causes a split during protein translation, thereby resulting in at least two separated peptide portions. The nucleic acid sequence of the PTR linker interconnects the nucleic acid sequence of a protein of interest and the nucleic acid sequence of the small fragment of the split fluorescent protein. As such, when the PTR linker is cleaved during translation by, e.g., the ribosome, this results in separation of the translated small portion of the fluorescent protein from the translated protein of interest. When the present disclosure refers to the PTR linker interconnecting the protein of interest to a small portion of the fluorescent protein, this language is used for the purpose of simplicity as the PTR linker may be cleaved during translation, thereby cleaved prior to translation of either the small fragment of the split fluorescent protein or the protein of interest, as the nucleic acid sequence encoding the PTR linker is between the nucleic acid sequence encoding the small fragment of the split fluorescent protein and the nucleic acid sequence encoding the protein of interest. As such, the PTR linker may be cleaved prior to either the small fragment of the split fluorescent protein or the protein of interest being translated. Exemplary sequences of the PTR linker, and its corresponding nucleic acid sequence(s), are described herein.

In the present disclosure, by "split fluorescent protein", it is meant a fluorescent protein that is expressed in a cell in parts, where the expressed parts are combinable to constitute the entire fluorescent protein, thereby producing fluorescence. For instance, in the example of protein quantification using PTR linkers, a small portion of the fluorescent protein may be expressed from the nucleic acid sequence that is joined to the nucleic acid sequence of the PTR linker. The cell may already express the remaining large portion of the split fluorescent protein (e.g. having been previously transfected with the corresponding nucleic acid sequence).

In the present disclosure, by "stoichiometric ratio", it is meant the ratio between the different products following a reaction or action. For instance, when a nucleic acid molecule encodes one unit of a protein of interest and one unit of a small fragment of a fluorescent protein, the stoichiometric ratio resulting from the action of protein translation between the protein of interest and the small portion of the fluorescent protein is 1:1.

In the present disclosure, by "transfecting", it is meant the process of deliberately introducing nucleic acids into a eukaryotic cell.

In the present disclosure, by "vector", it is meant a nucleic acid molecule used as a vehicle to carry foreign genetic material into a cell, where the nucleic acid molecule can be replicated and/or expressed. Exemplary vectors include, but are not limited to, plasmids, viral vectors, cosmids, artificial chromosomes, single-stranded donor oligonucleotides (ssODN), etc. Vectors may be circular or linear. A vector may include one or more proteins of interest, one or more PTR linkers, one or more small fragments of one or more split fluorescent proteins. A vector may also be used to transfect a cell with the nucleic acid sequence encoding the large portion of the split fluorescent protein.

Exemplary Split Fluorescent Proteins:

Split fluorescent proteins are fragments of fluorescent proteins that associate (e.g. spontaneously) to form the fluorescent protein and that then fluoresce.

With reference to the protein quantification ratioing as described herein, the nucleic acid sequence encoding a fragment (e.g. the smaller fragment) of the split fluorescent protein is joined to the nucleic acid encoding the PTR linker. However, it will be apparent to the skilled person that the split fluorescent proteins can be used for other procedures.

It is apparent to the skilled person that the protein quantification ratioing described utilizing a PTR linker can involve any split fluorescent protein for providing fluorescence when the fragments of the split fluorescent protein associate, where the nucleic acid sequence encoding the small fragment of the split fluorescent protein may be joined to the nucleic acid sequence encoding the PTR linker. Table 1 presents an exemplary list of amino acid sequences for both fragments of different exemplary split fluorescent proteins, that can be used in association with the protein quantifying methods described herein. The sequences presented in Table 1 are for illustrative purposes only, and it will be understood that other sequences of split fluorescent proteins may also be used for the protein quantification ratioing with a PTR linker, as described herein, without departing from the present teachings.

TABLE 1 amino acid sequences of exemplary fragments of split fluorescent proteins

| Name | Amino Acid Sequence Listing | SEQ ID. NO. |
|---|---|---|
| GFP1-10 (large fragment of GFP) | MSKGEELFTGVVPILVELDGDVNGHKFSVRGEGEGDATIG KLTLKFICTTGKLPVPWPTLVTTLTYGVQCFSRYPDHMKR HDFFKSAMPEGYVQERTISFKDDGKYKTRAVVKFEGDTLV NRIELKGTDFKEDGNILGHKLEYNFNSHNVYITADKQKNGI KANFTVRHNVEDGSVQLADHYQQNTPIGDGPVLLPDNHY LSTQTVLSKDPNEKGT* | 1 |
| GFP1-10 (large fragment of GFP) | MSKGEELFTGVVPILVELDGDVNGHKFSVRGEGEGDATIG KLTLKFICTTGKLPVPWPTLVTTLTYGVQCFSRYPDHMKR HDFFKSAMPEGYVQERTISFKDDGKYKTRAVVKFEGDTLV NRIELKGTDFKEDGNILGHKLEYNFNSHNVYITADKQKNGI KANFTVRHNVEDGSVQLADHYQQNTPIGDGPVLLPDNHY LSTQTVLSKDPNEK* | 2 |
| GFP11 (small fragment of GFP) | MRDHMVLLEFVTAAGIT* | 3 |
| GFP11 (small fragment of GFP) | MRDHMVLLEFVTAAGIT* | 4 |
| GFP11 (small fragment of GFP) | MRDHMVLHEFVTAAGIT* | 5 |
| GFP11 (small fragment of GFP) | MRDHMVLHEFVTAAGIT* | 6 |
| GFP11 (small fragment of GFP) | MRDHMVLHEYVNAAGIT* | 7 |
| Dendra1-10 (large fragment) | MNTPGINLIKEDMRVKVHMEGNVNGHAFVIEGEGKGKPY EGTQTANLTVKEGAPLPFSYDILTTAVHYGNRVFTKYPEDI PDYFKQSFPEGYSWERTMTFEDKGICTIRSDISLEGDCFF QNVRFKGTNFPPNGPVMQKKTLKWEPSTEKLHVRDGLLV GNINMALLLEGGGHYLCDFKTTYKAKKVVQLPDAHFVDHR IEILGNDSDYNKVKLYEHAVARYSPLPSQVW* | 8 |
| Dendra11 (small fragment) | MPDAHFVDHRIEILGNDSDYNKVKLYEHAVARYSPLPSQV W* | 9 |
| Cherry1-10 (large fragment) | MEEDNMAIIKEFMRFKVHMEGSVNGHEFEIEGEGEGHPY EGTQTAKLKVTKGGPLPFAWDILSPQFMYGSKAYVKHPA DIPDYLKLSFPEGFTWERVMNFEDGGVVTVTQDSSLQDG EFIYKVKLLGTNFPSDGPVMQKKTMGWEASTERMYPEDG ALKGEINQRLKLKDGGHYDAEVKTTYKAKKPVQLPGAYNV DIKLDITSHNED* | 10 |

TABLE 1-continued amino acid sequences of exemplary fragments of split fluorescent proteins

| Name | Amino Acid Sequence Listing | SEQ ID. NO. |
|---|---|---|
| Cherry11 (small fragment) | MYTIVEQYERAEGRHSTGG* | 11 |
| Cherry11 (small fragment) | MYTIVEQYERAEARHST* | 12 |

It will be understood that, for a given fluorescent protein whose sequence is listed in Table 1, any amino acid sequence of a large fragment of a given type can be associated with the amino acid sequence of the small fragment of the given type. For instance, SEQ ID NO: 1 or SER ID NO: 2 can be associated with any one of SEQ ID. NO: 3-7. SEQ ID NO: 10 can be associated with SEQ ID NO: 11 or 12.

The location for splitting a fluorescent protein can be determined as a function of the structure of the protein once folded, e.g. based on the beta-sheets, beta-strands and/or alpha-helices of the fluorescent protein, where the splitting can take place such that one of these structures forms the small fragment, and the remainder of the protein forms the large fragment.

Table 2 lists exemplary DNA sequence listings, from 5' to 3', that can encode the amino acid sequences listed in Table 1.

TABLE 2

DNA sequences corresponding to the fluorescent protein fragment amino acid sequences of Table 1.

| Name | DNA SEQUENCE LISTING | Corresponding SEQ ID. NO. of the encoded peptide sequence | SEQ ID. NO. |
|---|---|---|---|
| GFP1-10 (large fragment of GFP) | ATGTCCAAGGGAGAAGAGTTGTTTACTGGCGTAGTC CCTATTCTCGTGGAACTCGATGGTGACGTGAATGG CCATAAGTTTTCTGTCAGAGGAGAGGGAGAAGGCG ATGCCACCATCGGGAAACTCACGCTGAAATTCATCT GTACCACTGGAAAACTTCCCGTGCCTTGGCCAACC CTCGTGACAACACTCACCTACGGGGTGCAATGTTTC TCTCGGTACCCGGACCATATGAAGAGGCATGACTT CTTCAAGAGTGCCATGCCCGAGGGTTACGTTCAGG AGCGCACCATCTCTTTTAAGGACGATGGCAAATATA AGACAAGAGCAGTCGTCAAGTTCGAGGGTGATACA CTCGTTAACCGCATCGAGCTCAAAGGCACCGATTTT AAGGAGGACGGAAATATCCTGGGACACAAATTGGA GTACAACTTCAACAGTCACAACGTGTATATTACAGC AGATAAGCAGAAGAATGGCATAAAGGCCAATTTCAC GGTAAGACATAATGTCGAGGATGGCAGTGTCCAGC TGGCAGACCACTACCAGCAAAACACGCCCATTGGC GATGGACCTGTTCTCCTGCCAGACAACCACTACCTC AGTACCCAAACAGTCCTGTCCAAGGACCCTAATGAG AAAGGGACGTGA | 1 | 13 |
| GFP1-10 (large fragment of GFP) | ATGTCCAAAGGAGAAGAACTGTTTACCGGTGTTGTG CCAATTTTGGTTGAACTCGATGGTGATGTCAACGGA CATAAGTTCTCAGTGAGAGGCGAAGGAGAAGGTGA CGCCACCATTGGAAAATTGACTCTTAAATTCATCTGT ACTACTGGTAAACTTCCTGTACCATGGCCGACTCTC GTAACAACGCTTACGTACGGAGTTCAGTGCTTTTCG AGATACCCAGACCATATGAAAAGACATGACTTTTTA AGTCGGCTATGCCTGAAGGTTACGTGCAAGAAAGA ACAATTTCGTTCAAAGATGATGGAAAATATAAAACTA GAGCAGTTGTTAAATTTGAAGGAGATACTTTGGTTA ACCGCATTGAACTGAAAGGAACAGATTTTAAAGAAG ATGGTAATATTCTTGGACACAAACTCGAATACAATTT TAATAGTCATAACGTATACATCACTGCTGATAAGCAA AAGAACGGAATTAAAGCGAATTTCACAGTACGCCAT AATGTAGAAGATGGCAGTGTTCAACTTGCCGACCAT TACCAACAAAACACCCCTATTGGAGACGGTCCGGTA CTTCTTCCTGATAATCACTACCTCTCAACACAAACAG TCCTGAGCAAAGATCCAAATGAAAAATGA | 2 | 14 |

TABLE 2-continued

DNA sequences corresponding to the fluorescent protein fragment amino acid sequences of Table 1.

| Name | DNA SEQUENCE LISTING | Corresponding SEQ ID. NO. of the encoded peptide sequence | SEQ ID. NO. |
|---|---|---|---|
| GFP1 1 (small fragment of GFP) | ATG CGA GAC CAC ATG GTC TTG CTT GAA TTC GTA ACA GCA GCG GGG ATC ACT TGA | 3 | 15 |
| GFP11 (small fragment of GFP) | ATG AGG GAC CAC ATG GTC CTC CTG GAA TTC GTA ACC GCA GCC GGT ATC ACC TGA | 4 | 16 |
| GFP11 (small fragment of GFP) | ATG CGT GAC CAT ATG GTG TTG CAC GAG TTC GTC ACC GCT GCT GGT ATC ACC TGA | 5 | 17 |
| GFP11 (small fragment of GFP) | ATG AGA GAT CAT ATG GTT CTC CAC GAG TTC GTA ACT GCA GCT GGG ATC ACT TGA | 6 | 18 |
| GFP11 (small fragment of GFP) | ATGGTGACCACATGGTCCTCCATGAGTACGTTAATG CTGCGGGCATCACC TAA | 7 | 19 |
| GFP11 (small fragment of GFP) | ATG CGA GAC CAC ATG GTG CTG CAT GAG TAC GTC AAC GCA GCC GGT ATT ACG TAA | 7 | 20 |
| Dendra1-10 (large fragment) | ATGAACACCCCGGGAATTAACCTGATCAAGGAGGA CATGCGCGTGAAGGTGCACATGGAGGGCAACGTGA ACGGCCACGCCTTCGTGATCGAGGGCGAGGGCAA GGGCAAGCCCTACGAGGGCACCCAGACCGCCAAC CTGACCGTGAAGGAGGGCGCCCCCCTGCCCTTCAG CTACGACATCCTGACCACCGCCGTGCACTACGGCA ACCGGGTGTTCACCAAGTACCCCGAGGACATCCCC GACTACTTCAAGCAGAGCTTCCCCGAGGGCTACAG CTGGGAGCGCACCATGACCTTCGAGGACAAGGGCA TCTGCACCATCCGCAGCGACATCAGCCTGGAGGGC GACTGCTTCTTCCAGAACGTGCGCTTCAAGGGCAC CAACTTCCCCCCCAACGGCCCCGTGATGCAGAAGA AGACCCTGAAGTGGGAGCCCAGCACCGAGAAGCTG CACGTGCGCGACGGCCTGCTGGTGGGCAACATCAA CATGGCCCTGCTGCTGGAGGGCGGCGGCCACTAC CTGTGCGACTTCAAGACCACCTACAAGGCCAAGAA GGTGGTGCAGCTGCCCGACGCCCACTTCGTGGACC ACCGCATCGAGATCCTGGGCAACGACAGCGACTAC AACAAGGTGAAGCTGTACGAGCACGCCGTGGCCCG CTACAGCCCCCTGCCCAGCCAGGTGTGGTAA | 8 | 21 |
| Dendra11 (small fragment) | ATGCCCGACGCCCACTTCGTGGACCACCGCATCGA GATCCTGGGCAACGACAGCGACTACAACAAGGTGA AGCTGTACGAGCACGCCGTGGCCCGCTACAGCCCC CTGCCCAGCCAGGTGTGGTGA | 9 | 22 |
| Cherry1-10 (large fragment) | ATGGAGGAGGACAACATGGCCATCATCAAGGAGTT CATGAGATTCAAGGTGCACATGGAGGGCAGCGTGA ACGGCCACGAGTTCGAGATCGAGGGCGAGGGCGA GGGCCACCCCTACGAGGGCACCCAGACCGCCAAG CTGAAGGTGACCAAGGGCGGCCCCCTGCCCTTCGC CTGG GACATCCTGAGCCCCCAGTTCATGTACGGCAGCAA GGCCTACGTGAAGCACCCCGCCGACATCCCCGACT ACCTGAAGCTGAGCTTCCCCGAGGGCTTCACCTGG GAGAGAGTGATGAACTTCGAGGACGGCGGCGTGGT GACCGTGACCCAGGACAGCAGCCTGCAGGACGGC GAG | 10 | 23 |

TABLE 2-continued

DNA sequences corresponding to the fluorescent protein fragment amino acid sequences of Table 1.

| Name | DNA SEQUENCE LISTING | Corresponding SEQ ID. NO. of the encoded peptide sequence | SEQ ID. NO. |
|---|---|---|---|
| | TTCATCTACAAGGTGAAGCTGCTGGGCACCAACTTC<br>CCCAGCGACGGCCCCGTGATGCAGAAGAAGACCAT<br>GGGCTGGGAGGCCAGCACCGAGAGAATGTACCCC<br>GAGGACGGCGCCCTGAAGGGCGAGATCAACCAGA<br>GACTGAAGCTGAAGGACGGCGGCCACTACGACGC<br>CGAGGTGAAGACCACCTACAAGGCCAAGAAGCCCG<br>TGCAGCTGCCCGGCGCCTACAACGTGGACATCAAG<br>CTGGACATCACCAGCCACAACGAGGACTGA | | |
| Cherry11 (small fragment) | ATGTACACCATCGTGGAGCAGTACGAGAGAGCCGA<br>GGGCAGACACAGCACCGGCGGCTGA | 11 | 24 |
| Cherry11 (small fragment) | ATGTACACCATCGTGGAGCAGTACGAGAGAGCCGA<br>GGCCAGACACAGCACCTGA | 12 | 25 |

Either SEQ ID NO: 19 or 20 can encode the amino acid sequence corresponding to SEQ ID NO: 7.

Exemplary PTR Linkers:

The present disclosure also relates to PTR linkers that interconnect the small fragment of a split fluorescent protein and a protein of interest (for quantification). The PTR linkers yield improved translation of the small fragment of the split fluorescent protein when compared to the PQR linkers of U.S. 2019/0032154.

The PTR linker is composed of a PQR portion and an inert portion. The nucleic acid sequence encoding the inert portion can either be placed between the nucleic acid sequence encoding the PQR portion and the nucleic acid sequence encoding the small fragment of the fluorescent protein, or can be placed after the nucleic acid sequence encoding the small fragment of the fluorescent protein, the nucleic acid sequence encoding the small fragment of the fluorescent protein joined to the nucleic acid sequence encoding the PQR portion. As such, the PTR linker, both the PQR portion and the inert portion, may be uninterrupted, or may be separated by the small fragment of the split fluorescent protein, the small fragment of the split fluorescent protein flanked on either side by the PQR portion and the inert portion.

Table 3 illustrates exemplary amino acid sequences of the PQR portion of the PTR linker. It will be understood that the amino acid sequence presented in Table 3 are but exemplary, and that other amino acid sequences of the PQR portion, including those found in U.S. 2019/0032154, can be used as the PQR portion.

TABLE 3 exemplary amino acid sequences of the PQR portion of the PTR linker.

| # | Amino Acid Sequence | SEQ ID. No. |
|---|---|---|
| 1 | GSGATNFSLLKQAGDVEENPGP | 26 |
| 2 | GSGATNFSLLKQAGDVEENPGP | 27 |

In some embodiments, the PTR linker may include one or more additional amino acids to which is found upstream (from the N-terminus) to those listed in Table 3.

Table 4 lists exemplary DNA sequence listings, from 5' to 3', that can encode the amino acid sequences listed in Table 3.

TABLE 4

DNA sequences corresponding to the PQR portion amino acid sequences of Table 3.

| # | DNA SEQUENCE LISTING | Corresponding SEQ ID. NO. of the encoded peptide sequence | SEQ ID. NO. |
|---|---|---|---|
| 1 | GGAAGCGGAGCGACGAATTTTAGTCTACTAAAA<br>CAAGCGGGTGATGTAGAAGAAAACCCTGGACCT | 26 | 28 |
| 2 | GGAAGCGGAGCGACGAATTTTAGTCTACTGAAA<br>CAAGCGGGAGACGTGGAGGAAAACCCTGGACC<br>T | 27 | 29 |

The inert portion of the PTR linker can be a small peptide composed of non-bulky amino acids that do not have a significant impact on the charge or solubility of the peptide to which it is attached. These characteristics are sought in order to reduce any impact that the small peptide may have on the function and structure of the peptide to which the inert portion is attached after translation. As such, the nucleic acid sequence of the small fragment may be defined such that it leads to an inert portion peptide that possesses these characteristics. Exemplary amino acids that can compose the inert portion of the PTR linker may include Glycine (G), Serine (S), Valine (V), Aspartate (D), Glutamate (E), Alanine (A), Lysine (K) and Proline (P).

Moreover, it has been discovered that the length of the nucleic acid sequence encoding the inert portion preferably has a minimal length that may encode at least 5 amino acids. Additionally, the inert portion expressed from the corresponding nucleic acid sequence may preferably not be of a length that may risk affecting the structure and function of the small fragment of the split fluorescent protein to which it is attached. As such, the length of the inert portion of the PTR linker may preferably not include more than 20 amino acids, and more preferably not more than 15 amino acids. Therefore, in some embodiments, the length of the inert portion of the PTR linker may vary between 5 to 15 amino acids (or between 5 to 20 amino acids), and its nucleic acid sequence is adapted to encode an inert portion having a length between 5 to 15 amino acids (or respectively between 5 to 20 amino acids).

For instance, an exemplary amino acid sequence for an inert portion may be:
(SEQ. ID NO: 36)
$X_1 X_2 X_3 X_4 X_5 X_6 X_7 X_8 X_9 X_{10} X_{11} X_{12} X_{13} X_{14} X_{15} X_{16} X_{17} X_{18} X_{19} X_{20}$,
where $X_1$ to $X_5$ may be G, S, V, D, E, A, K, or P, and where $X_6$ to $X_{20}$ may be G, S, V, D, E, A, K, or P or absent.
Another exemplary amino acid sequence for an inert portion may be:
(SEQ ID NO: 37)
$X_1 X_2 X_3 X_4 X_5 X_6 X_7 X_8 X_9 X_{10} X_{11} X_{12} X_{13} X_{14} X_{15}$,
where $X_1$ to $X_5$ may be G, S, V, D, E, A, K, or P, and where $X_6$ to $X_{15}$ may be G, S, V, D, E, A, K, or P or absent.

Yet another exemplary amino acid sequence for an inert portion may be:
(SEQ. ID NO: 38)
$X_1 X_2 X_3 X_4 X_5 X_6 X_7 X_8 X_9 X_{10} X_{11} X_{12} X_{13} X_{14} X_{15} X_{16} X_{17} X_{18} X_{19} X_{20}$,
where $X_1$ to $X_5$ may be G, S, V or D, and where $X_6$ to $X_{20}$ may be G, S, V, D or absent.
Another exemplary amino acid sequence for an inert portion may be:
(SEQ ID NO: 39)
$X_1 X_2 X_3 X_4 X_5 X_6 X_7 X_8 X_9 X_{10} X_{11} X_{12} X_{13} X_{14} X_{15}$,
where $X_1$ to $X_5$ may be G, S, V or D, and where $X_6$ to $X_{20}$ may be G, S, V, D or absent.

The nucleic acid sequences encoding each of the amino acid sequences 36-39 include the codons that encode the selected amino acids of the amino acid sequences, the correspondence between the codons and the amino acid sequences being known in the art.

Table 5 illustrates exemplary amino acid sequences corresponding to the inert portion of the PTR linker, that meet the characteristics defined herein for the inert portion of the PTR linker. It will be understood that the amino acid sequences presented in Table 5 are but illustrative of the inert portion described herein, and that other amino acid sequences corresponding to the inert portion may be achieved in accordance with the present teachings.

TABLE 5 amino acid sequences of exemplary inert portions of the PTR linker.

| # | Amino Acid Sequence | SEQ ID. No. |
|---|---|---|
| 1 | GGGSGGGSVD | 30 |
| 2 | GGGGSGGGGSVD | 31 |
| 3 | GGGGSGGGGSVD | 32 |
| 4 | GGGGSGGGGSVD | 33 |
| 5 | GGGGSGGGGS | 34 |
| 6 | GGGSGGGS | 35 |
| 7 | EAAAK | 52 |
| 8 | PPPPP | 53 |

Table 6 presents an exemplary list of organism-based nucleic acid sequences (DNA sequences) that encode the peptide sequences listed in Table 5. It will be understood that other DNA sequences may encode the peptide sequences of Table 5, depending on the organism and the codons, without departing from the present teachings.

TABLE 6

DNA sequences corresponding to the inert portion amino acid sequences of Table 3.

| Organism | DNA SEQUENCE LISTING | Corresponding SEQ ID. NO. of the encoded peptide sequence | SEQ ID. NO. |
|---|---|---|---|
| Human | GGC GGC GGC AGC GGC GGC GGC AGC GTG GAC | 30 | 40 |
| Mouse | GGC GGC GGC AGC GGC GGC GGC AGC GTG GAC | 30 | 41 |
| Fly | GGC GGC GGC TCC GGC GGC GGC TCC GTG GAC | 30 | 42 |
| Human | GGC GGC GGC GGC AGC GGC GGC GGC GGC AGC GTG GAC | 31 | 43 |

TABLE 6-continued

DNA sequences corresponding to the inert portion amino acid sequences of Table 3.

| Organism | DNA SEQUENCE LISTING | Corresponding SEQ ID. NO. of the encoded peptide sequence | SEQ ID. NO. |
|---|---|---|---|
| Mouse | GGC GGC GGC GGC AGC GGC GGC GGC GGC AGC GTG GAC | 31 | 44 |
| Fly | GGC GGC GGC GGC TCC GGC GGC GGC GGC TCC GTG GAC | 31 | 45 |
| Human | GGC GGC GGC GGC AGC GGC GGC GGC GGC AGC GTG GAC | 32 | 43 |
| Mouse | GGC GGC GGC GGC AGC GGC GGC GGC GGC AGC GTG GAC | 32 | 44 |
| Fly | GGC GGC GGC GGC TCC GGC GGC GGC GGC TCC GTG GAC | 32 | 45 |
| Human | GGC GGC GGC GGC AGC GGC GGC GGC GGC AGC GTG GAC | 33 | 43 |
| Mouse | GGC GGC GGC GGC AGC GGC GGC GGC GGC AGC GTG GAC | 33 | 44 |
| Fly | GGC GGC GGC GGC TCC GGC GGC GGC GGC TCC GTG GAC | 33 | 45 |
| Human | GGC GGC GGC GGC AGC GGC GGC GGC GGC AGC | 34 | 46 |
| Mouse | GGC GGC GGC GGC AGC GGC GGC GGC GGC AGC | 34 | 47 |
| Fly | GGC GGC GGC GGC TCC GGC GGC GGC GGC TCC | 34 | 48 |
| Human | GGC GGC GGC AGC GGC GGC GGC GGC AGC | 35 | 49 |
| Mouse | GGC GGC GGC AGC GGC GGC GGC GGC AGC | 35 | 50 |
| Fly | GGC GGC GGC TCC GGC GGC GGC GGC TCC | 35 | 51 |
| Human | GAA GCC GCT GCA AAG | 52 | 54 |
| Mouse | GAA GCA GCC GCT AAG | 52 | 55 |
| Fly | GAG GCC GCA GCC AAA | 52 | 56 |
| Human | CCT CCT CCC CCT CCT | 53 | 57 |
| Mouse | CCC CCT CCC CCC CCT | 53 | 58 |
| Fly | CCC CCG CCG CCG CCA | 53 | 59 |

Moreover, in some examples where the inert portion of the PTR linker is found downstream from the small fragment of the split fluorescent protein, an additional small peptide (e.g. of less than 40 amino acids), preferable inert, may be located between the PQR portion of the PTR linker and the small fragment of the split fluorescent protein without having a material effect on translation.

In some examples, the inert portion may be composed of repeating peptide sequences (sub-units of peptide sequences). For instance, Table 7 lists non-limitative exemplary peptide sequences of sub-units that can be repeated, resulting in an inert portion of the PTR linker:

TABLE 7 amino acid sequences of exemplary sub-units that compose inert portions of the PTR linker.

| # | Amino Acid Sequence | SEQ ID. No. |
|---|---|---|
| 9 | EAAAK | 60 |
| 10 | GGGGS | 61 |

For instance, an inert portion may be composed of different combinations and repetitions of the amino acid sequences corresponding to SEQ ID NO: 9 and 10. For instance, the inert portion may be composed of "n" subunits corresponding to SEQ ID NO: 9 followed by "m" subunits corresponding to SEQ ID NO: 10. For instance, the inert portion may be composed of "n" subunits corresponding to SEQ ID NO: 10 followed by "m" subunits corresponding to SEQ ID NO: 9. "m" and "n" are integers ranging from 0 to 4, where the minimum amount of amino acids of the inert portion is 5, and the maximum amount of amino acids of the inert portion is 20. In some examples, the sub-units corresponding to SEQ ID NO: 9 and 10 may interchange (e.g. one subunit corresponding to SEQ ID NO: 9, followed by one subunit corresponding to SEQ ID NO: 10, followed by one subunit corresponding to SEQ ID NO: 10).

Table 8 lists exemplary DNA sequences that encode the amino acid sequences of Table 7, the DNA sequences presented in accordance with the targeted organism. It will be understood that other DNA sequences may encode the peptide sequences of Table 7, depending on the organism and the codons, without departing from the present teachings.

TABLE 8

DNA sequences corresponding to the sub-units of the inert portion amino acid sequences of Table 7.

| Organism | DNA SEQUENCE LISTING | Corresponding SEQ ID. NO. of the encoded peptide sequence | SEQ ID. NO. |
|---|---|---|---|
| Human | GAA GCC GCT GCA AAG | 60 | 62 |
| Mouse | GAA GCA GCC GCT AAG | 60 | 63 |
| Fly | GAG GCC GCA GCC AAA | 60 | 64 |
| Human | GGT GGA GGC GGT TCC | 61 | 65 |
| Mouse | GGA GGT GGC GGG AGC | 61 | 66 |
| Fly | GGC GGT GGC GGT AGT | 61 | 67 |

Moreover, in some examples where the inert portion of the PTR linker is found downstream from the PQR portion of the PTR linker yet upstream from the small fragment of the split fluorescent protein, an additional peptide of less than 40 amino acids may be located between the PTR linker and the small fragment of the split fluorescent protein without having a material effect on translation.

Vector Comprising the PTR Linker

The nucleic acid sequence for the PTR linker can be presented in the form of a vector which is at least designed to also encode the active portion of the fluorescent protein and a protein of interest. In the methods described herein, the PTR linker is intended to be located between the two proteins, i.e., between a protein of interest and the small fragment of the split fluorescent protein.

In its simplest embodiment, the vector comprises the nucleic acid encoding the PTR linker and is designed to allow for the integration of the nucleic acid sequence encoding the portion of the fluorescent protein and the nucleic acid sequence encoding the protein of interest on each side of the nucleic acid encoding the PTR linker. The vector is designed to allow for the transcription of a mRNA encoding the entire poly-protein sequence. In an embodiment, the nucleic acid sequence encoding the small portion of the fluorescent protein can be configured to be located upstream of the nucleic acid encoding the PTR linker, and the nucleic acid sequence encoding the protein of interest is intended to be located downstream of the nucleic acid encoding the PTR linker. Alternatively, the nucleic acid sequence encoding the portion of the fluorescent protein can be intended to be located downstream of the nucleic acid encoding the PTR linker, while the nucleic acid sequence encoding the protein of interest can be intended to be located upstream of the nucleic acid sequence encoding the PTR linker.

In another embodiment, the vector can include both the nucleic acid sequence encoding the PTR linker and the nucleic acid sequence encoding the small portion of the fluorescent protein. In this embodiment, the end-user is provided with a customizable vector in which the nucleic acid sequence encoding the protein of interest can be inserted and used.

In another embodiment, the vector can include both the nucleic acid sequence encoding the PTR linker and the nucleic acid sequence encoding the protein of interest. In this embodiment, the end-user is provided with a customizable vector in which the nucleic acid sequence encoding the small portion of the fluorescent protein can be inserted and used.

In yet another embodiment, the vector can include the nucleic acid sequence encoding the PTR linker, the nucleic acid sequence encoding the protein of interest and the nucleic acid sequence encoding the small fragment of the split fluorescent protein. In this embodiment, the end-user is provided with a ready-to-use vector to quantify a specific protein of interest.

In some embodiments, the vector can be a linear vector or a circular vector. The vector can also be an integratable vector and as such can comprise a nucleic acid sequence capable of favoring or allowing integration of the vector in the genome of the host cell. In such embodiment, once integrated, some of the sequence of the original vector may have been removed during integration. In another embodiment, the vector can replicate independently from the host genome and as such can comprise a suitable origin of replication. The vector can also include a further nucleic acid molecule encoding a selection marker protein to identify host cells bearing the vector from those not bearing the vector.

In some embodiments, the vector can be designed to be integrated in the host's genome either in an unspecific or a specific manner (e.g., using the CRISPR/Cas9 system).

The vector can be any vector suitable for expressing the mRNA encoding the poly-protein. For example, the vector can be derived from a virus (e.g., retrovirus, adenovirus, herpes or vaccinia), from a yeast (e.g., an artificial chromosome or cosmid), from a bacteria (e.g., a bacterial plasmid for example), or from a wholly synthetic sequence.

The present disclosure also provides for a kit for performing protein quantification using the vector described herein. The kit may include the vector described herein and instructions on how to use the vector to quantify the protein of interest. For example, the instructions can indicate how to introduce the nucleic acid sequence encoding the small portion of the fluorescent protein, how to introduce the nucleic acid sequencing encoding the protein of interest in the vector, how to introduce the vector in a host cell, how to integrate the vector into the genome, how to select for host cell bearing the vector, how to measure the signal from the cleaved reporter protein, etc. The kit can also provide a control vector and instructions on how to use the control vector to quantify the protein of interest. The kit can further provide a host cell or a host organism. For instance, the host organism may already be engineered to express the large portion of the protein of interest. The cells of the organism can then be transfected with the vector, such that protein translation of, e.g. the mRNA transcribed from the vector is the vector is DNA, causes the expression of the small portion of the fluorescent protein, the small portion of the fluorescent protein bonding with the large portion of the fluorescent protein already expressed by the organism, thereby causing fluorescence.

The organism may include eukaryotic cells include mammalian cells (such as human cells, rodent cells), other animal cells (such as fish cells, amphibian cells, insect cells, worm cells), plant cells, algal cells, fungal cells (such as yeast cells and mold cells).

Method for Quantifying Proteins in Host Cells

The present disclosure also provides for a method of quantifying a protein of interest in a host cell. The protein can be measured in vitro (when the host cell can be maintained in in vitro conditions), in vivo (when the host cell is located in a multicellular organism) or ex vivo (when the host cell is removed from a multicellular organism). In some embodiments, the protein can be measured in living cells. In some embodiments, the protein can be measured at the single-cell level.

A host cell is provided that expresses the large fragment of the split fluorescent protein, the large fragment the split fluorescent protein requiring the small fragment of the split fluorescent protein to fluoresce. The provided host cell does not express the small fragment of the split fluorescent protein and does not fluoresce. In some examples, these host cells expressing the large fragment of the split fluorescent protein may be provided in an organism (e.g. a transgenic mouse), where the organism has been genetically modified (e.g. through transfection) to express the large fragment of the split fluorescent protein.

The vector encoding the poly-protein (which includes the PTR linker) is expressed in the host cell. Expression of the poly-protein can be driven from regulatory sequences present in the vector, upstream or downstream, of the poly-protein. Alternatively, expression of the poly-protein can be driven from endogenous regulatory sequences present in the host's genome by integrating the poly-protein specifically in the host's genome. The method can be practiced on any eukaryotic host cell which can transcribe the nucleic acid sequence of the poly-protein in a poly-cistronic nucleic acid transcript and translate the resulting nucleic acid transcript. Without limitation, for instance, the host cell can be a mammalian (such as a human), a plant, an insect, a yeast, a mold, and/or an algae.

The method can be designed to accommodate the quantification of more than one protein of interest. In order to do so, more than one PTR and small portion of the fluorescent protein are encoded on the same vector or more than one vector is transferred inside the host cell.

Once the nucleic acid transcript associated with the poly-protein is expressed, the equivalent expressed protein can be cleaved during translation to generate, at a stoichiometric ratio (and in some embodiment, in an equimolar ratio), a cleaved small-portion of the split fluorescent protein and a cleaved protein of interest. As such, the host cell now expresses both the small fragment of the split fluorescent protein (now separated from the protein of the interest) and the large fragment of the split fluorescent protein. As the small fragment, due to its dimensions, undergoes folding rapidly, it is free to bond with the large fragment of the split fluorescent protein (already folded and matured) shortly after translation.

The translated small fragment of the split fluorescent protein then bonds with the large fragment of the split fluorescent protein found in the cell, forming the complete fluorescent protein, generating a fluorescent signal. The fluorescent signal can then be measured to provide an indication of or quantify the amount of the protein of interest. The measure of the signal can be repeated in time or conducted only once. Background fluorescence can be subtracted in order to improve signal quality as is known in the art.

Once the signal associated with the reporter protein has been obtained, it is used to estimate the amount of the protein of interest. For example, the signal can be graphically compared to a standard curve associating the fluorescence to the amount of the protein of interest. In another example, the PTR fluorescence signal of a protein of interest can be compared to the fluorescence signal (i.e., in another channel) of another protein of interest, for normalization or for analysis of differential protein production. In another example, the estimation of the protein based on the signal of the reporter protein with can be done through a linear regression technique. A linear regression that goes through the origin (0,0) could be performed between a standard (offline) measure of the protein of interest and the signal of the fluorescent protein. The slope of this regression (and the y intercept) enables the conversion of the fluorescent signal to the estimated value for the parameter. In another example, the fluorescence signal can be measured and compared against a measured phenotype, in a single cell. This can be used to determine the relationship between protein concentration and cellular phenotype. In a further example, the fluorescence signal can be measured over time in the same cell to quantify the change in protein production over time, such as before and after, e.g., an experimental manipulation, drug induction, or intervention.

Manufacturing an Exemplary Vector for Protein Quantification:

The nucleic acid sequences described herein used for protein quantification can be introduced as a vector in a host cell. The vectors can be generated by inserting the nucleic acid sequence encoding the PTR linker and the small fragment of the split fluorescent protein downstream from the nucleic acid encoding the protein of interest. This will result in the vector for transfection into a cell. The cell may express the large fragment of the split fluorescent protein or may have already been transfected with a vector of the nucleic acid sequence of the large fragment of the split fluorescent protein. The vector of the nucleic acid sequence of the large fragment of the split fluorescent protein may preferably be a plasmid containing promoter(s) and/or enhancer(s) that are configured to increase copy levels and expression efficiency (i.e. high-expression plasmid). Exemplary high-expression plasmids include, but are not limited to, pCAG and pCMV in mammalian systems, pUC in bacteria, etc. An exemplary promoter found in a high-expression plasmid may be the actin promoter. The high-expression plasmid ensures that the expression of the large fragment of the split fluorescent protein is sufficient such that its levels do not limit the rate of combining with the small fragment of the split fluorescent protein. The following are non-limiting examples of manufactured vectors used for protein quantification.

Example 1

1-DNA plasmids: the double-stranded DNA sequence encoding a PTR linker and small fragment of the split fluorescent (a PTR-XFP-11 construct) protein is inserted downstream of a DNA sequence encoding the protein of interest to be quantified.

A separate high-expression plasmid is used to harbor and express the DNA sequence encoding the larger XFP1-10 portion of the split reporter system.

PTR-XFP11 constructs can be chemically synthesized or amplified using PCR from other proprietary plasmids containing these reporters. Plasmids are propagated and purified from bacteria.

Example 2

2-ssODN: The double-stranded DNA sequence encoding a PTR linker and small fragment of the split fluorescent is cloned in between two DNA sequences homologous to a gene locus (For genome-editing). ssODN encoding a PTR-XFP11 construct can be chemically synthesized or assembled using standard molecular biology approaches. A separate high-expression plasmid is used to harbor and express the DNA sequence encoding the large fragment of the split fluorescent protein.

Example 3

3-mRNA: The single-stranded mRNA transcript encoding a PTR linker and small fragment of the split fluorescent is inserted downstream of a gene of interest, and is transcribed in vitro into ready-to-use mRNA from a DNA template. mRNA encoding the large fragment of the split fluorescent protein can be transcribed in vitro using a separate DNA template.

Exemplary Studies:

The following exemplary studies are provided to enable the skilled person to better understand the present disclosure. As they are but illustrative and representative examples, they should not limit the scope of the present disclosure, only added for illustrative and representative purposes. It will be understood that other exemplary studies may be used to further illustrate and represent the present disclosure without departing from the present teachings.

Example 1: Split Fluorescent Reporter DNA Constructs

Residues 1-213 of GFP, corresponding to the first 10 beta strands of GFP (GFP1-10), were amplified and cloned from evolved superfolderGFP. GFP11 was generated by amplifying and cloning the last 15 residues of GFP into pCAG. To stoichiometrically co-express GFP1-10 or GFP11 with other proteins of interest, a PQR construct was added in-frame upstream or downstream of the GFP1-10 or GFP 11 sequence depending on the desired orientation. For extracellular membrane-bound expression of GFP1-10, the complete Neuroligin-1 signal sequence, in addition to portions of the Neuroligin-1 extracellular, transmembrane, and intracellular anchoring domains were fused to the N-terminus of GFP1-10[20]. For electrophysiology experiments, a PQR-GFP11 reporter was placed downstream of the ShakerRFP coding sequence to generate ShakerRFP-PQR-GFP11, and cloned into pCAG. Split mCherry was generated as described[32]. Split Dendra2 was generated by separating mDendra2 (Evrogen, Moscow, Russia) at Proline 191 to generate Dendra1-10. The remaining 39 residues (Dendra11) were cloned into pCAG or placed downstream of a PQR to generate a Dendra11 protein translation reporter. For ZIKV experiments, the portion corresponding to full length NS4B was cloned from African ZIKV strain *Aedes africanus*/SEN/DakAr41524/1984 (Genbank: KX601166.2) or Asian ZIKV strain isolate 15098 (Genbank: MF073359.1), upstream of PQRGFP11 into pCAG. For transgenic animals, the sequence encoding GFP1-10 was cloned downstream of the mouse or fly ActinB promoter. For mouse transgenesis, Actin>GFP1-10 was cloned into pCAG and injected into mouse blastocysts according to standard transgenic practices (McGill Core Transgenic Facility). Similarly, fly Actin>GFP1-10 was cloned into a modified version of pCFD3 (Addgene 49410), and injected into fly embryos (BestGene Inc.).

Example 2: XFP1-10 Protein Production and Extraction

DNA encoding XFP1-10 protein was transformed and expressed under the control of an arabinose inducible promoter in *Escherichia coli* strain BL21(DE3) (New England BioLabs, Ipswich, Mass.). Cells were grown in Luria broth medium to an initial optical density of 0.2, at which point induction of protein production was initiated with 0.2% L-Arabinose and cells were further grown at 37° C. for an additional 16 hours with shaking at 225 rpm to encourage inclusion body formation. Cultures were harvested using centrifugation and XFP1-10 was purified from inclusion bodies by resuspension with TNG buffer (100 mM Tris-HCl (pH 7.4), 150 mM NaCl, 10% glycerol vol/vol) containing 0.5 mg/ml lysozyme, 50 units of DNase I. The lysate was then incubated at 37° C. for 25 min. Crude lysates containing XFP1-10-rich inclusion bodies were separated using centrifugation at 16,000 g at 4° C. Inclusion bodies were lysed using B-Per (Thermo-Fisher) and sonication and XFP1-10 protein was collected and filtered using a 0.22 μm filter before concentration with 10,000 molecular weight exclusion columns.

Example 3: XFP11 Peptides

Variants of the XFP11 peptide were chemically synthesized with >75% purity (Genscript, Piscataway, N.J.). The amino acid sequences of the GFP11 peptides were: GFP11v1: SEQ ID NO: 78, GFP11v2: SEQ ID NO: 79 and GFP11v3: SEQ ID NO: 80 (see Table 1 for full sequence list). Lyophilized peptides were resuspended in water to >10 mg/mL and frozen at −20° C. For extracellular GFP reconstitution in HEK293 cells, GFP11 peptide was dissolved into the culture medium at a final concentration of 50 μM and cells were returned to a 37° C. incubator for 2 hours before live imaging.

TABLE 1

Sequences of PQR and PTR variants used.

| Construct | DNA sequence | Peptide Sequence |
|---|---|---|
| GFP11 | ATGGGAGGGGGGGGTTCAGGTGGTGGCG GGAGTCGAGACCACATGGTATTGCACGA ATACGTCAACGCCGCAGGCATAACATGA | MGGGSGGG GSRDHMVLH EYVNAAGI T* |
| sfCherry11 | ATGGGAGGGGGGGGTTCAGGTGGTGGCG GGAGTTACACCATCGTGGAGCAGTACGA GAGAGCCGAGGGCAGACACAGCACCGGC GGCTGA | MGGGGSGGG GS YTIVEQYERA EGRHSTGG* |
| Dendra11 | ATGGGAGGGGGCCCCGACGCCCACTTCG TGGACCACCGCATCGAGATCCTGGGCAA CGACAGCGACTACAACAAGGTGAAGCTG TACGAGCACGCCGTGGCCCGCTACAGCC CCCTGCCCAGCCAGGTGTGGTAA | MGGGPDAHFV DHRIEILGND SDYNKVKLYE HAVARYSPLP SQVW* |
| PQR | GgaagcggaGCGACGAATTTTAGTCTAC TGAAACAAGCGGGAGACGTGGAGGAAAA CCCTGGACCT | GSGATNFSLL KQAGDVEENP GP |

Example 3: In Vitro Protein Reconstitution

In vitro fluorescence complementation was performed by mixing purified XFP1-10 protein and chemically synthesized XFP11 peptides and the fluorescence intensity of the reaction was collected with a StepOnePlus real-time thermal cycler (Thermo-Fisher). 3 mM XFP1-10 in TNG buffer or PBS (varied pH) was added to wells of a 96-well microplate coated with 1 mM bovine serum albumin and allowed to equilibrate for 60 seconds. XFP11 peptide was added according to different final peptide concentrations and the microplate was immediately loaded into the fluorescence reader. The fluorescence intensity was measured every 10 seconds for 45 minutes at 32° C. or 37° C. with 495 nm excitation and 520 nm emission. The fluorescence intensity was normalized to the initial fluorescence intensity to express relative fluorescence increase upon fluorescence reconstitution. Split GFP, mCherry, and Dendra2 were verified to have similar rapid kinetics, and that UV illumination did not photoconvert the splitDendral-10. Standard curves for XFP fluorescence measurements were generated by either using reconstituted XFP or XFP purified from E. coli using GFP specific chromatography columns (Bio-Rad). XFP protein concentration was determined using the Bradford assay and absorbance readings at 280 nm with a NanoDrop 2000 (Thermo-Fisher). Samples were serially diluted (1:10 or 1:5) and 10 μL samples were imaged to reduce any non-linear fluorescence excitation effects. For sub-second kinetic measurements, a Fluorolog-3 spectrophotometer (Horiba) fitted with a stopped-flow dispenser was used to simultaneously dispense and mix known volumes of XFP1-10 and XFP11 purified proteins at room temperature. Total fluorescence intensity (in photon counts) was collected every 0.1 s or 0.01 s for varying durations.

Example 4: Cell Culture

HEK293 cells were cultured at 37° C. under 5% CO2 in Dulbecco's Modified Eagle Medium, supplemented with 10% fetal bovine serum (Wisent), or for Drosophila melanogaster S2 cells, at 25° C. in Ex-Cell 420 Medium (Sigma-Aldrich). Media were supplemented with 100 units/mL penicillin (Thermo-Fisher) and 100 μg/mL streptomycin (Thermo-Fisher). Mammalian cells were transfected with 3.5 μg of plasmid DNA in 35 mm dishes using Lipofectamine 3000 (Thermo-Fisher), or Transit-Insect (Mirus) for Drosophila cells. For extracellular GFP fluorescence reconstitution, HEK293 cells were transfected with constructs expressing GFP1-10 tagged to the transmembrane and extracellular domains of the cell surface molecule Neuroligin-1 and incubated for 24-36 hours. Cells displaying GFP1-10 on the extracellular side of the cell membrane were incubated in culture medium containing 50 μM GFP11 peptide for 3 hours at 37° C. before live imaging. GFP1-10 protein was allowed to accumulate for 24 hours before transfection of GFP11 constructs. For genome editing experiments, 800 ng of CRISPR-Cas9 plasmid DNA were cotransfected with 800 ng of single stranded oligonucleotide repair templates in 12-well plates. After 2-7 days, cells were non-enzymatically dissociated and seeded on glass coverslips and prepared for imaging and electrophysiology experiments.

Example 5: Endoplasmic Reticulum and Ribosome Staining

To visualize endoplasmic reticula (ER), HEK293 cells were transfected with split GFP PQR reporter constructs and stained (live or fixed) with the ER and ribosome-specific stain Cytopainter (Abcam). Stained cells were imaged in the green and red channels to examine the co-localization of reconstituted GFP and red ER signals. Colocalization of green and red signals was determined by calculating the Pearson's and Mander's correlation coefficients for overlapping green and red pixel intensities. Individual z-planes were background subtracted and thresholded to remove the lowest and highest pixel intensities. Ten regions of interest (ROIs) within the cell and excluding background and nuclear regions were used for analysis. Both Pearson and Mander's colocolization coefficients were independently obtained and cross validated using Coloc2 (ImageJ) and BiolmageXD[29].

Example 6: Image Acquisition

Fluorescence and brightfield microscopy were performed using a Zeiss AxioScope A1. All images were acquired at 1388×1040 pixels using a 40× water objective, N.A. 1.0 (epifluorescence). Fluorescence emission was detected using a charge-coupled device (CCD) camera (MRm). All image acquisition parameters were fixed for each imaging channel for exposure time, excitation intensity and gain. Cells that were dimmer or brighter than the fixed initial acquisition dynamic range were not included for analysis. Time-series images were collected using an open-shutter video configuration in ZenLite (Zeiss). Images were acquired every 167 milliseconds with exposure times of 260 milliseconds. For in vivo 2 photon imaging, juvenile mice (P10-P20) were anaesthetized using ketamine/xylazine/acepromazine and a 4×4 mm square window was made through the skull using a dental drill fitted with a 0.45 mm drill burr. The meninges were carefully removed and the exposed brain was covered with 1% optically clear agar and sealed with a No. 1 round coverslip. The coverslip was secured to the skull using dental cement and a mounting fixture was also placed (FIG. 4A, right panel) to facilitate securing the mouse under the objective to minimize animal movement, breathing artifacts and vibration. Images were acquired at 512×512 pixels using a 40× water objective, N.A. 1.0.

Example 7: Image Analysis

Images were selected for analysis based on identification of healthy cells and low background. Fluorescence pixel intensities were measured in several random ROIs within the target cellular region using a custom written program in MatLab (MathWorks) or ImageJ. Average pixel intensities were calculated from five ROIs of 7×7 pixels for measurements within the cytoplasm, perinucleus, and nucleus, and 3×3 pixels for measurements within the plasma membrane. All signal intensities were background subtracted from the average of three ROIs immediately surrounding the cell. For time-series image analysis, background was considered as the region immediately adjacent (<15 μm) to the perinucleus, or cytoplasm. For co-localization analysis, Mander and Pearson's correlation coefficients were calculated for individual z-slices. Using the ribosome marker in the red channel with PTR GFP experiments, green and red pixel intensities were confirmed to colocalize, with 71% of above-threshold GFP signals co-localized with 82% of above-threshold red signals. Thresholded Mander's (tM) coefficients tM1=0.71, tM2=0.82, Pearson's $R_2$=0.84, and Costes p-value=1 (i=100, n=10 ROIs). Kinetic increases in fluorescence from timelapse or video data were plotted was $F_t/F_0$.

For ZIKV translation dynamics experiments, autocorrelation analysis of the single cell fluorescence time courses was used to provide an unbiased estimate of the temporal variation in protein translation events between ZIKV strains. One-phase decay exponential fits to the autocorrelation function resulted in a time constant of $\tau=8.84\pm9.48$ seconds for ZIKV 150989 ($R2=0.99$, n=3 cells, 2 animals) and $\tau=12.86\pm11.23$ seconds for ZIKV Ar41524 ($R2=0.97$, n=4 cells, 2 animals).

An autocorrelation analysis was also performed on the fluorescence time course as an unbiased estimate of burst duration using different regions of interests within the soma and dendrites. A single exponential decay was fit to the autocorrelation function and resulted in an average time constant of $\tau=8.84\pm9.48$ seconds for Asian ZIKV ($R2=0.99$, n=3 cells, 2 animals) compared to $\tau=12.86\pm11.23$ seconds for African ZIKV ($R2=0.97$, n=4 cells, 2 animals) (mean±SD, p=0.54, n=7 cells).

Example 8: Electrophysiology

Standard whole cell voltage clamp was used to record potassium currents from HEK293 cells[6]. Cells were maintained at 25° C. in extracellular solution containing 140 mM NaCl, 10 mM CaCl2), 7.5 mM KCl, 10 mM HEPES, and 10 mM glucose at pH 7.4, 319 mOsm during recordings. Patch electrodes were pulled from standard wall borosilicate glass (BF150-86-10, Sutter instruments) with 3-5 MΩ resistances. The intracellular pipette solution was 120 mM KCl, 2 mM $MgCl_2$, 1 mM $CaCl_2$, 2 mM EGTA, 20 mM HEPES, and 20 mM sucrose at pH 7.23, 326 mOsm. Whole cell currents were low pass filtered at 10 kHz and measured using an Axopatch 200B amplifier (Axon instruments), and recorded using a DigiData 1200 with pClamp9 software (Molecular Devices). Cells were held at −80 mV and then given +20 mV steps of 45 ms. To accurately compare I-V curves and current data across cells and experiments, the steady-state current was divided by the membrane capacitance (mean Cm=15 pF, n=3), and current density (pA/pF) was used for comparisons. Consistent cell capacitance, and membrane and access resistances were verified before and after recordings.

Example 10: Statistical Analysis

Pearson's linear correlations were calculated by fitting the data to a simple linear regression model, with the coefficient of determination, $R_2$. Kinetic reconstitution traces were fit with a simple one-site binding model with the coefficient of determination $R_2$ using Prism (GraphPad). The F test was used to test the null hypothesis that the variables were independent of each other and that the true $R_2$ value was 0 for both linear and nonlinear models. Autocorrelation analysis was performed using custom-written programs in MatLab (MathWorks, Natick, Mass.). The autocorrelation function was fit to single-phase exponential decay models using Prism (GraphPad). A Mann-Whitney U test was used to test the null hypothesis that protein synthesis burst rates between the two Zika virus strains are not different.

Example 11: Genome Editing Using CRISPR-Cas9

Guide RNAs were designed as 20 bp DNA oligonucleotides and cloned into pX330 (Addgene 42230), and co-transfected with a circular PQR repair template using Lipofectamine LTX (Life Technologies). All CRISPR-Cas9 guide RNAs were tested for activity using SURVEYOR Nuclease and SURVEYOR Enhancer S (Transgenomics) on extracted genomic DNA. Re-annealed products were analyzed on 4%-20% Novex TBE polyacrylamide gels (Life Technologies). To construct the repair templates, the gene sequences were identified in the human genome using GeneDig™ and then PCR amplified. Repair templates were constructed by placing PQR-XFP between homology arms specific for the genes. The homology arms lacked the promoter, which prevented expression of the PQR-XFP until in-frame genomic integration within an active coding gene. Left and right homology arms were 1.0 kilobases. Cellular fluorescence from PQRs was observed four days post-transfection.

Example 12: Neonatal Brain Electroporation

Figure 4A:
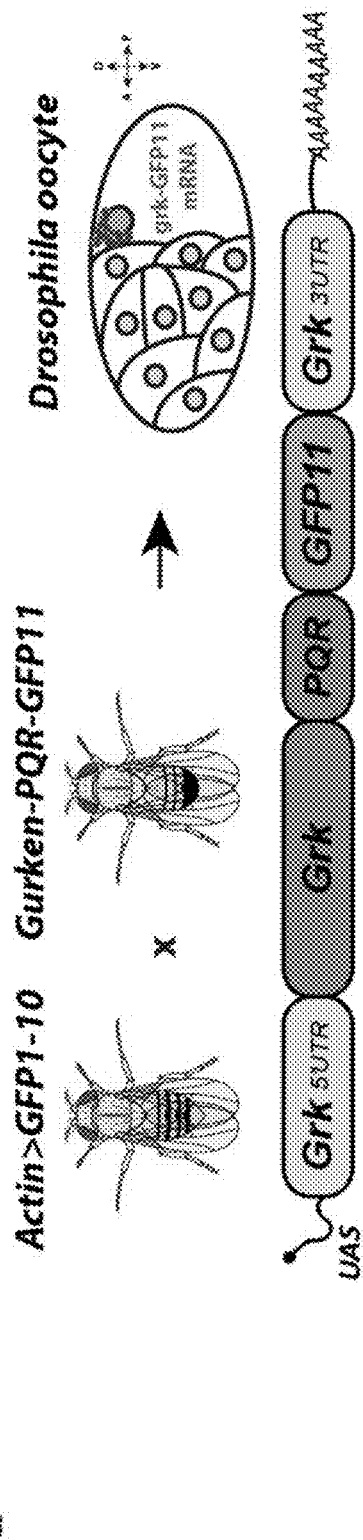
FIG. 4A, relating to direct observation of protein synthesis over time in vivo, is a diagram that shows a transgenic fly line expressing GFP1-10 under the Actin promoter (Actin>GFP1-10) that was created to ubiquitously express GFP1-10 at high levels. UAS-Grk-PQR-GFP11 flies were created to visualize translation of local mRNAs. The sequence of As of the mRNA is a poly(A) tail and corresponds to SEQ ID NO: 83. The grk transcript contained the native grk 5' and 3' untranslated regions (UTR) to ensure proper regulation and localization to the anterior dorsal corner of the oocyte near the nucleus, where its translation Gurken initiated. To generate oocytes that express the Gurken-PQR-GFP11, nanos-GAL4 were crossed to the UAS-Grk-PQR-GFP11 flies, and then crossed those progeny to the Actin>GFP1-10 flies.

P0-P1 Actin>GFP1-10 mouse pups were anesthetized on ice until no reflexes were observed. 2 μg/μl NS4B-PQR-GFP11 DNA (from Asian ZIKV strain 150989 or African ZIKV strain Ar41524) was dissolved in water was mixed with 0.1% FastGreen dye and loaded into a O.D./I.D. 1.5/0.786 mm pulled and beveled borosilicate glass micropipette (Sutter Instruments). The micropipette was slowly inserted into the right lateral ventricle or ~1.5 mm into the right cortical hemisphere, ~1.5 mm laterally from bregma (FIG. 4a). Around 200 nL DNA/dye solution was slowly injected and the DNA solution was allowed to diffuse for 3 minutes. After 3 minutes, platinum tweezer electrodes (Nepagene) were placed around the pup head such that the negative electrode contacts the injected side of the head. A drop of PBS was used under the electrodes to transmit the pulses and reduce burning. Two sets of (100 V, 50 ms, 9 pulses, 950 ms apart) separated by 3 seconds were delivered and the animal was allowed to recover on a 37° C. heated blanket. The pups were returned to their mother once awake and active.

Example 13: Protein Quantification Ratioing with Increased Spatial and Temporal Resolution The experimental procedures associated with this example were presented in examples 1-12.

To demonstrate the approach, several variants of GFP were screened, and it was found that some versions of split GFP[17,19-23] would not always express properly in cells and could aggregate in inclusion bodies or misfold, so different modifications were screened through that added specific amino acids to the carboxy and amino terminus of GFP11 and GFP1-10, respectively (Methods, Table 1). Expression of GFP1-10 on the cell surface of HEK293 cells produced green fluorescence when exposed to extracellular GFP11 peptide, and co-expression of GFP1-10 and GFP11 in human neural progenitor cells (hNPC) and mouse cortical neurons produced bright green cytoplasmic fluorescence signals that were not sequestered into inclusion bodies or lysosomes (FIG. 1c-e). The protein translation dynamics of the GLUA1 subunit of the AMPA receptor, measured as changes in green fluorescence, were recorded over time from human and mouse neural cells and found to vary across different sampling locations within the cell body and along neurites (FIG. 1d, e), indicating local differences in protein production levels.

To determine the speed of reconstitution of our modified split GFP, the purified GFP1-10 at 3 mM with varying concentrations of GFP11 were combined and found that fluorescence was detected immediately upon mixing the two solutions (FIGS. 1F-1H). In an effort to obtain kinetic measurements of the reconstitution reaction at sub-second timescales, an ultrasensitive fluorescence spectrophotometer was used (Methods). A stopped-flow dispenser was used to mix and deliver known volumes of GFP1-10 and GFP11 proteins. A t0 for the moment split GFP components first interact was established. Green fluorescence was detected immediately upon mixing the two solutions (within 100 ms) (FIG. 1F), and the fluorescent intensity of the reconstitution reaction steadily increased throughout the recording window (~60 seconds) (FIG. 1F, inset). Fluorescence increase over time from the bimolecular reaction was modeled as pseudo-first order and fit to a one phase association curve to determine the observed rate constant (kobs) of GFP11 peptide binding as 0.007±0.0001 s-1 and a half time of 95 seconds ($R^2$=0.99, p<0.001) (FIG. 1G). Fluorescence increase over time with varying GFP11 peptide concentrations (FIG. 1H) was fit to a one site binding model to determine the dissociation constant (Kd) of the GFP11 peptide as 481±116 pM ($R^2$=0.96, p<0.05), demonstrating that GFP11 peptide binds GFP1-10 with very high affinity and unlikely to dissociate[22-24].

Using a standard curve of known concentrations of reconstituted split GFP (FIG. 1B, top left), the number of reconstituted molecules being produced was estimated at millions per millisecond. In the volume of a medium size cell would be hundreds of molecules produced per millisecond for even the slowest, lowest concentration of these reactions. Thus, GFP11 reconstitution with GFP1-10 allows for detection of protein synthesis events at the millisecond timescale.

Figure 1B:
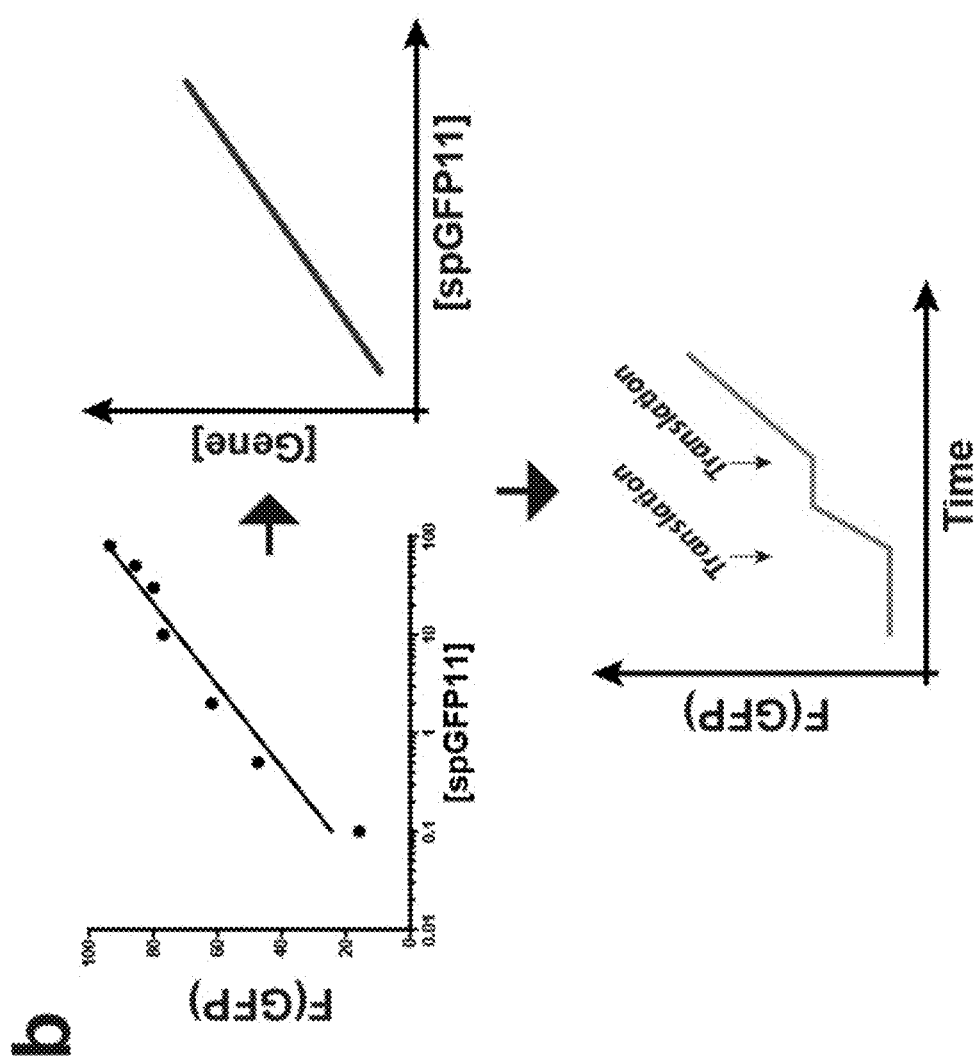
FIG. 1B, relating to the stoichiometric production of GFP11 reporter using a PTR linker to allow instantaneous detection of protein translation, are three graphs that illustrate how a series of linear relationships allows for PTR to quantify protein translation events is shown. First, the fluorescence intensity of the reconstituted GFP is linearly dependent on the input concentration of GFP11 over two orders of magnitude (left panel). Second, the level of GFP11 production is proportional to the level of protein of interest production (right panel) due to PQR (a). Thus, the fluorescence intensity of GFP reconstitution (i.e., brightness) can be used to determine the moment and amount of synthesis of the protein of interest over time.
Figures 1C, 1D, 1E:
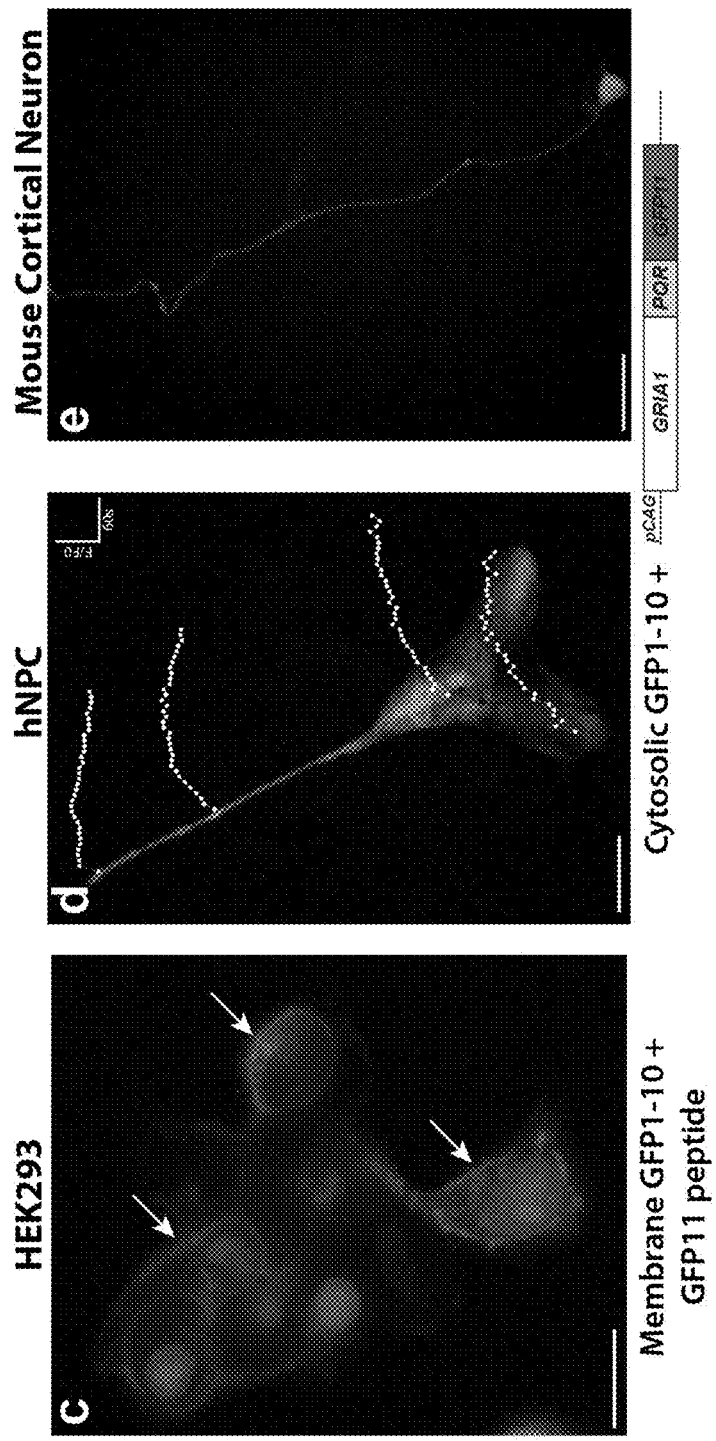
FIG. 1C, relating to the stoichiometric production of GFP11 reporter using a PTR linker to allow instantaneous detection of protein translation, is a photograph taken with a microscope that illustrates that split GFP reporters can be expressed and reconstitute properly using PQRs. Membrane-tagged GFP1-10 was expressed on the extracellular surface of HEK293 cells and produced a bright green membranous fluorescent signal upon addition of 50 μM GFP11 peptide into the culture medium.
FIGS. 1D-E, relating to the stoichiometric production of GFP11 reporter using a PTR linker to allow instantaneous detection of protein translation, are photographs taken with microscopes that show split GFP components expressed within the cytosol of human neural progenitor cells and mouse cortical neurons reconstituted to produce fluorescent GFP without the formation of inclusion bodies. Traces representing the dynamics of GluA1 translation across different regions of interest are overlaid (Figure D).
Figure 2A:
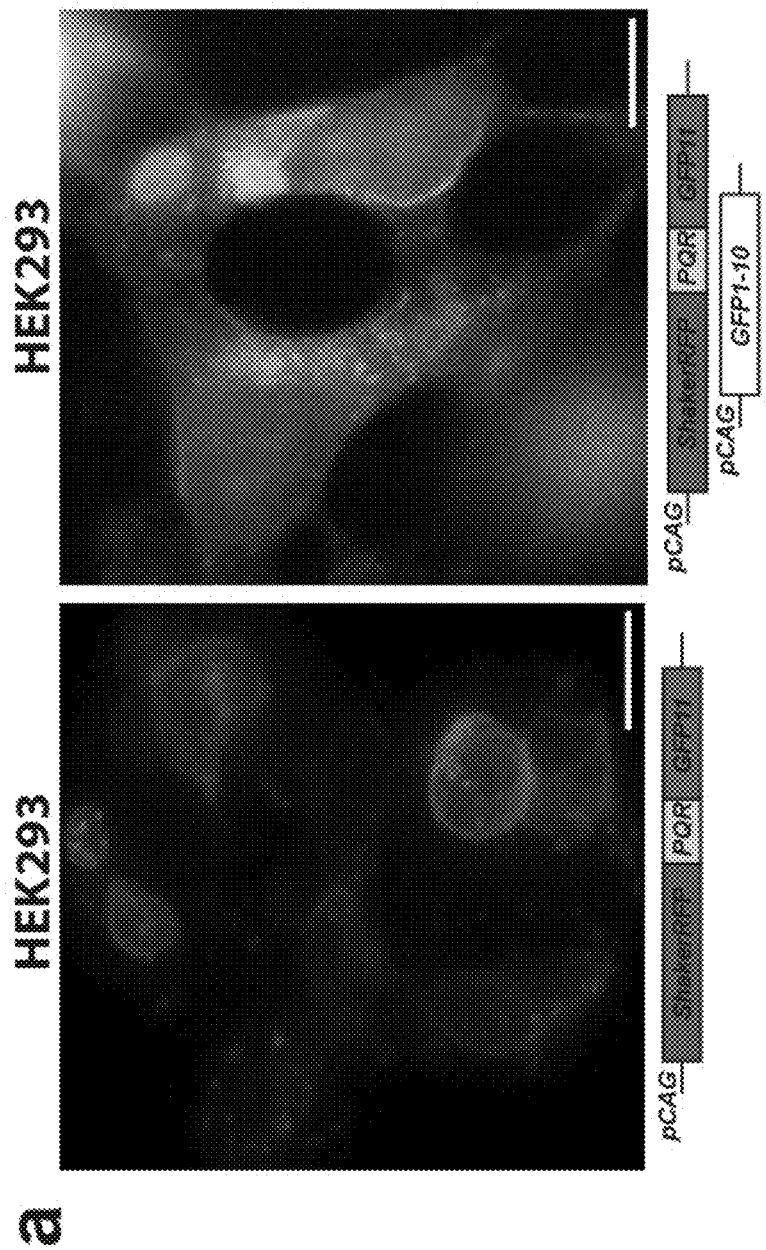
FIG. 2A are photographs and FIGS. 2B and 2C, relating to the direct observation of protein synthesis at ribosomes, illustrate how using PQR to co-translate GFP11 preserves the protein of interest's localization and function. Expression of ShakerRFP-PQR-GFP11 in HEK293 cells (FIG. 2A) produced red fluorescent signal at the cell membrane, indicating that the ShakerRFP potassium channel was processed and inserted correctly. With the addition of GFP1-10, the GFP11 reporter reconstituted with GFP1-10 and produced cytoplasmic fluorescent GFP which remained in the cytoplasm. Potassium conductances (FIG. 2B) in cells transfected with ShakerRFP-PQR-GFP11 were consistent with previous Shaker currents[14]. Green and red fluorescence intensities with linearly correlated (FIG. 2C), indicating that the level of GFP11 production is proportional to the level of ShakerRFP production. Scale bars are 30 µm in FIG. 2A, left panel and 20 µm in FIG. 2A.
Figures 2B, 2C:
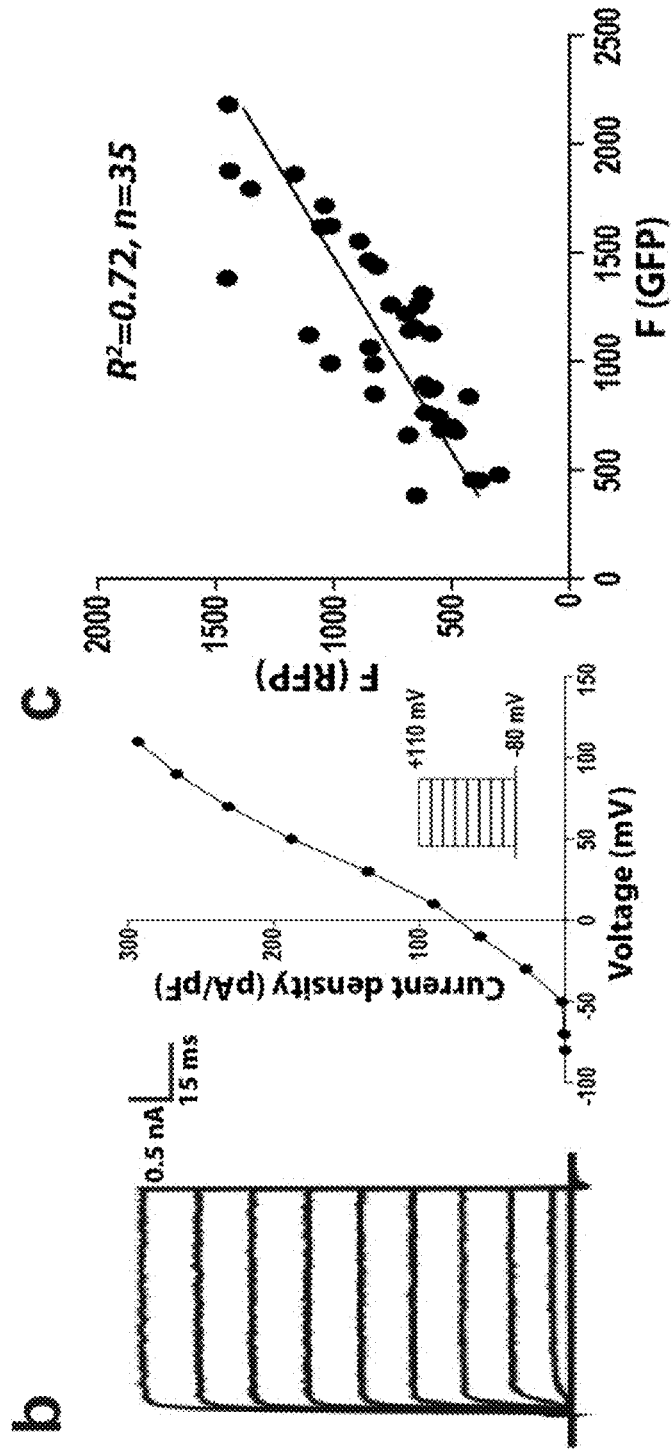
FIGS. 2D-E, relating to the direct observation of protein synthesis at ribosomes, are photographs taken with a microscope that illustrate that reconstitution of split GFP11 occurs immediately after translation. HEK293 cells expressing split GFP constructs (FIG. 2D) were labeled with a red marker for endoplasmic reticula and ribosomes (Cytopainter). Image analysis of fluorescent pixel intensities (FIG. 2E) showed a strong co-localization, particularly at perinuclear regions (bottom panel, arrows). Pixel intensities of different wavelengths co-occurred (FIG. 2E) with 71% of GFP signals co-localized with 82% of red ribosome signals ($R^2=0.84$) (Methods, Supplemental Information). Scale bars are 30 µm FIG. 2D and FIG. 2E, top panels, and 20 µm in FIG. 2E, bottom panel.
FIGS. 2F-G, relating to the direct observation of protein synthesis at ribosomes, are graphs that show that GFP fluorescence increases over time at peri-nuclear ribosome sites. Single cell analysis of fluorescence intensity over time from perinuclear (top panel, n=6) or cytoplasmic (bottom panel) regions showed increases over seconds. Fluorescence intensity analysis at perinuclear and cytoplasmic regions of interest in cells expressing PTR showed increasing levels at perinuclear regions compared to within the cytoplasm (FIG. 2G).

Using PQR with GFP11 produces a linear relationship with the protein of interest, allowing for quantification of the amounts of protein synthesis in a cell using fluorescence intensity (FIG. 1B). It was verified that the reconstituted GFP could quantify protein synthesis using the *Drosophila* Shaker potassium channel with a red fluorescent protein (RFP) embedded within the inactivation domain[14] (FIG. 2A). Shaker K+ currents were recorded from HEK293 cells expressing the ShakerRFP gene tagged with PQR-GFP11 (ShakerRFP-PQR-GFP11) along with GFP1-10 and confirmed that the PTR did not disrupt protein function (FIG. 2B). RFP fluorescence intensity was correlated with reconstituted GFP with an $R^2$=0.72, n=35, p<0.05 (FIG. 2C). GFP puncta was observed throughout the cell, indicating sites of local translation, possibly near the rough endoplasmic reticulum, as the Shaker potassium channel is being processed while the GFP11 diffuses away in the cytosol.

Figures 2D, 2E:
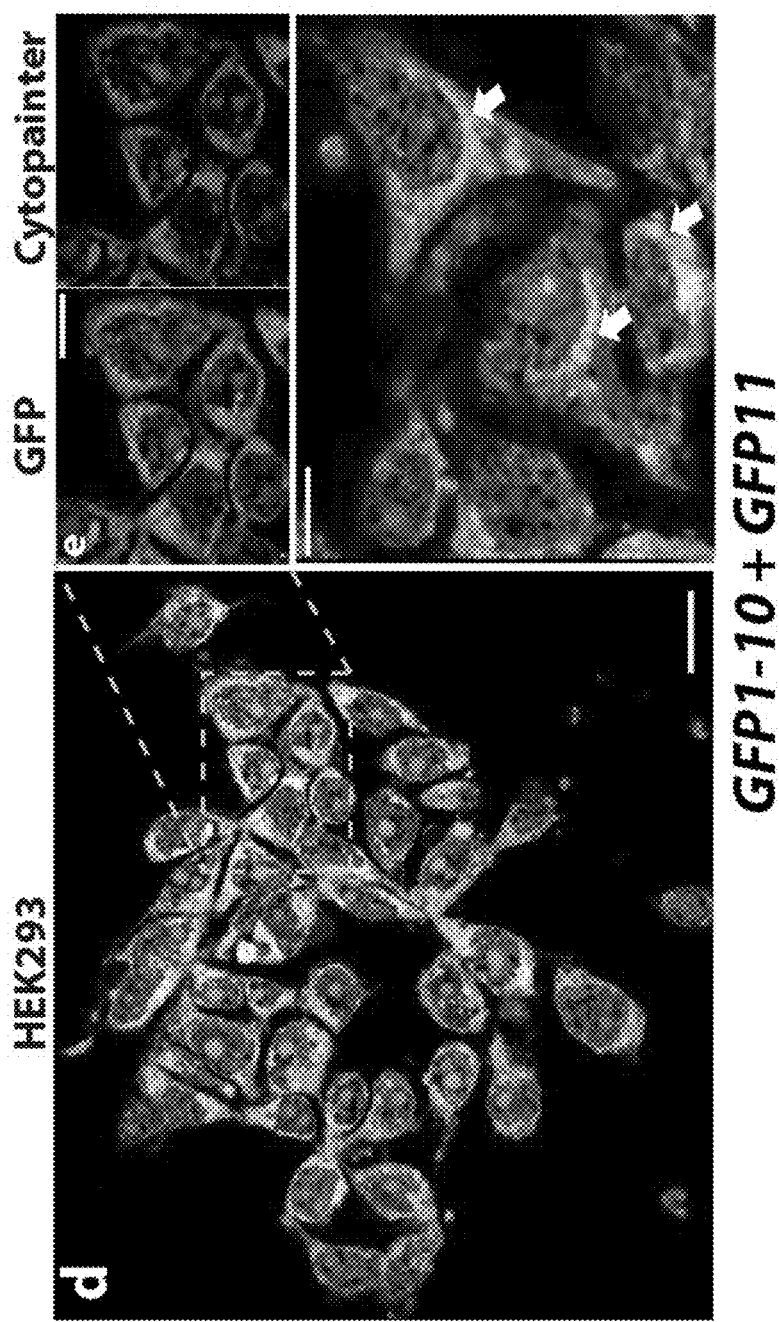
Figures 2F, 2G:
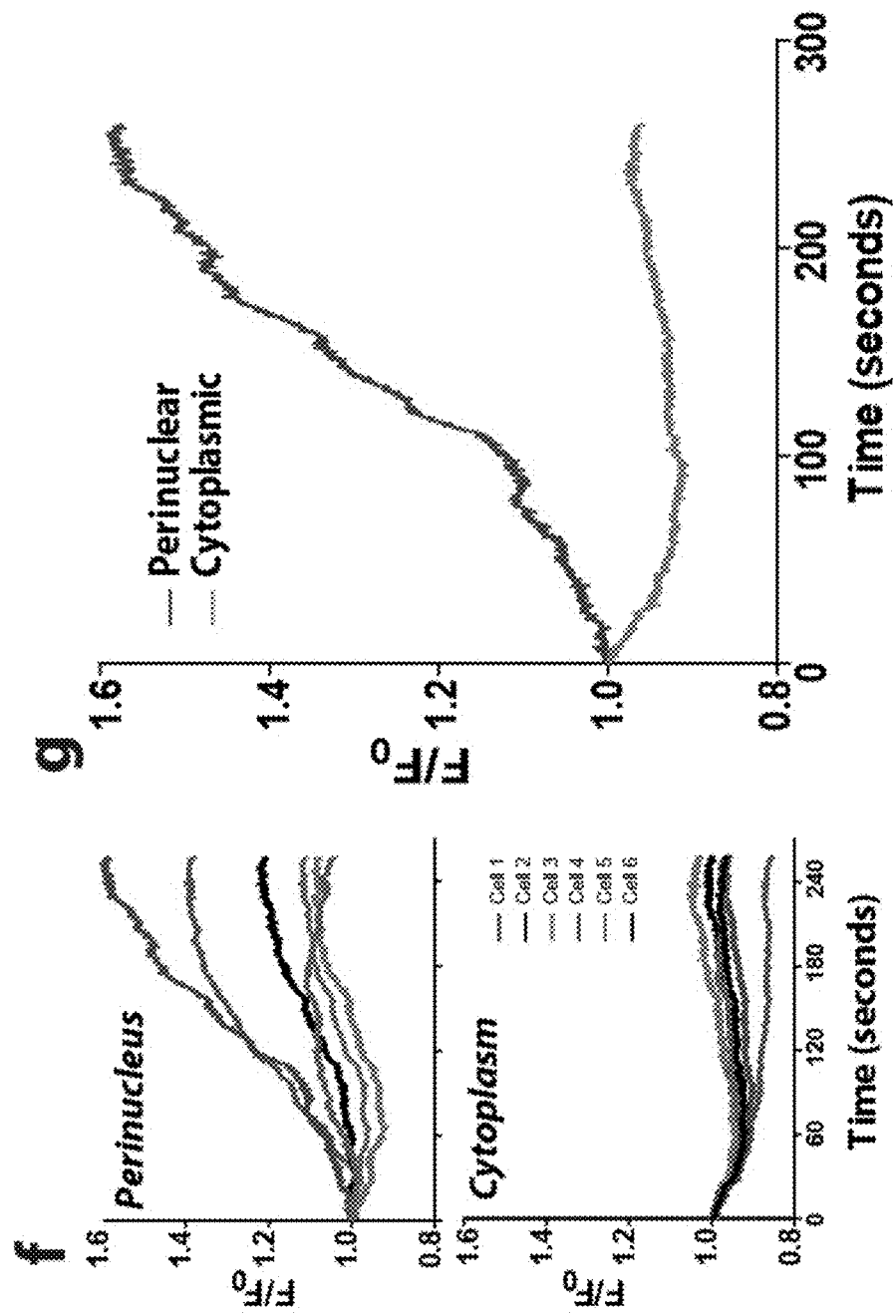

Direct observation of protein synthesis was sought at ribosomal sites over time, so a live marker for ribosomes in the red channel, Cytopainter, was used. Rapid increases were observed in green fluorescence intensity over seconds at perinuclear sites which were strongly labeled in red, indicating protein synthesis of the GFP11 at perinuclear ribosomes directly after mRNA export from the nucleus (FIG. 2D, FIG. 2E). Red and green fluorescence were co-localized throughout the cell (FIG. 2E), and green fluorescence increased over time only at perinuclear regions compared to the cytoplasm (FIG. 2F, FIG. 2G). Protein translation of the 26 residues that make up the GFP11 occurs within a few seconds[25,26] but even as the protein of interest diffuses away or is translocated into the endoplasmic reticulum during the GFP11 synthesis, the fluorescence event still signifies the ribosomal site of protein translation. Diffusion coefficients for mRNA decorated with ribosomes will vary based on the overall size[27], but one estimate of 0.04 µm2 s-1 indicates that the ribosome will travel a root mean square distance of less than 500 nm in 3 seconds[28]. Using PTR, there will be a <1 µm spatial variance in detecting the location of the original synthesis event. Traditional methods of protein synthesis reporting using even the fastest folding and maturing fluorescent proteins (which does not account for the time for synthesis of the protein itself) would introduce a 5 minute temporal spread and a 230 µm spatial spread in detection efficiency.

Figure 3A:
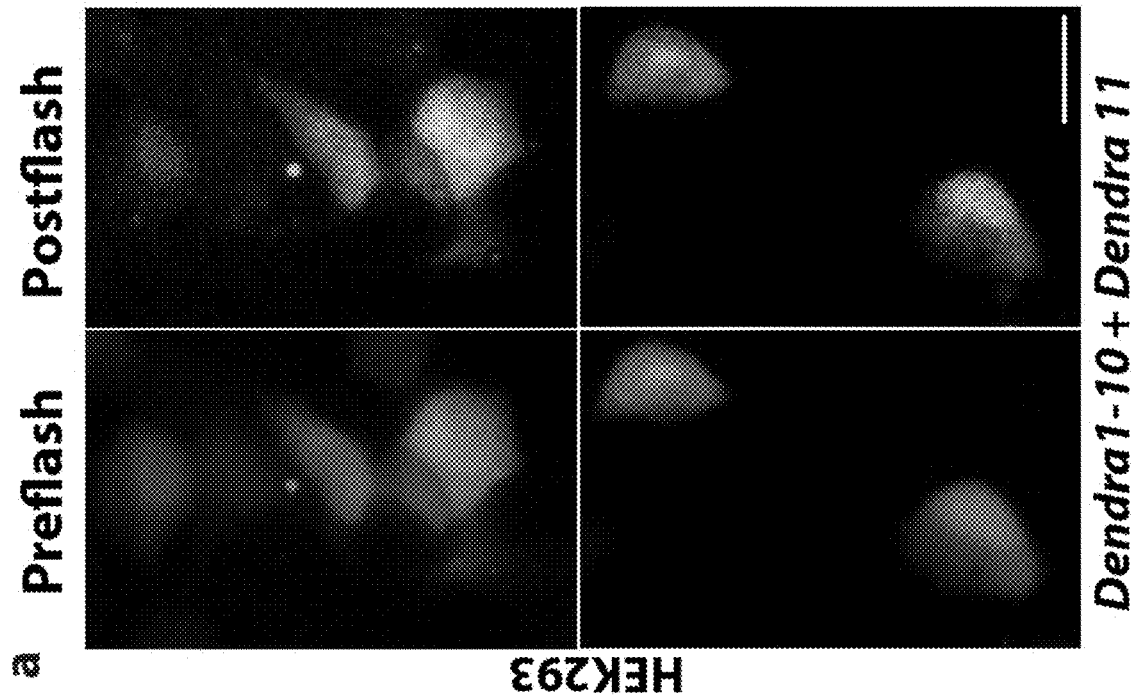

The accumulation of the PTR fluorescence signal over time can eventually make it difficult to detect local protein synthesis events. Possible solutions are to photobleach or to photoconvert the previously generated fluorescent signal. However, photobleaching is undesirable due to the risks of photodamage to the cell and its protein translation complexes, and diffusion of unbleached fluorescent protein into the site. Thus, the monomeric photoconvertable fluorescent protein, mDendra2, was split, which normally emits green fluorescence, but can be permanently photoconverted to emit red fluorescence by UV illumination[29] (FIG. 3A). By co-expressing these two "Dendra1-10" and "Dendra11" split photoconvertable fluorescent proteins in HEK293 cells, bright green fluorescence was observed. The green fluorescence was then photoconverted by a 5 second flash of UV illumination to red fluorescence (FIG. 3A). New protein synthesis was then observed with the increase of green fluorescence over time (FIG. 3B). Mixing purified Dendra1-10 and Dendra11 peptides in vitro produced detectable green fluorescence within seconds (FIG. 3C, left), and the fluorescence intensity rose steadily throughout the recording window (FIG. 3C, right), albeit at a slower rate than that of GFP1-10 and GFP11. Using split photoconvertible fluorescence proteins can enable the precise determination of the moment of protein synthesis, in addition to the rate, by resetting measurement windows at any point in the life of the cell or animal, without the harmful effects associated with photobleaching.

Figure 3D:
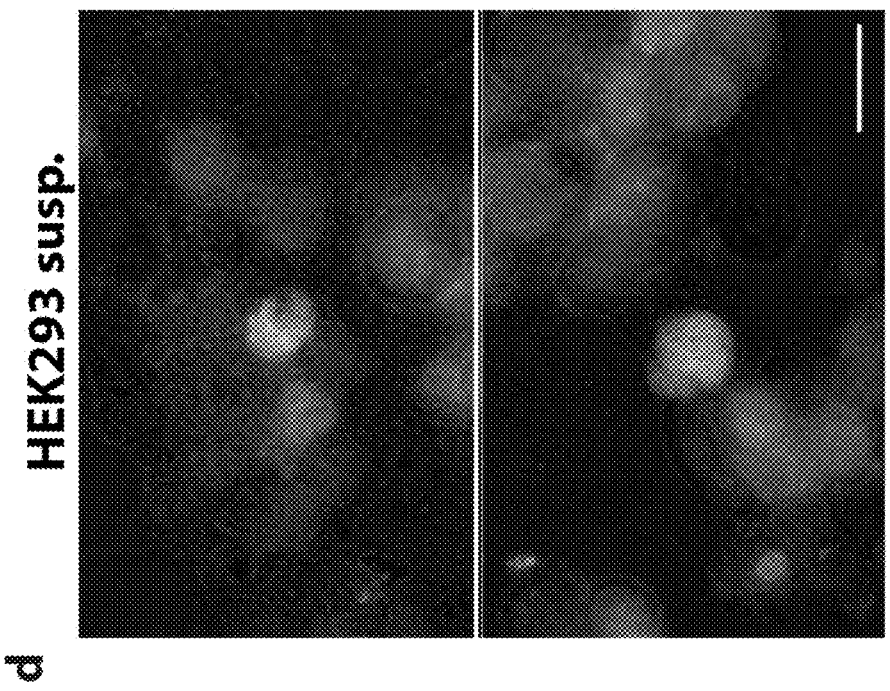
FIG. 3D, relating to spectral variants of split PTR, are photographs that show multiple genes or alleles can be simultaneously tracked and quantified using other colors of split fluorescent proteins. CRISPR-Cas9 genome editing can insert the small, <80 bases, PTR into genomic loci to measure endogenous protein synthesis. HEK293 cells to were genome edited insert PTRs of GFP11 and mCherry11 into the Ribosomal Protein L13A (RPL13A) and Amyloid Precursor Protein (APP) genes, respectively. Fluorescent cells emitting fluorescence at different wavelengths simultaneously report the instantaneous protein synthesis of RPL13A and APP over time. Scale bar is 20 µm.
Figure 3E:
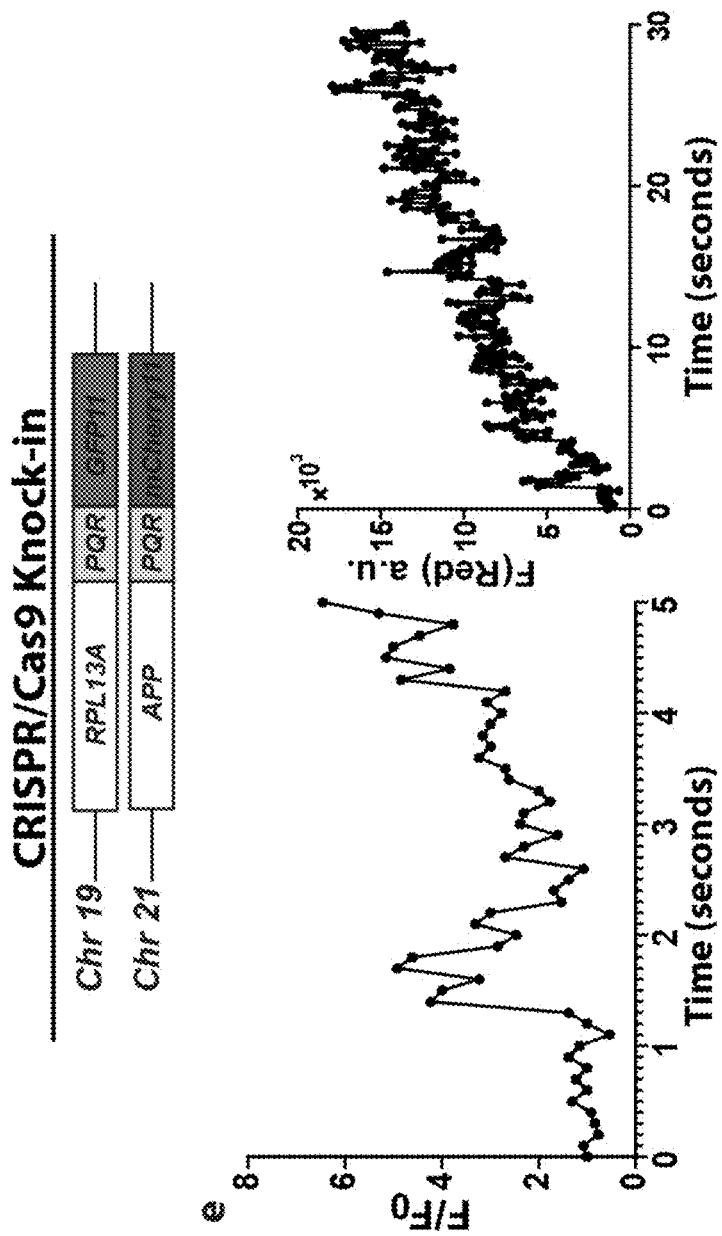
FIG. 3E, relating to spectral variants of split PTR, are graphs that show reconstitution of Cherry1-10 lysate and purified Cherry11 peptide resulted in fluorescence, corresponding to red fluorescence, that was detectable immediately after mixing. Fluorescence output was recorded every 0.1 seconds for a duration of 30 seconds.

To quantify multiple genes or alleles simultaneously, other split fluorescent proteins[18,22,25] can be adapted for PTR for multi-color imaging of protein synthesis. For example, CRISPR-Cas9 genome editing was previously used to insert PQRs with different fluorescent proteins into multiple endogenous genes[14,30] or to track each parental allele[31]. To this end, a split red fluorescent protein was used, mCherry[32], to track protein synthesis of two genes simultaneously (Methods). Genome editing was used to insert a PQR-GFP11 and PQR-mCherry11 at the end of the coding sequence of the endogenous human Ribosomal Protein L13A (RPL13A) and Amyloid Precursor Protein (APP) genes, respectively, in HEK293 suspension cells (FIG. 3D). The small size of the PTR reporters at 80 bases facilitated efficient integration into the endogenous genes during CRISPR-Cas9 genome editing. These cells were then co-transfected with GFP1-10 and mCherry1-10 DNA to co-express the two other split fluorescent protein components. Thus, simultaneously imaging of APP protein synthesis in the red channel and RPL13A protein synthesis in the green channel was performed. However, a universal split1-10 fluorescent protein that alters its emission spectra based on binding of different split11 sequences[22] would simplify the number of reagents required to perform multi-color PTR. Reconstitution of Cherry1-10 and Cherry11 peptides in vitro resulted in production of red fluorescence, and this signal increased throughout the duration of the experiment (FIG. 3E). The reconstitution of split Cherry occurred immediately upon addition of Cherry11 peptide, but produced an overall weaker signal compared to split GFP and split Dendra2, indicating potentially sub-optimal conditions for the reconstitution reaction.

Figures 4B, 4C:
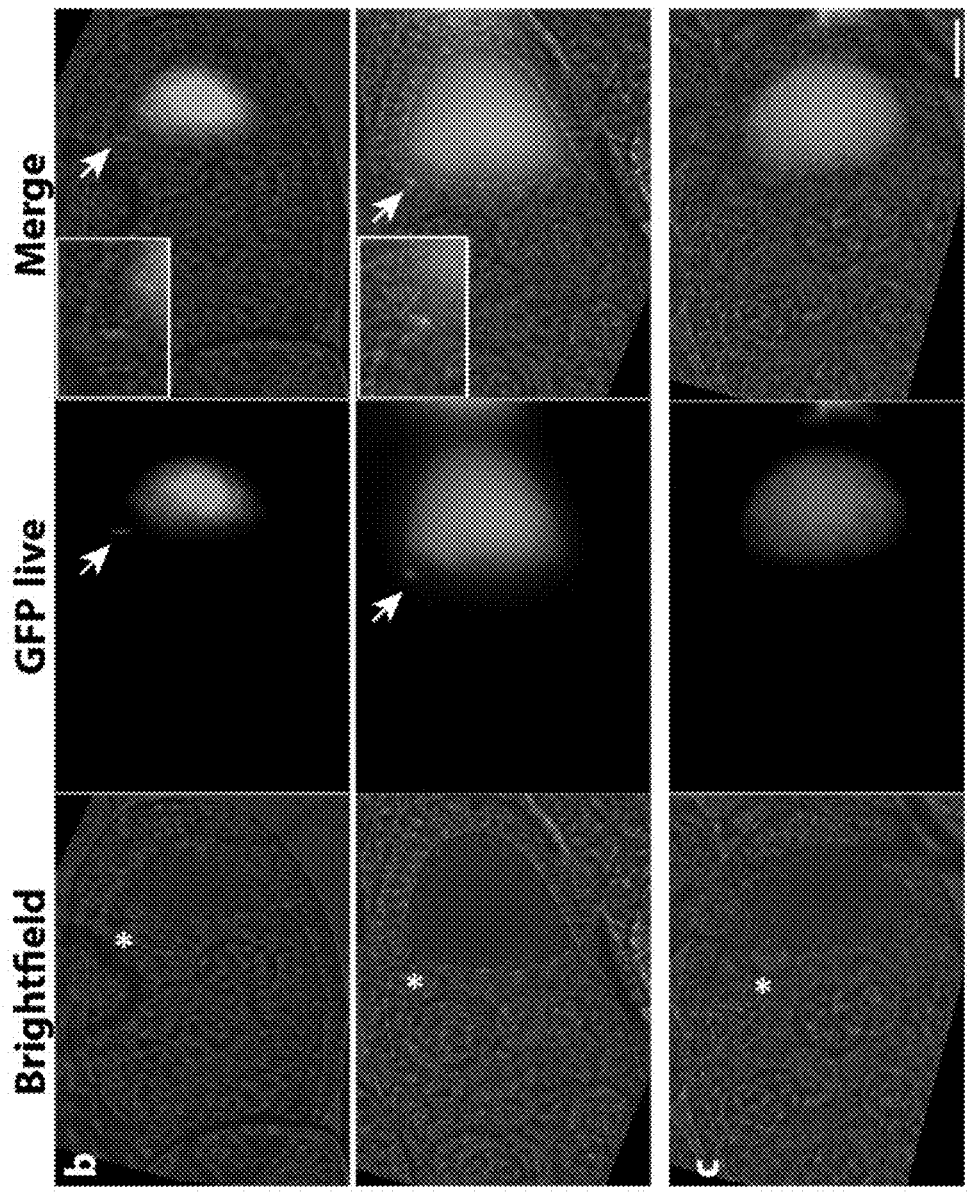
FIG. 4B, relating to direct observation of protein synthesis over time in vivo, are photographs that show representative images of local Gurken translation in *Drosophila* oocytes. Translation of Gurken-PQR-GFP11 produced green fluorescence (arrows) that was always associated within a <5 µm spread in the anterodorsal region near the nucleus (asterisk) in stage 8 (upper panels) and stage 9 (lower panel) oocytes. These results demonstrate the temporal and spatial fidelity of PTR.
FIG. 4C, relating to direct observation of protein synthesis over time in vivo, are photographs that show that animals expressing the Actin>GFP1-10 and containing the UAS-Grk-PQR-GFP11 transgene but without the Gal4 driver did not produce the characteristic signal associated with the oocyte nucleus (n>25). Anterior is left, dorsal is up.
Figure 4D:
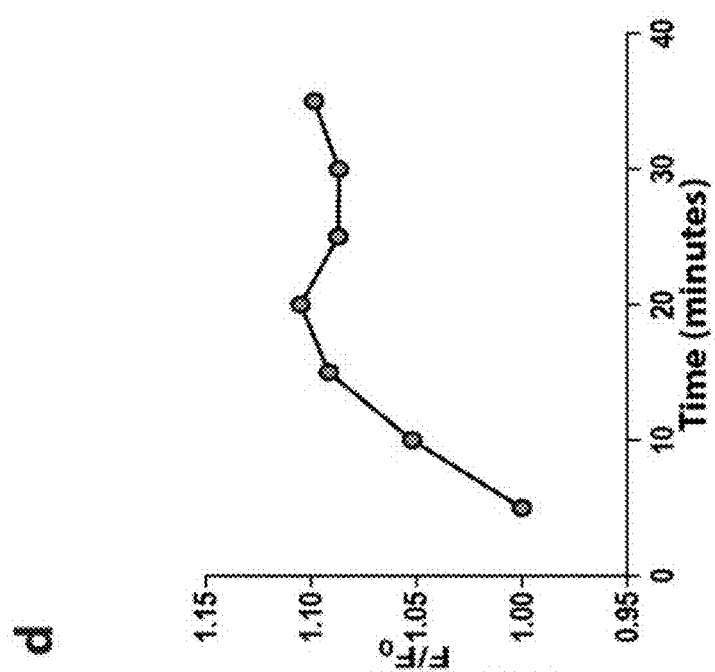
FIG. 4D, relating to direct observation of protein synthesis over time in vivo, is a graph that shows time-series analysis of GFP fluorescence signals observed at the anterior dorsal corner of the oocyte. Oocytes were dissected and imaged over 40 minutes. GFP intensity increased over timescales of minutes in oocytes.

To verify that PTR can detect protein synthesis of spatially-regulated mRNAs, the production of Gurken protein was tracked over time in *Drosophila* oocytes. Synthesis of the Epidermal Growth Factor Receptor ligand Gurken in the anterodorsal corner during the final stages of oocyte maturation specifies the cell fates of only the neighboring follicle cells[33] (FIG. 4A). Transgenic flies were first created that ubiquitously express GFP1-10 from an actin promoter, and flies that express Gurken-PQR-GFP11 under the control of a UAS promoter (Methods, FIG. 4A). The Nanos-Gal4 driver was used to express Gurken-PQR-GFP11 in oocytes from females that expressed all three transgenes. Rapid increases of reconstituted GFP fluorescence were observed in a restricted anterodorsal region from the nucleus over timescales of minutes in the oocytes (FIG. 4B, FIG. 4D). These experiments demonstrate that PTR can quantify localized protein synthesis over time.

Figure 4E:
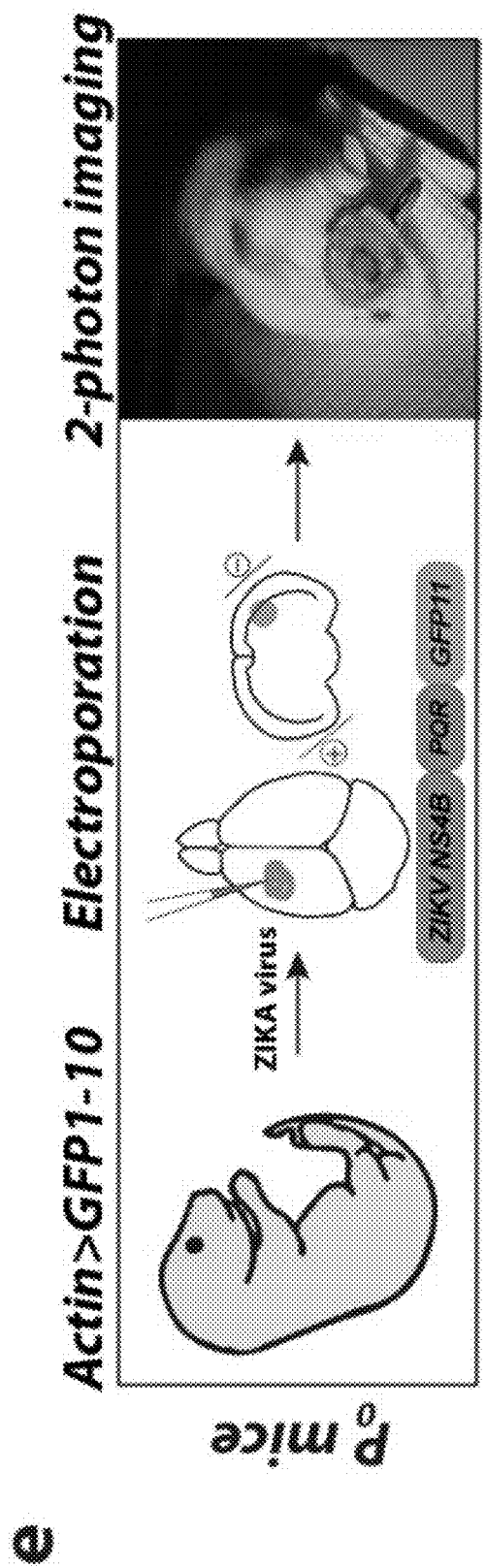
FIG. 4E, relating to direct observation of protein synthesis over time in vivo, is a diagram combined with a photograph that shows a transgenic mouse expressing GFP1-10 under the mammalian Actin promoter (Actin>1-10) was generated to constitutively and ubiquitously express GFP1-10 as in FIG. 4A. Actin>1-10 pups (P0-P1) were injected and electroporated with Asian strain 150989 or African strain Ar41524 ZIKV NS4B-PQR-GFP11 DNA/dye mix (middle panel). Animals were allowed to develop for ~14 days and were then imaged using 2-photon microscopy under anesthesia.
Figures 4F, 4G, 4H, 4I, 4J, 4K:
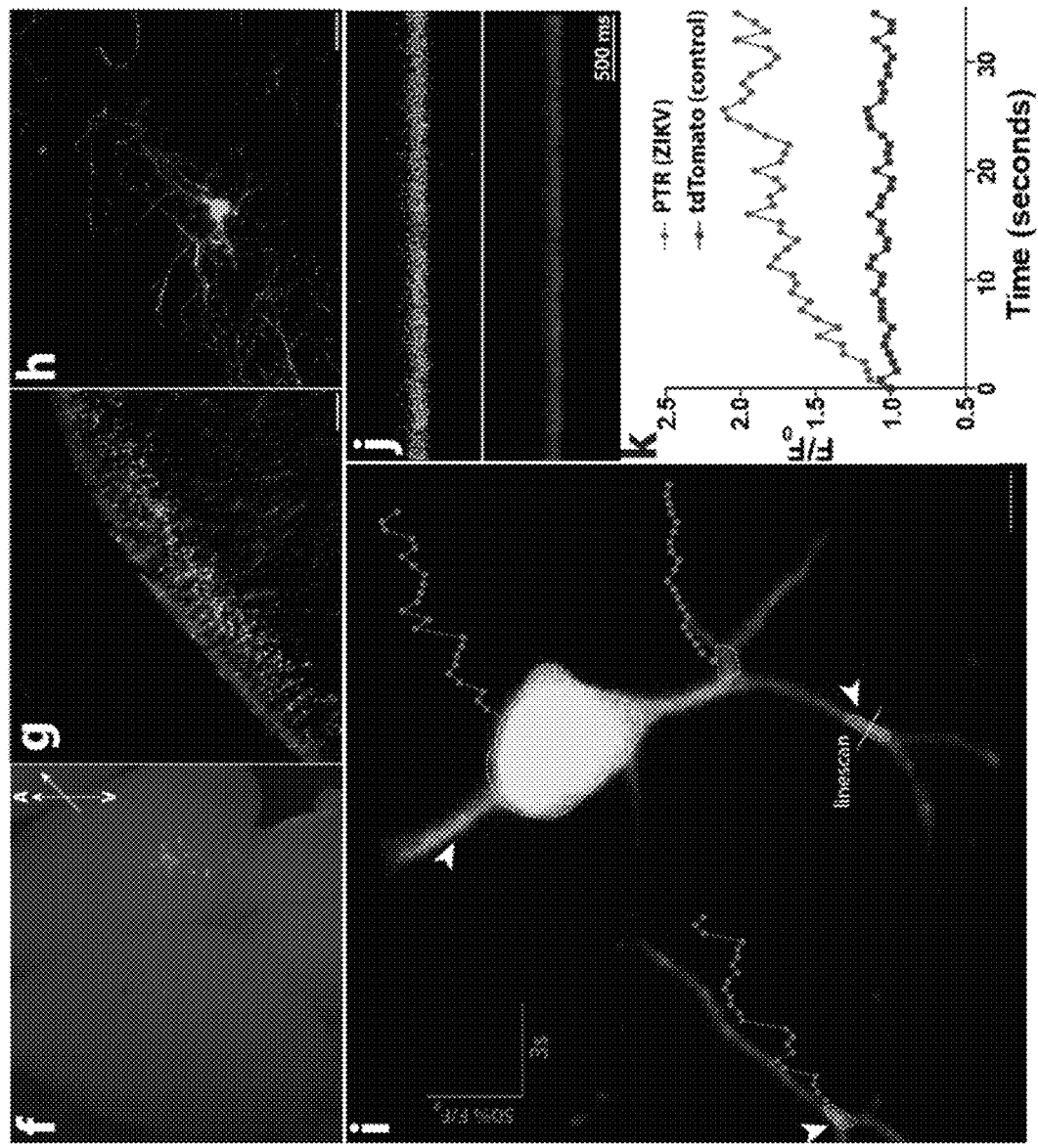
FIGS. 4F-H, relating to direct observation of protein synthesis over time in vivo, are photographs that show that green fluorescence was observed 16 hours post electroporation in the injected cortical regions. DNA injected into the lateral ventricles resulted in GFP reconstitution in progenitors and differentiated cells across cortical layers. Green fluorescence was observed in cell somas and projections, indicating high-level expression of GFP1-10 and ZIKV-PQR-GFP11 proteins.
FIGS. 4I and 4J are photographs and FIG. 4K is a graph, relating to direct observation of protein synthesis over time in vivo, that show time-series analysis of GFP fluorescence signals at different locations along a cell arbor. GFP fluorescence increased over millisecond timescales. Linescans performed at millisecond temporal resolution on different locations along the arbor, shown in grayscale in FIGS. 4I and 4J but corresponding to the green and red channels showed increases in GFP fluorescence but not tdTomato (control plasmid) (representative scanline and scan shown). Arrowheads indicate regions along the arbor where increased NS4B production was observed. Dashed lines delineate the regions of interest used to generate the overlaid traces.

Tracking and quantifying local protein synthesis were sought in neurons in vivo. A transgenic mouse was created that constitutively produces high levels of GFP1-10 protein driven by the actin promoter in all tissues throughout the life of the animal (Methods). PTR with GFP11 was used to examine the protein synthesis dynamics of two strains of the Zika virus (ZIKAV) protein NS4B in the perinatal mouse brain. The Zika virus is an RNA virus that can cause Zika fever in humans, and fetal microcephaly in pregnant humans. In vivo electroporation in neonatal (Postnatal day P0-P1) mice (FIG. 4E) was done to express the NS4B Zika virus protein with PQR-GFP11 flanked by the native 5' and 3' untranslated regions, 5'UTR-NS4B-PQR-GFP11-3'UTR, from either the African Ar41524 or Asian 15098 strain. Co-electroporation of a DNA plasmid of the red fluorescence protein tdTomato was used as a cellular marker and its production dynamics to compare traditional and PTR-based reporters. Green fluorescence in cell somas and neurites was observed as early as 16 hours post electroporation (FIG. 4F FIG. 4H). This indicated that GFP11 peptides were co-produced with the viral NS4B protein and that sufficient GFP1-10 protein was being produced under the Actin promoter in the transgenic mice. Using 2-photon laser scanning microscopy, the in vivo production of NS4B protein was tracked in neurons by measuring changes in green fluorescence over time (FIG. 4I, FIG. 4K). Images were acquired at varying time intervals (400 milliseconds to 5 minutes) to verify that the time course of fluorescence signals were not due to changes in animal movement, position, photobleaching or imaging depth (FIG. 4K, FIG. 4M). Bursts of NS4B protein synthesis were observed over seconds to minutes, and different subcellular locations. For example, local increases of fluorescence intensity were found at perinuclear regions and along proximal dendrites (arrowheads in FIG. 4E). Localized increases were also observed in protein synthesis within dendrites, and linescan imaging across these spots showed increases in GFP fluorescence over milliseconds (FIG. 4J). Importantly, over these timescales no significant changes in tdTomato red fluorescence were observed, which demonstrates the temporal and spatial sensitivity of PTR over traditional reporters in vivo (FIG. 4K). Comparing the rates of ZIKV NS4B protein synthesis between the Asian and African strains was performed by analyzing the temporal spread of the protein synthesis burst events.

Our results using PTR to examine differences in local protein synthesis in the living animal demonstrate its applicability as an infectious disease model in addition to examining dendritic protein synthesis. Multi-color subcellular imaging of local protein synthesis can be useful in examining pathogen-host interactions, related genes and pathways, or different parental alleles. Disease and traits that are associated with a specific allele can be imaged throughout a single neuron to reveal molecular asymmetries or cellular heterogeneities globally across an organ in the living animal.

Protein synthesis of a PQR-GFP11 reporter requires approximately 2 seconds (6 amino acids/second)[36,37]. In the presence of GFP1-10, the split proteins recombine in milliseconds to emit a quantitative green fluorescence signal to indicate the time and location of protein translation within the cell. Synthesis of the GFP11 peptide requires ~3 seconds from the moment of initiation of GFP11 translation and the reconstitution and emission of fluorescence. Whether or not the upstream protein diffuses away from the site of translation, translation of GFP11 will mark the original site of mRNA translation, unless the RNA-bound ribosome diffuses away. Ribosome diffusion in cytoplasm is 0.04 $\mu m2/sec^{28}$, and thus the 3 second delays in detecting the initial protein translation even will produce a spatial error of ~350 nm. Our results suggest that the kinetics and efficiency of the reconstitution reaction can be improved, as different variants of the GFP11 peptide produced different rates of reconstitution. Minor differences in the solubility, charge and size of the GFP11 peptide can affect the rate and efficiency of reconstitution, and ultimately the properties of the reconstituted protein. Therefore, screening for GFP11 peptides that result in the most sensitive reconstitution will certainly improve this technique in the context of monitoring local protein translation events. Split XFP components that fail to reconstitute, or reconstitute but fail to fluoresce can affect the spatial, temporal and quantitative accuracy of the PTR reporters. Even though such problems in the experiments were not observed herein, their occurrence is difficult to predict or estimate in vivo. However, the finding that different variants of GFP11 reconstitute differently suggests that undiscovered split GFP, Dendra2, and Cherry variants may possibly outperform currently available ones.

Although the invention has been described with reference to preferred embodiments, it is to be understood that modifications may be resorted to as will be apparent to those skilled in the art. Such modifications and variations are to be considered within the purview and scope of the present invention.

Representative, non-limiting examples of the present invention were described above in detail with reference to the attached drawing. This detailed description is merely intended to teach a person of skill in the art further details for practicing preferred aspects of the present teachings and is not intended to limit the scope of the invention. Furthermore, each of the additional features and teachings disclosed above and below may be utilized separately or in conjunction with other features and teachings.

Moreover, combinations of features and steps disclosed in the above detailed description, as well as in the experimental examples, may not be necessary to practice the invention in the broadest sense, and are instead taught merely to particularly describe representative examples of the invention. Furthermore, various features of the above-described representative examples, as well as the various independent and dependent claims below, may be combined in ways that are not specifically and explicitly enumerated in order to provide additional useful embodiments of the present teachings.

REFERENCES

1. Dahm, R., Zeitelhofer, M., Gotze, B., Kiebler, M. A. & Macchi, P. Visualizing mRNA localization and local protein translation in neurons. *Methods in cell biology* 85, 293-327, doi:10.1016/S0091-679X (08)85013-3 (2008).
2. Hinz, F. I., Dieterich, D. C. & Schuman, E. M. Teaching old NCATs new tricks: using non-canonical amino acid tagging to study neuronal plasticity. *Current opinion in chemical biology* 17, 738-746, doi:10.1016/j.cbpa.2013.07.021 (2013).
3. Wang, C., Han, B., Zhou, R. & Zhuang, X. Real-Time Imaging of Translation on Single mRNA Transcripts in Live Cells. *Cell* 165, 990-1001, doi:10.1016/j.cell.2016.04.040 (2016).
4. Yan, X., Hoek, T. A., Vale, R. D. & Tanenbaum, M. E. Dynamics of Translation of Single mRNA Molecules In Vivo. *Cell* 165, 976-989, doi:10.1016/j.cell.2016.04.034 (2016).
5. Na, Y. et al. Real-Time Imaging Reveals Properties of Glutamate-Induced Arc/Arg 3.1 Translation in Neuronal Dendrites. *Neuron* 91, 561-573, doi:10.1016/j.neuron.2016.06.017 (2016).
6. Palmer E, Freeman T. Investigation into the use of C- and N-terminal GFP fusion proteins for subcellular localization studies using reverse transfection microarrays. *Comp Funct Genomics.* doi:10.1002/cfg.405, 2004; 5(4): 342-353
7. Zhao, H. L., Yao, X. Q., Xue, C., Wang, Y., Xiong, X. H., & Liu, Z. M. (2008). Increasing the homogeneity, stability and activity of human serum albumin and interferon-alpha2b fusion protein by linker engineering. Protein Expression and Purification, 61(1), 73-7.
8. Craig F F, Simmonds A C, Watmore D, McCapra F, White M R. Membrane-permeable luciferin esters for assay of firefly luciferase in live intact cells. *Biochem J.* 1991; 276 (Pt 3)(Pt 3):637-641. doi:10.1042/bj2760637
9. Morse, D., & Tannous, B. A. (2012). A water-soluble coelenterazine for sensitive in vivo imaging of coelenterate luciferases. Molecular Therapy: The Journal of the American Society of Gene Therapy, 20(4), 692-3.
10. Tanenbaum M E, Gilbert L A, Qi L S, Weissman J S, Vale R D. A protein-tagging system for signal amplification in gene expression and fluorescence imaging. *Cell.* 2014; 159(3):635-646. doi:10.1016/j.cell.2014.09.039
11. Zhao N, Kamijo K, Fox P D, et al. A genetically encoded probe for imaging nascent and mature HA-tagged proteins in vivo. *Nat Commun.* 2019; 10(1):2947. Published 2019 Jul. 3. doi:10.1038/s41467-019-10846-1
12. Snapp, E. (2005). Design and use of fluorescent fusion proteins in cell biology. Current Protocols in Cell. Chapter 21, Unit 156 21.4.
13. Yang H, Liu L, Xu F. The promises and challenges of fusion constructs in protein biochemistry and enzymology. Applied Microbiology and Biotechnology. 100 (19): 8273-81. (2016)
14. Lo, C.-A. et al. Quantification of Protein Levels in Single Living Cells. *Cell Reports* 13, 2634-2644, doi:10.1016/j.celrep.2015.11.048 (2015).
15. Iizuka, R., Yamagishi-Shirasaki, M. & Funatsu, T. Kinetic study of de novo chromophore maturation of fluorescent proteins. *Analytical biochemistry* 414, 173-178, doi:10.1016/j.ab.2011.03.036 (2011).
16. Shaner, N. C., Steinbach, P. A. & Tsien, R. Y. A guide to choosing fluorescent proteins. *Nat Methods* 2, 905-909, doi:10.1038/nmeth819 (2005).
17. Feinberg, E. H. et al. GFP Reconstitution Across Synaptic Partners (GRASP) defines cell contacts and synapses in living nervous systems. Neuron 57, 353-363, doi:10.1016/j.neuron.2007.11.030 (2008).
18. Kerppola, T. K. Visualization of molecular interactions by fluorescence complementation. *Nature reviews. Molecular cell biology* 7, 449-456, doi:10.1038/nrm1929 (2006).
19. Pedelacq, J. D., Cabantous, S., Tran, T., Terwilliger, T. C. & Waldo, G. S. Engineering and characterization of a superfolder green fluorescent protein. *Nature biotechnology* 24, 79-88, doi:10.1038/nbt1172 (2006).
20. Kim, J. et al. mGRASP enables mapping mammalian synaptic connectivity with light microscopy. *Nat Methods* 9, 96-102, doi:10.1038/nmeth.1784 (2011).
21. Yamagata, M. & Sanes, J. R. Transgenic strategy for identifying synaptic connections in mice by fluorescence complementation (GRASP). *Front Mol Neurosci* 5, 18, doi:10.3389/fnmol.2012.00018 (2012).
22. Do, K. & Boxer, S. G. Thermodynamics, kinetics, and photochemistry of beta-strand association and dissociation in a split-GFP system. *J Am Chem Soc* 133, 18078-18081, doi:10.1021/ja207985w (2011).
23. Kent, K. P. & Boxer, S. G. Light-activated reassembly of split green fluorescent protein. *J Am Chem Soc* 133, 4046-4052, doi:10.1021/ja110256c (2011).
24. Huang, Y. M. & Bystroff, C. Complementation and reconstitution of fluorescence from circularly permuted and truncated green fluorescent protein. *Biochemistry* 48, 929-940, doi:10.1021/bi802027g (2009).
25. Ingolia, N. T., Lareau, L. F. & Weissman, J. S. Ribosome profiling of mouse embryonic stem cells reveals the complexity and dynamics of mammalian proteomes. *Cell* 147, 789-802, doi:10.1016/j.cell.2011.10.002 (2011).
26. Karpinets, T. V., Greenwood, D. J., Sams, C. E. & Ammons, J. T. RNA:protein ratio of the unicellular organism as a characteristic of phosphorous and nitrogen stoichiometry and of the cellular requirement of ribosomes for protein synthesis. *BMC Biol* 4, 30, doi:10.1186/1741-7007-4-30 (2006).
27. Einstein, A. Über die von der molekularkinetischen Theorie der Wärme geforderte Bewegung von in ruhenden Flüssigkeiten suspendierten Teilchen. *Annalen der Physik* 322, 549-560, doi:10.1002/andp.19053220806 (1905).
28. Bakshi, S., Siryaporn, A., Goulian, M. & Weisshaar, J. C. Superresolution imaging of ribosomes and RNA polymerase in live *Escherichia coli* cells. *Mol Microbiol* 85, 21-38, doi:10.1111/j.1365-2958.2012.08081.x (2012).
29. Chudakov, D. M., Lukyanov, S. & Lukyanov, K. A. Using photoactivatable fluorescent protein Dendra2 to track protein movement. *Biotechniques* 42, 553, 555, 557 passim (2007).
30. Kays, I., & Chen, B. E. Protein and RNA quantification of multiple genes in single cells. *BioTechniques,* 66(1), 15-21. doi: 10.2144/btn-2018-0130. (2019).
31. Lo, C.-A. & Chen, B. E. Parental Allele-Specific Protein Expression Over Time in Single Cells In Vivo. Co-submitted (2017).
32. Fan, J. Y. et al. Split mCherry as a new red bimolecular fluorescence complementation system for visualizing protein-protein interactions in living cells. *Biochemical and biophysical research communications* 367, 47-53, doi: 10.1016/j.bbrc.2007.12.101. (2008).
33. Nilson, L. A. & Schupbach, T. EGF receptor signaling in *Drosophila* oogenesis. *Curr Top Dev Biol* 44, 203-243 (1999).
36. Kramer, G., Boehringer, D., Ban, N., & Bukau, B. The ribosome as a platform for cotranslational processing, folding and targeting of newly synthesized proteins. Nature Structural & Molecular Biology, 16(6), 589-597. (2009).

37. Ross, J. F., & Orlowski, M. (1982). Growth-rate-dependent adjustment of ribosome function in 155 chemostat-grown cells of the fungus *Mucor racemosus*. Journal of Bacteriology, 149(2), 650-3.

What is claimed is:

1. A method of quantifying expression of a protein of interest with high temporal resolution comprising:
   a) providing a cell expressing a large fragment of a split fluorescent protein, wherein the large fragment of the split fluorescent protein does not fluoresce until the large fragment of the split fluorescent protein associates with a corresponding small portion of the split fluorescent protein;
   b) transfecting the cell with a vector comprising a nucleic acid molecule comprising:
      i) a first nucleic acid sequence encoding the protein of interest;

ii) a second nucleic acid sequence encoding the small fragment of the split fluorescent protein; and iii) a third nucleic acid sequence encoding a protein translation (PTA) linker protein comprising a protein quantification reporter (PQR) portion that is cleaved during translation and an inert portion;

wherein at least the nucleic acid sequence encoding the PQR portion of the PTR linker protein is located between the nucleic add sequence encoding the protein of interest and the nucleic add sequence encoding the small fragment of the split fluorescent protein;

c) expressing the nucleic add molecule of b) in said cell, wherein the protein of interest and the small fragment of the split fluorescent protein are cleaved apart at the PQR portion of the PTR linker protein, resulting in a stochiometric ratio of the small fragment of the split fluorescent protein and protein of interest; and d) quantifying expression of the protein of interest by detecting fluorescence produced when the large fragment of the split fluorescent protein and the small fragment of the split fluorescent protein associate.

2. The method as defined in claim 1, wherein the nucleic add sequence encoding the PQR portion and the inert portion of the PTR linker protein are located between the nucleic acid sequence encoding the protein of interest and the nucleic acid sequence encoding the small fragment of the split fluorescent protein.

3. The method as defined in claim 1, wherein the nucleic acid sequence encoding the PQR portion of the PTR linker protein is located between the nucleic acid sequence encoding the protein of interest and the nucleic acid sequence encoding the small fragment of the split fluorescent protein, and wherein the nucleic acid sequence encoding inert portion of the PTR linker protein is located at the opposite end of to the nucleic acid sequence encoding the small fragment of the split fluorescent protein from the nucleic acid sequence encoding a FOR portion of the PTR linker protein.

4. The method as defined in claim 1, wherein the nucleic acid molecule is a deoxyribonucleic acid molecule.

5. The method as defined in claim 1, wherein the cell is part of an organism comprising many of the cells.

6. The method as defined in claim 1, wherein the quantifying is performed using a linear regression technique.

7. The method as defined in claim 1, wherein the nucleic acid sequence encoding the PQR portion of the PTR linker encodes amino acid sequence SEQ ID NO: 26 or 27.

8. A nucleic acid molecule encoding a small fragment of a split Dendra fluorescent protein comprising a nucleic acid sequence of SEQ ID NO. 22, wherein the small fragment of the split Dendra fluorescent protein is configured to associate with a large fragment of the split Dendra fluorescent protein to fluoresce.

9. A method of generating fluorescence comprising transfecting a cell with a vector comprising the nucleic acid molecule of claim 8, wherein said cell expresses a large fragment of the split Dendra fluorescent protein, and wherein fluorescence is generated when the small fragment of the split Dendra fluorescent protein is translated within the cell and combines with the large fragment of the split Dendra fluorescent protein.

* * * * *

```
                              SEQUENCE LISTING

<160> NUMBER OF SEQ ID NOS: 84

<210> SEQ ID NO 1
<211> LENGTH: 216
<212> TYPE: PRT
<213> ORGANISM: Artificial Sequence
<220> FEATURE:
<223> OTHER INFORMATION: GFP1-10

<400> SEQUENCE: 1

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Arg Gly Glu
            20                  25                  30

Gly Glu Gly Asp Ala Thr Ile Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Thr Tyr Gly Val Gln Cys Phe Ser Arg Tyr Pro Asp His Met Lys Arg
65                  70                  75                  80

His Asp Phe Phe Lys Ser Ala Met Pro Glu Gly Tyr Val Gln Glu Arg
                85                  90                  95

Thr Ile Ser Phe Lys Asp Asp Gly Lys Tyr Lys Thr Arg Ala Val Val
            100                 105                 110

Lys Phe Glu Gly Asp Thr Leu Val Asn Arg Ile Glu Leu Lys Gly Thr
        115                 120                 125

Asp Phe Lys Glu Asp Gly Asn Ile Leu Gly His Lys Leu Glu Tyr Asn
    130                 135                 140

Phe Asn Ser His Asn Val Tyr Ile Thr Ala Asp Lys Gln Lys Asn Gly
145                 150                 155                 160

Ile Lys Ala Asn Phe Thr Val Arg His Asn Val Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Thr Val Leu Ser
        195                 200                 205

Lys Asp Pro Asn Glu Lys Gly Thr
    210                 215

<210> SEQ ID NO 2
<211> LENGTH: 214
<212> TYPE: PRT
<213> ORGANISM: Artificial Sequence
<220> FEATURE:
<223> OTHER INFORMATION: GFP1-10

<400> SEQUENCE: 2

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Arg Gly Glu
            20                  25                  30

Gly Glu Gly Asp Ala Thr Ile Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60
```

-continued

Thr Tyr Gly Val Gln Cys Phe Ser Arg Tyr Pro Asp His Met Lys Arg
 65                  70                  75                  80

His Asp Phe Phe Lys Ser Ala Met Pro Glu Gly Tyr Val Gln Glu Arg
                 85                  90                  95

Thr Ile Ser Phe Lys Asp Asp Gly Lys Tyr Lys Thr Arg Ala Val Val
            100                 105                 110

Lys Phe Glu Gly Asp Thr Leu Val Asn Arg Ile Glu Leu Lys Gly Thr
        115                 120                 125

Asp Phe Lys Glu Asp Gly Asn Ile Leu Gly His Lys Leu Glu Tyr Asn
130                 135                 140

Phe Asn Ser His Asn Val Tyr Ile Thr Ala Asp Lys Gln Lys Asn Gly
145                 150                 155                 160

Ile Lys Ala Asn Phe Thr Val Arg His Asn Val Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Thr Val Leu Ser
        195                 200                 205

Lys Asp Pro Asn Glu Lys
    210

<210> SEQ ID NO 3
<211> LENGTH: 17
<212> TYPE: PRT
<213> ORGANISM: Artificial Sequence
<220> FEATURE:
<223> OTHER INFORMATION: GFP11

<400> SEQUENCE: 3

Met Arg Asp His Met Val Leu Leu Glu Phe Val Thr Ala Ala Gly Ile
1               5                   10                  15

Thr

<210> SEQ ID NO 4
<211> LENGTH: 17
<212> TYPE: PRT
<213> ORGANISM: Artificial Sequence
<220> FEATURE:
<223> OTHER INFORMATION: GFP11

<400> SEQUENCE: 4

Met Arg Asp His Met Val Leu Leu Glu Phe Val Thr Ala Ala Gly Ile
1               5                   10                  15

Thr

<210> SEQ ID NO 5
<211> LENGTH: 17
<212> TYPE: PRT
<213> ORGANISM: Artificial Sequence
<220> FEATURE:
<223> OTHER INFORMATION: GFP11

<400> SEQUENCE: 5

Met Arg Asp His Met Val Leu His Glu Phe Val Thr Ala Ala Gly Ile
1               5                   10                  15

Thr

-continued

<210> SEQ ID NO 6
<211> LENGTH: 17
<212> TYPE: PRT
<213> ORGANISM: Artificial Sequence
<220> FEATURE:
<223> OTHER INFORMATION: GFP11

<400> SEQUENCE: 6

Met Arg Asp His Met Val Leu His Glu Phe Val Thr Ala Ala Gly Ile
1               5                   10                  15

Thr

<210> SEQ ID NO 7
<211> LENGTH: 17
<212> TYPE: PRT
<213> ORGANISM: Artificial Sequence
<220> FEATURE:
<223> OTHER INFORMATION: GFP11

<400> SEQUENCE: 7

Met Arg Asp His Met Val Leu His Glu Tyr Val Asn Ala Ala Gly Ile
1               5                   10                  15

Thr

<210> SEQ ID NO 8
<211> LENGTH: 230
<212> TYPE: PRT
<213> ORGANISM: Artificial Sequence
<220> FEATURE:
<223> OTHER INFORMATION: Dendra1-10

<400> SEQUENCE: 8

Met Asn Thr Pro Gly Ile Asn Leu Ile Lys Glu Asp Met Arg Val Lys
1               5                   10                  15

Val His Met Glu Gly Asn Val Asn Gly His Ala Phe Val Ile Glu Gly
                20                  25                  30

Glu Gly Lys Gly Lys Pro Tyr Glu Gly Thr Gln Thr Ala Asn Leu Thr
            35                  40                  45

Val Lys Glu Gly Ala Pro Leu Pro Phe Ser Tyr Asp Ile Leu Thr Thr
    50                  55                  60

Ala Val His Tyr Gly Asn Arg Val Phe Thr Lys Tyr Pro Glu Asp Ile
65                  70                  75                  80

Pro Asp Tyr Phe Lys Gln Ser Phe Pro Glu Gly Tyr Ser Trp Glu Arg
                85                  90                  95

Thr Met Thr Phe Glu Asp Lys Gly Ile Cys Thr Ile Arg Ser Asp Ile
            100                 105                 110

Ser Leu Glu Gly Asp Cys Phe Phe Gln Asn Val Arg Phe Lys Gly Thr
        115                 120                 125

Asn Phe Pro Pro Asn Gly Pro Val Met Gln Lys Lys Thr Leu Lys Trp
    130                 135                 140

Glu Pro Ser Thr Glu Lys Leu His Val Arg Asp Gly Leu Leu Val Gly
145                 150                 155                 160

Asn Ile Asn Met Ala Leu Leu Leu Glu Gly Gly Gly His Tyr Leu Cys
                165                 170                 175

Asp Phe Lys Thr Thr Tyr Lys Ala Lys Lys Val Val Gln Leu Pro Asp
            180                 185                 190

Ala His Phe Val Asp His Arg Ile Glu Ile Leu Gly Asn Asp Ser Asp
        195                 200                 205

```
Tyr Asn Lys Val Lys Leu Tyr Glu His Ala Val Ala Arg Tyr Ser Pro
            210                 215                 220
Leu Pro Ser Gln Val Trp
225                 230

<210> SEQ ID NO 9
<211> LENGTH: 41
<212> TYPE: PRT
<213> ORGANISM: Artificial Sequence
<220> FEATURE:
<223> OTHER INFORMATION: Dendra11

<400> SEQUENCE: 9

Met Pro Asp Ala His Phe Val Asp His Arg Ile Glu Ile Leu Gly Asn
1               5                   10                  15
Asp Ser Asp Tyr Asn Lys Val Lys Leu Tyr Glu His Ala Val Ala Arg
            20                  25                  30
Tyr Ser Pro Leu Pro Ser Gln Val Trp
        35                  40

<210> SEQ ID NO 10
<211> LENGTH: 208
<212> TYPE: PRT
<213> ORGANISM: Artificial Sequence
<220> FEATURE:
<223> OTHER INFORMATION: Cherry1-10

<400> SEQUENCE: 10

Met Glu Glu Asp Asn Met Ala Ile Ile Lys Glu Phe Met Arg Phe Lys
1               5                   10                  15
Val His Met Glu Gly Ser Val Asn Gly His Glu Phe Glu Ile Glu Gly
            20                  25                  30
Glu Gly Glu Gly His Pro Tyr Glu Gly Thr Gln Thr Ala Lys Leu Lys
        35                  40                  45
Val Thr Lys Gly Gly Pro Leu Pro Phe Ala Trp Asp Ile Leu Ser Pro
50                  55                  60
Gln Phe Met Tyr Gly Ser Lys Ala Tyr Val Lys His Pro Ala Asp Ile
65                  70                  75                  80
Pro Asp Tyr Leu Lys Leu Ser Phe Pro Glu Gly Phe Thr Trp Glu Arg
                85                  90                  95
Val Met Asn Phe Glu Asp Gly Gly Val Val Thr Val Thr Gln Asp Ser
            100                 105                 110
Ser Leu Gln Asp Gly Glu Phe Ile Tyr Lys Val Lys Leu Leu Gly Thr
        115                 120                 125
Asn Phe Pro Ser Asp Gly Pro Val Met Gln Lys Lys Thr Met Gly Trp
130                 135                 140
Glu Ala Ser Thr Glu Arg Met Tyr Pro Glu Asp Gly Ala Leu Lys Gly
145                 150                 155                 160
Glu Ile Asn Gln Arg Leu Lys Leu Lys Asp Gly Gly His Tyr Asp Ala
                165                 170                 175
Glu Val Lys Thr Thr Tyr Lys Ala Lys Lys Pro Val Gln Leu Pro Gly
            180                 185                 190
Ala Tyr Asn Val Asp Ile Lys Leu Asp Ile Thr Ser His Asn Glu Asp
        195                 200                 205

<210> SEQ ID NO 11
<211> LENGTH: 19
<212> TYPE: PRT
<213> ORGANISM: Artificial Sequence
```

<220> FEATURE:
<223> OTHER INFORMATION: Cherry11

<400> SEQUENCE: 11

Met Tyr Thr Ile Val Glu Gln Tyr Glu Arg Ala Glu Gly Arg His Ser
1               5                   10                  15

Thr Gly Gly

<210> SEQ ID NO 12
<211> LENGTH: 17
<212> TYPE: PRT
<213> ORGANISM: Artificial Sequence
<220> FEATURE:
<223> OTHER INFORMATION: Cherry11

<400> SEQUENCE: 12

Met Tyr Thr Ile Val Glu Gln Tyr Glu Arg Ala Glu Ala Arg His Ser
1               5                   10                  15

Thr

<210> SEQ ID NO 13
<211> LENGTH: 651
<212> TYPE: DNA
<213> ORGANISM: Artificial Sequence
<220> FEATURE:
<223> OTHER INFORMATION: Oligonucleotide

<400> SEQUENCE: 13
atgtccaagg gagaagagtt gtttactggc gtagtccta ttctcgtgga actcgatggt      60
gacgtgaatg gccataagtt ttctgtcaga ggagagggag aaggcgatgc caccatcggg    120
aaactcacgc tgaaattcat ctgtaccact ggaaaacttc ccgtgccttg gccaaccctc    180
gtgacaacac tcacctacgg ggtgcaatgt ttctctcggt acccggacca tatgaagagg    240
catgacttct tcaagagtgc catgcccgag ggttacgttc aggagcgcac catctctttt    300
aaggacgatg gcaaatataa gacaagagca gtcgtcaagt tcgagggtga tacactcgtt    360
aaccgcatcg agctcaaagg caccgatttt aaggaggacg gaaatatcct gggacacaaa    420
ttggagtaca acttcaacag tcacaacgtg tatattacag cagataagca gaagaatggc    480
ataaaggcca atttcacggt aagacataat gtcgaggatg gcagtgtcca gctggcagac    540
cactaccagc aaaacacgcc cattggcgat ggacctgttc tcctgccaga caaccactac    600
ctcagtaccc aaacagtcct gtccaaggac cctaatgaga agggacgtg a              651

<210> SEQ ID NO 14
<211> LENGTH: 645
<212> TYPE: DNA
<213> ORGANISM: Artificial Sequence
<220> FEATURE:
<223> OTHER INFORMATION: Oligonucleotide

<400> SEQUENCE: 14
atgtccaaag gagaagaact gtttaccggt gttgtgccaa ttttggttga actcgatggt      60
gatgtcaacg gacataagtt ctcagtgaga ggcgaaggag aaggtgacgc caccattgga    120
aaattgactc ttaaattcat ctgtactact ggtaaacttc ctgtaccatg gccgactctc    180
gtaacaacgc ttacgtacgg agttcagtgc ttttcgagat acccagacca tatgaaaaga    240
catgactttt ttaagtcggc tatgcctgaa ggttacgtgc aagaaagaac aatttcgttc    300
aaagatgatg gaaaatataa aactagagca gttgttaaat tgaaggaga tactttggtt    360

| | | |
|---|---|---|
| aaccgcattg aactgaaagg aacagatttt aaagaagatg gtaatattct tggacacaaa | 420 | |
| ctcgaataca attttaatag tcataacgta tacatcactg ctgataagca aaagaacgga | 480 | |
| attaaagcga atttcacagt acgccataat gtagaagatg gcagtgttca acttgccgac | 540 | |
| cattaccaac aaaacacccc tattggagac ggtccggtac ttcttcctga taatcactac | 600 | |
| ctctcaacac aaacagtcct gagcaaagat ccaaatgaaa aatga | 645 | |

```
<210> SEQ ID NO 15
<211> LENGTH: 54
<212> TYPE: DNA
<213> ORGANISM: Artificial Sequence
<220> FEATURE:
<223> OTHER INFORMATION: Oligonucleotide

<400> SEQUENCE: 15
```

| | |
|---|---|
| atgcgagacc acatggtctt gcttgaattc gtaacagcag cggggatcac ttga | 54 |

```
<210> SEQ ID NO 16
<211> LENGTH: 54
<212> TYPE: DNA
<213> ORGANISM: Artificial Sequence
<220> FEATURE:
<223> OTHER INFORMATION: Oligonucleotide

<400> SEQUENCE: 16
```

| | |
|---|---|
| atgagggacc acatggtcct cctggaattc gtaaccgcag ccggtatcac ctga | 54 |

```
<210> SEQ ID NO 17
<211> LENGTH: 54
<212> TYPE: DNA
<213> ORGANISM: Artificial Sequence
<220> FEATURE:
<223> OTHER INFORMATION: Oligonucleotide

<400> SEQUENCE: 17
```

| | |
|---|---|
| atgcgtgacc atatggtgtt gcacgagttc gtcaccgctg ctggtatcac ctga | 54 |

```
<210> SEQ ID NO 18
<211> LENGTH: 54
<212> TYPE: DNA
<213> ORGANISM: Artificial Sequence
<220> FEATURE:
<223> OTHER INFORMATION: Oligonucleotide

<400> SEQUENCE: 18
```

| | |
|---|---|
| atgagagatc atatggttct ccacgagttc gtaactgcag ctgggatcac ttga | 54 |

```
<210> SEQ ID NO 19
<211> LENGTH: 53
<212> TYPE: DNA
<213> ORGANISM: Artificial Sequence
<220> FEATURE:
<223> OTHER INFORMATION: Oligonucleotide

<400> SEQUENCE: 19
```

| | |
|---|---|
| atggtgacca catggtcctc catgagtacg ttaatgctgc gggcatcacc taa | 53 |

```
<210> SEQ ID NO 20
<211> LENGTH: 54
<212> TYPE: DNA
<213> ORGANISM: Artificial Sequence
<220> FEATURE:
<223> OTHER INFORMATION: Oligonucleotide
```

<400> SEQUENCE: 20
atgcgagacc acatggtgct gcatgagtac gtcaacgcag ccggtattac gtaa            54

<210> SEQ ID NO 21
<211> LENGTH: 693
<212> TYPE: DNA
<213> ORGANISM: Artificial Sequence
<220> FEATURE:
<223> OTHER INFORMATION: Oligonucleotide

<400> SEQUENCE: 21
atgaacaccc cgggaattaa cctgatcaag gaggacatgc gcgtgaaggt gcacatggag       60
ggcaacgtga acggccacgc cttcgtgatc gagggcgagg gcaagggcaa gccctacgag      120
ggcacccaga ccgccaacct gaccgtgaag gagggcgccc ccctgccctt cagctacgac      180
atcctgacca ccgccgtgca ctacggcaac cgggtgttca ccaagtaccc cgaggacatc      240
cccgactact tcaagcagag cttccccgag ggctacagct gggagcgcac catgaccttc      300
gaggacaagg gcatctgcac catccgcagc gacatcagct ggagggcga ctgcttcttc       360 cagaacgtgc gcttcaaggg caccaacttc cccccaacg ccccgtgat gcagaagaag        420 accctgaagt gggagcccag caccgagaag ctgcacgtgc gcgacggcct gctggtgggc      480
aacatcaaca tggccctgct gctggagggc ggcggccact acctgtgcga cttcaagacc      540
acctacaagg ccaagaaggt ggtgcagctg cccgacgccc acttcgtgga ccaccgcatc      600
gagatcctgg gcaacgacag cgactacaac aaggtgaagc tgtacgagca cgccgtggcc      660
cgctacagcc ccctgcccag ccaggtgtgg taa                                   693

<210> SEQ ID NO 22
<211> LENGTH: 126
<212> TYPE: DNA
<213> ORGANISM: Artificial Sequence
<220> FEATURE:
<223> OTHER INFORMATION: Oligonucleotide

<400> SEQUENCE: 22
atgcccgacg cccacttcgt ggaccaccgc atcgagatcc tgggcaacga cagcgactac       60
aacaaggtga agctgtacga gcacgccgtg cccgctaca gccccctgcc cagccaggtg       120
tggtga                                                                 126

<210> SEQ ID NO 23
<211> LENGTH: 627
<212> TYPE: DNA
<213> ORGANISM: Artificial Sequence
<220> FEATURE:
<223> OTHER INFORMATION: Oligonucleotide

<400> SEQUENCE: 23
atggaggagg acaacatggc catcatcaag gagttcatga gattcaaggt gcacatggag       60
ggcagcgtga acggccacga gttcgagatc gagggcgagg cgagggcca ccctacgag       120 ggcacccaga ccgccaagct gaaggtgacc aagggcggcc ccctgccctt cgcctgggac      180
atcctgagcc ccagttcat gtacggcagc aaggcctacg tgaagcaccc cgccgacatc       240
cccgactacc tgaagctgag cttccccgag ggcttcacct gggagagagt gatgaacttc      300
gaggacggcg gcgtggtgac cgtgacccag gacagcagcc tgcaggacgg cgagttcatc      360
tacaaggtga agctgctggg caccaacttc cccagcgacg ccccgtgat gcagaagaag       420 accatgggct gggaggccag caccgagaga atgtaccccg aggacggcgc cctgaagggc      480

```
gagatcaacc agagactgaa gctgaaggac ggcggccact acgacgccga ggtgaagacc      540
acctacaagg ccaagaagcc cgtgcagctg cccggcgcct acaacgtgga catcaagctg      600
gacatcacca gccacaacga ggactga                                          627
```

```
<210> SEQ ID NO 24
<211> LENGTH: 60
<212> TYPE: DNA
<213> ORGANISM: Artificial Sequence
<220> FEATURE:
<223> OTHER INFORMATION: Oligonucleotide

<400> SEQUENCE: 24
atgtacacca tcgtggagca gtacgagaga gccgagggca gacacagcac cggcggctga      60
```

```
<210> SEQ ID NO 25
<211> LENGTH: 54
<212> TYPE: DNA
<213> ORGANISM: Artificial Sequence
<220> FEATURE:
<223> OTHER INFORMATION: Oligonucleotide

<400> SEQUENCE: 25
atgtacacca tcgtggagca gtacgagaga gccgaggcca gacacagcac ctga            54
```

```
<210> SEQ ID NO 26
<211> LENGTH: 22
<212> TYPE: PRT
<213> ORGANISM: Artificial Sequence
<220> FEATURE:
<223> OTHER INFORMATION: PQR Portion

<400> SEQUENCE: 26

Gly Ser Gly Ala Thr Asn Phe Ser Leu Leu Lys Gln Ala Gly Asp Val
1               5                   10                  15

Glu Glu Asn Pro Gly Pro
            20
```

```
<210> SEQ ID NO 27
<211> LENGTH: 22
<212> TYPE: PRT
<213> ORGANISM: Artificial Sequence
<220> FEATURE:
<223> OTHER INFORMATION: PQR Portion

<400> SEQUENCE: 27

Gly Ser Gly Ala Thr Asn Phe Ser Leu Leu Lys Gln Ala Gly Asp Val
1               5                   10                  15

Glu Glu Asn Pro Gly Pro
            20
```

```
<210> SEQ ID NO 28
<211> LENGTH: 66
<212> TYPE: DNA
<213> ORGANISM: Artificial Sequence
<220> FEATURE:
<223> OTHER INFORMATION: Oligonucleotide

<400> SEQUENCE: 28
ggaagcggag cgacgaattt tagtctacta aaacaagcgg gtgatgtaga agaaaaccct      60
ggacct                                                                66
```

```
<210> SEQ ID NO 29
<211> LENGTH: 66
<212> TYPE: DNA
<213> ORGANISM: Artificial Sequence
<220> FEATURE:
<223> OTHER INFORMATION: Oligonucleotide

<400> SEQUENCE: 29
ggaagcggag cgacgaattt tagtctacta aaacaagcgg gtgatgtaga agaaaaccct     60
ggacct                                                                66

<210> SEQ ID NO 30
<211> LENGTH: 10
<212> TYPE: PRT
<213> ORGANISM: Artificial Sequence
<220> FEATURE:
<223> OTHER INFORMATION: Inert Portion

<400> SEQUENCE: 30

Gly Gly Gly Ser Gly Gly Gly Ser Val Asp
1               5                   10

<210> SEQ ID NO 31
<211> LENGTH: 12
<212> TYPE: PRT
<213> ORGANISM: Artificial Sequence
<220> FEATURE:
<223> OTHER INFORMATION: Inert Portion

<400> SEQUENCE: 31

Gly Gly Gly Gly Ser Gly Gly Gly Gly Ser Val Asp
1               5                   10

<210> SEQ ID NO 32
<211> LENGTH: 12
<212> TYPE: PRT
<213> ORGANISM: Artificial Sequence
<220> FEATURE:
<223> OTHER INFORMATION: Inert Portion

<400> SEQUENCE: 32

Gly Gly Gly Gly Ser Gly Gly Gly Gly Ser Val Asp
1               5                   10

<210> SEQ ID NO 33
<211> LENGTH: 12
<212> TYPE: PRT
<213> ORGANISM: Artificial Sequence
<220> FEATURE:
<223> OTHER INFORMATION: Inert Portion

<400> SEQUENCE: 33

Gly Gly Gly Gly Ser Gly Gly Gly Gly Ser Val Asp
1               5                   10

<210> SEQ ID NO 34
<211> LENGTH: 10
<212> TYPE: PRT
<213> ORGANISM: Artificial Sequence
<220> FEATURE:
<223> OTHER INFORMATION: Inert Portion

<400> SEQUENCE: 34

Gly Gly Gly Gly Ser Gly Gly Gly Gly Ser
1               5                   10
```

<210> SEQ ID NO 35
<211> LENGTH: 9
<212> TYPE: PRT
<213> ORGANISM: Artificial Sequence
<220> FEATURE:
<223> OTHER INFORMATION: Inert Portion

<400> SEQUENCE: 35

Gly Gly Gly Ser Gly Gly Gly Gly Ser
1               5

<210> SEQ ID NO 36
<211> LENGTH: 20
<212> TYPE: PRT
<213> ORGANISM: Artificial Sequence
<220> FEATURE:
<223> OTHER INFORMATION: Inert Portion
<220> FEATURE:
<221> NAME/KEY: VARIANT
<222> LOCATION: (1)..(5)
<223> OTHER INFORMATION: G, S, V, D, E, A, K, or P
<220> FEATURE:
<221> NAME/KEY: VARIANT
<222> LOCATION: (6)..(20)
<223> OTHER INFORMATION: G, S, V, D, E, A, K, P or absent

<400> SEQUENCE: 36

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa
            20

<210> SEQ ID NO 37
<211> LENGTH: 15
<212> TYPE: PRT
<213> ORGANISM: Artificial Sequence
<220> FEATURE:
<223> OTHER INFORMATION: Inert Portion
<220> FEATURE:
<221> NAME/KEY: VARIANT
<222> LOCATION: (1)..(5)
<223> OTHER INFORMATION: G, S, V, D, E, A, K, or P
<220> FEATURE:
<221> NAME/KEY: VARIANT
<222> LOCATION: (6)..(15)
<223> OTHER INFORMATION: G, S, V, D, E, A, K, P or absent

<400> SEQUENCE: 37

Xaa Xaa Xaa Xaa Xaa Xaa Xaa Xaa Xaa Xaa Xaa Xaa Xaa Xaa Xaa
1               5                   10                  15

<210> SEQ ID NO 38
<211> LENGTH: 20
<212> TYPE: PRT
<213> ORGANISM: Artificial Sequence
<220> FEATURE:
<223> OTHER INFORMATION: Inert Portion
<220> FEATURE:
<221> NAME/KEY: VARIANT
<222> LOCATION: (1)..(5)
<223> OTHER INFORMATION: G, S, V or D
<220> FEATURE:
<221> NAME/KEY: VARIANT
<222> LOCATION: (6)..(20)
<223> OTHER INFORMATION: G, S, V, D or absent

```
<400> SEQUENCE: 38

Xaa Xaa Xaa Xaa Xaa Xaa Xaa Xaa Xaa Xaa Xaa Xaa Xaa Xaa Xaa
1               5                   10                  15

Xaa Xaa Xaa Xaa
            20

<210> SEQ ID NO 39
<211> LENGTH: 15
<212> TYPE: PRT
<213> ORGANISM: Artificial Sequence
<220> FEATURE:
<223> OTHER INFORMATION: Inert Portion
<220> FEATURE:
<221> NAME/KEY: VARIANT
<222> LOCATION: (1)..(5)
<223> OTHER INFORMATION: G, S, V or D
<220> FEATURE:
<221> NAME/KEY: VARIANT
<222> LOCATION: (6)..(15)
<223> OTHER INFORMATION: G, S, V, D or absent

<400> SEQUENCE: 39

Xaa Xaa Xaa Xaa Xaa Xaa Xaa Xaa Xaa Xaa Xaa Xaa Xaa Xaa Xaa
1               5                   10                  15

<210> SEQ ID NO 40
<211> LENGTH: 30
<212> TYPE: DNA
<213> ORGANISM: Artificial Sequence
<220> FEATURE:
<223> OTHER INFORMATION: Oligonucleotide

<400> SEQUENCE: 40
ggcggcggca gcggcggcgg cagcgtggac                                      30

<210> SEQ ID NO 41
<211> LENGTH: 30
<212> TYPE: DNA
<213> ORGANISM: Artificial Sequence
<220> FEATURE:
<223> OTHER INFORMATION: Oligonucleotide

<400> SEQUENCE: 41
ggcggcggca gcggcggcgg cagcgtggac                                      30

<210> SEQ ID NO 42
<211> LENGTH: 30
<212> TYPE: DNA
<213> ORGANISM: Artificial Sequence
<220> FEATURE:
<223> OTHER INFORMATION: Oligonucleotide

<400> SEQUENCE: 42
ggcggcggct ccggcggcgg ctccgtggac                                      30

<210> SEQ ID NO 43
<211> LENGTH: 36
<212> TYPE: DNA
<213> ORGANISM: Artificial Sequence
<220> FEATURE:
<223> OTHER INFORMATION: Oligonucleotide

<400> SEQUENCE: 43
ggcggcggcg gcagcggcgg cggcggcagc gtggac                               36
```

```
<210> SEQ ID NO 44
<211> LENGTH: 36
<212> TYPE: DNA
<213> ORGANISM: Artificial Sequence
<220> FEATURE:
<223> OTHER INFORMATION: Oligonucleotide

<400> SEQUENCE: 44
ggcggcggcg gcagcggcgg cggcggcagc gtggac                              36

<210> SEQ ID NO 45
<211> LENGTH: 36
<212> TYPE: DNA
<213> ORGANISM: Artificial Sequence
<220> FEATURE:
<223> OTHER INFORMATION: Oligonucleotide

<400> SEQUENCE: 45
ggcggcggcg gctccggcgg cggcggctcc gtggac                              36

<210> SEQ ID NO 46
<211> LENGTH: 30
<212> TYPE: DNA
<213> ORGANISM: Artificial Sequence
<220> FEATURE:
<223> OTHER INFORMATION: Oligonucleotide

<400> SEQUENCE: 46
ggcggcggcg gcagcggcgg cggcggcagc                                     30

<210> SEQ ID NO 47
<211> LENGTH: 30
<212> TYPE: DNA
<213> ORGANISM: Artificial Sequence
<220> FEATURE:
<223> OTHER INFORMATION: Oligonucleotide

<400> SEQUENCE: 47
ggcggcggcg gcagcggcgg cggcggcagc                                     30

<210> SEQ ID NO 48
<211> LENGTH: 30
<212> TYPE: DNA
<213> ORGANISM: Artificial Sequence
<220> FEATURE:
<223> OTHER INFORMATION: Oligonucleotide

<400> SEQUENCE: 48
ggcggcggcg gctccggcgg cggcggctcc                                     30

<210> SEQ ID NO 49
<211> LENGTH: 27
<212> TYPE: DNA
<213> ORGANISM: Artificial Sequence
<220> FEATURE:
<223> OTHER INFORMATION: Oligonucleotide

<400> SEQUENCE: 49
ggcggcggca gcggcggcgg cggcagc                                        27

<210> SEQ ID NO 50
<211> LENGTH: 27
<212> TYPE: DNA
<213> ORGANISM: Artificial Sequence
<220> FEATURE:
<223> OTHER INFORMATION: Oligonucleotide
```

```
<400> SEQUENCE: 50
ggcggcggca gcggcggcgg cggcagc                                        27

<210> SEQ ID NO 51
<211> LENGTH: 27
<212> TYPE: DNA
<213> ORGANISM: Artificial Sequence
<220> FEATURE:
<223> OTHER INFORMATION: Oligonucleotide

<400> SEQUENCE: 51
ggcggcggct ccggcggcgg cggctcc                                        27

<210> SEQ ID NO 52
<211> LENGTH: 5
<212> TYPE: PRT
<213> ORGANISM: Artificial Sequence
<220> FEATURE:
<223> OTHER INFORMATION: Inert Portion

<400> SEQUENCE: 52

Glu Ala Ala Ala Lys
1               5

<210> SEQ ID NO 53
<211> LENGTH: 5
<212> TYPE: PRT
<213> ORGANISM: Artificial Sequence
<220> FEATURE:
<223> OTHER INFORMATION: Inert Portion

<400> SEQUENCE: 53

Pro Pro Pro Pro Pro
1               5

<210> SEQ ID NO 54
<211> LENGTH: 15
<212> TYPE: DNA
<213> ORGANISM: Artificial Sequence
<220> FEATURE:
<223> OTHER INFORMATION: Oligonucleotide

<400> SEQUENCE: 54
gaagccgctg caaag                                                     15

<210> SEQ ID NO 55
<211> LENGTH: 15
<212> TYPE: DNA
<213> ORGANISM: Artificial Sequence
<220> FEATURE:
<223> OTHER INFORMATION: Oligonucleotide

<400> SEQUENCE: 55
gaagcagccg ctaag                                                     15

<210> SEQ ID NO 56
<211> LENGTH: 15
<212> TYPE: DNA
<213> ORGANISM: Artificial Sequence
<220> FEATURE:
<223> OTHER INFORMATION: Oligonucleotide

<400> SEQUENCE: 56
gaggccgcag ccaaa                                                     15
```

```
<210> SEQ ID NO 57
<211> LENGTH: 15
<212> TYPE: DNA
<213> ORGANISM: Artificial Sequence
<220> FEATURE:
<223> OTHER INFORMATION: Oligonucleotide

<400> SEQUENCE: 57
cctcctcccc ctcct                                                    15

<210> SEQ ID NO 58
<211> LENGTH: 15
<212> TYPE: DNA
<213> ORGANISM: Artificial Sequence
<220> FEATURE:
<223> OTHER INFORMATION: Oligonucleotide

<400> SEQUENCE: 58 cccccctcccc cccct                                                   15

<210> SEQ ID NO 59
<211> LENGTH: 15
<212> TYPE: DNA
<213> ORGANISM: Artificial Sequence
<220> FEATURE:
<223> OTHER INFORMATION: Oligonucleotide

<400> SEQUENCE: 59
cccccgccgc cgcca                                                    15

<210> SEQ ID NO 60
<211> LENGTH: 5
<212> TYPE: PRT
<213> ORGANISM: Artificial Sequence
<220> FEATURE:
<223> OTHER INFORMATION: Inert Portion Subunit

<400> SEQUENCE: 60

Glu Ala Ala Ala Lys
1               5

<210> SEQ ID NO 61
<211> LENGTH: 5
<212> TYPE: PRT
<213> ORGANISM: Artificial Sequence
<220> FEATURE:
<223> OTHER INFORMATION: Inert Portion Subunit

<400> SEQUENCE: 61

Gly Gly Gly Gly Ser
1               5

<210> SEQ ID NO 62
<211> LENGTH: 15
<212> TYPE: DNA
<213> ORGANISM: Artificial Sequence
<220> FEATURE:
<223> OTHER INFORMATION: Oligonucleotide

<400> SEQUENCE: 62
gaagccgctg caaag                                                    15

<210> SEQ ID NO 63
<211> LENGTH: 15
<212> TYPE: DNA
<213> ORGANISM: Artificial Sequence
```

```
<220> FEATURE:
<223> OTHER INFORMATION: Oligonucleotide

<400> SEQUENCE: 63
gaagcagccg ctaag                                              15

<210> SEQ ID NO 64
<211> LENGTH: 15
<212> TYPE: DNA
<213> ORGANISM: Artificial Sequence
<220> FEATURE:
<223> OTHER INFORMATION: Oligonucleotide

<400> SEQUENCE: 64
gaggccgcag ccaaa                                              15

<210> SEQ ID NO 65
<211> LENGTH: 15
<212> TYPE: DNA
<213> ORGANISM: Artificial Sequence
<220> FEATURE:
<223> OTHER INFORMATION: Oligonucleotide

<400> SEQUENCE: 65
ggtggaggcg gttcc                                              15

<210> SEQ ID NO 66
<211> LENGTH: 15
<212> TYPE: DNA
<213> ORGANISM: Artificial Sequence
<220> FEATURE:
<223> OTHER INFORMATION: Oligonucleotide

<400> SEQUENCE: 66
ggaggtggcg ggagc                                              15

<210> SEQ ID NO 67
<211> LENGTH: 15
<212> TYPE: DNA
<213> ORGANISM: Artificial Sequence
<220> FEATURE:
<223> OTHER INFORMATION: Oligonucleotide

<400> SEQUENCE: 67
ggcggtggcg gtagt                                              15

<210> SEQ ID NO 68
<211> LENGTH: 60
<212> TYPE: DNA
<213> ORGANISM: Artificial Sequence
<220> FEATURE:
<223> OTHER INFORMATION: DNA molecule encoding the peptide having the
      amino acid sequence corresponding to SEQ ID. NO. 36 or SEQ ID. NO.
      38.
<220> FEATURE:
<221> NAME/KEY: misc_feature
<222> LOCATION: (1)..(60)
<223> OTHER INFORMATION: represent any bases capable of forming codons
      encoding residues 1 to 20 of SEQ ID NO. 36 or of SEQ ID NO. 38.

<400> SEQUENCE: 68
nnnnnnnnnn nnnnnnnnnn nnnnnnnnnn nnnnnnnnnn nnnnnnnnnn nnnnnnnnnn   60

<210> SEQ ID NO 69
<211> LENGTH: 45
<212> TYPE: DNA
<213> ORGANISM: Artificial Sequence
```

```
<220> FEATURE:
<223> OTHER INFORMATION: DNA molecule encoding the peptide having the
      amino acid sequence corresponding to SEQ ID NO. 37 or SEQ ID. NO.
      39.
<220> FEATURE:
<221> NAME/KEY: misc_feature
<222> LOCATION: (1)..(45)
<223> OTHER INFORMATION: represent any base capable of forming codons
      encoding residues 1 to 15 of SEQ ID. NO. 37 or SEQ ID. NO. 39.

<400> SEQUENCE: 69
nnnnnnnnnn nnnnnnnnnn nnnnnnnnnn nnnnnnnnnn nnnnn              45

<210> SEQ ID NO 70
<211> LENGTH: 84
<212> TYPE: DNA
<213> ORGANISM: Artificial Sequence
<220> FEATURE:
<223> OTHER INFORMATION: Oligonucleotide

<400> SEQUENCE: 70
atgggagggg ggggttcagg tggtggcggg agtcgagacc acatggtatt gcacgaatac    60
gtcaacgccg caggcataac atga                                          84

<210> SEQ ID NO 71
<211> LENGTH: 90
<212> TYPE: DNA
<213> ORGANISM: Artificial Sequence
<220> FEATURE:
<223> OTHER INFORMATION: Oligonucleotide

<400> SEQUENCE: 71
atgggagggg ggggttcagg tggtggcggg agttacacca tcgtggagca gtacgagaga    60
gccgagggca gacacagcac cggcggctga                                    90

<210> SEQ ID NO 72
<211> LENGTH: 135
<212> TYPE: DNA
<213> ORGANISM: Artificial Sequence
<220> FEATURE:
<223> OTHER INFORMATION: Oligonucleotide

<400> SEQUENCE: 72
atgggagggg gccccgacgc ccacttcgtg gaccaccgca tcgagatcct gggcaacgac    60
agcgactaca acaaggtgaa gctgtacgag cacgccgtgg cccgctacag ccccctgccc   120
agccaggtgt ggtaa                                                   135

<210> SEQ ID NO 73
<211> LENGTH: 66
<212> TYPE: DNA
<213> ORGANISM: Artificial Sequence
<220> FEATURE:
<223> OTHER INFORMATION: Oligonucleotide

<400> SEQUENCE: 73
ggaagcggag cgacgaattt tagtctactg aaacaagcgg gagacgtgga ggaaaaccct    60
ggacct                                                             66

<210> SEQ ID NO 74
<211> LENGTH: 27
<212> TYPE: PRT
<213> ORGANISM: Artificial Sequence
<220> FEATURE:
<223> OTHER INFORMATION: GFP11
```

```
<400> SEQUENCE: 74

Met Gly Gly Gly Gly Ser Gly Gly Gly Ser Arg Asp His Met Val
1               5                   10                  15

Leu His Glu Tyr Val Asn Ala Ala Gly Ile Thr
            20                  25

<210> SEQ ID NO 75
<211> LENGTH: 29
<212> TYPE: PRT
<213> ORGANISM: Artificial Sequence
<220> FEATURE:
<223> OTHER INFORMATION: sfCherry11

<400> SEQUENCE: 75

Met Gly Gly Gly Gly Ser Gly Gly Gly Ser Tyr Thr Ile Val Glu
1               5                   10                  15

Gln Tyr Glu Arg Ala Glu Gly Arg His Ser Thr Gly Gly
            20                  25

<210> SEQ ID NO 76
<211> LENGTH: 44
<212> TYPE: PRT
<213> ORGANISM: Artificial Sequence
<220> FEATURE:
<223> OTHER INFORMATION: Dendra11

<400> SEQUENCE: 76

Met Gly Gly Gly Pro Asp Ala His Phe Val Asp His Arg Ile Glu Ile
1               5                   10                  15

Leu Gly Asn Asp Ser Asp Tyr Asn Lys Val Lys Leu Tyr Glu His Ala
            20                  25                  30

Val Ala Arg Tyr Ser Pro Leu Pro Ser Gln Val Trp
        35                  40

<210> SEQ ID NO 77
<211> LENGTH: 22
<212> TYPE: PRT
<213> ORGANISM: Artificial Sequence
<220> FEATURE:
<223> OTHER INFORMATION: PQR

<400> SEQUENCE: 77

Gly Ser Gly Ala Thr Asn Phe Ser Leu Leu Lys Gln Ala Gly Asp Val
1               5                   10                  15

Glu Glu Asn Pro Gly Pro
            20

<210> SEQ ID NO 78
<211> LENGTH: 16
<212> TYPE: PRT
<213> ORGANISM: Artificial Sequence
<220> FEATURE:
<223> OTHER INFORMATION: GFP11

<400> SEQUENCE: 78

Arg Asp His Met Val Leu His Glu Tyr Val Asn Ala Ala Gly Ile Thr
1               5                   10                  15

<210> SEQ ID NO 79
<211> LENGTH: 16
<212> TYPE: PRT
<213> ORGANISM: Artificial Sequence
<220> FEATURE:
<223> OTHER INFORMATION: GFP11
```

-continued

```
<400> SEQUENCE: 79

Arg Asp His Met Val Leu Leu Glu Phe Val Thr Ala Ala Gly Ile Thr
1               5                   10                  15

<210> SEQ ID NO 80
<211> LENGTH: 16
<212> TYPE: PRT
<213> ORGANISM: Artificial Sequence
<220> FEATURE:
<223> OTHER INFORMATION: GFP11

<400> SEQUENCE: 80

Arg Asp His Met Val Leu His Glu Phe Val Thr Ala Ala Gly Ile Thr
1               5                   10                  15

<210> SEQ ID NO 81
<211> LENGTH: 13
<212> TYPE: RNA
<213> ORGANISM: Artificial Sequence
<220> FEATURE:
<223> OTHER INFORMATION: Poly(A) tail

<400> SEQUENCE: 81
aaaaaaaaaa aaa                                                          13

<210> SEQ ID NO 82
<211> LENGTH: 16
<212> TYPE: PRT
<213> ORGANISM: Artificial Sequence
<220> FEATURE:
<223> OTHER INFORMATION: PQR

<400> SEQUENCE: 82

Arg Asp His Met Val Leu His Glu Tyr Val Asn Ala Ala Gly Ile Thr
1               5                   10                  15

<210> SEQ ID NO 83
<211> LENGTH: 10
<212> TYPE: RNA
<213> ORGANISM: Artificial Sequence
<220> FEATURE:
<223> OTHER INFORMATION: Poly(A) Tail

<400> SEQUENCE: 83
aaaaaaaaaa                                                              10

<210> SEQ ID NO 84
<211> LENGTH: 21
<212> TYPE: PRT
<213> ORGANISM: Artificial Sequence
<220> FEATURE:
<223> OTHER INFORMATION: PQR

<400> SEQUENCE: 84

Gly Ser Gly Ala Thr Met Phe Ser Leu Leu Lys Gln Ala Gly Asp Val
1               5                   10                  15

Glu Glu Asn Pro Gly
            20
```